(12) United States Patent
Schwartz et al.

(10) Patent No.: US 6,596,701 B1
(45) Date of Patent: *Jul. 22, 2003

(54) S-ADENOSYL METHIONINE REGULATION OF METABOLIC PATHWAYS AND ITS USE IN DIAGNOSIS AND THERAPY

(75) Inventors: Dennis E. Schwartz, Redmond, WA (US); Nicolaas M. J. Vermeulen, Woodinville, WA (US); Christine L. O'Day, Mountlake Terrace, WA (US)

(73) Assignee: MediQuest Therapeutics, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/930,128

(22) PCT Filed: Apr. 25, 1996

(86) PCT No.: PCT/US96/05799

§ 371 (c)(1),
(2), (4) Date: Mar. 16, 1998

(87) PCT Pub. No.: WO96/33703

PCT Pub. Date: Oct. 31, 1996

Related U.S. Application Data

(63) Continuation-in-part of application No. 08/476,447, filed on Jun. 7, 1995, now abandoned, and a continuation-in-part of application No. 08/428,963, filed on Apr. 25, 1995.

(51) Int. Cl.$^7$ .................... A01N 43/04; G01N 33/53; C08G 69/26

(52) U.S. Cl. ..................... 514/46; 435/7.1; 528/338; 528/340

(58) Field of Search ................. 435/7.1; 514/46; 528/338, 340

(56) References Cited

U.S. PATENT DOCUMENTS

| | | |
|---|---|---|
| 4,373,097 A | 2/1983 | Stramentinoli et al. |
| 4,465,672 A | 8/1984 | Gennari |
| 4,499,072 A | 2/1985 | Sunkara et al. |
| 4,971,986 A | 11/1990 | Stanek et al. |
| 5,043,268 A | 8/1991 | Stock |
| 5,132,293 A | 7/1992 | Shander et al. |
| 5,180,714 A | 1/1993 | Sufrin et al. |
| 5,264,355 A | 11/1993 | Shafiee et al. |
| 5,389,653 A | 2/1995 | Bernauer et al. |
| 5,428,063 A | 6/1995 | Barak et al. |
| 5,476,875 A | 12/1995 | Bernauer et al. |

FOREIGN PATENT DOCUMENTS

| | | |
|---|---|---|
| EP | A2 0 211 354 | 7/1985 |
| EP | A2 0 358 536 | 6/1989 |

OTHER PUBLICATIONS advertisement, Country Living, vol. 22, No. 11, Nov. 1999 issue, p. 37, Oct. 9, 1999.*
Baker et al., "2'–Deoxy–2'–methylenecytidine and 2'–Deoxy–2',2'–difluorocytidine 5'–Diphosphates: Potent Mechanism–Based Inhibitors of Ribonucleotide Reductase" *J. Med. Chem.* 34:1879–1884 (1991).
Berger, "Cancer Chemotherapy: New Strategies for Success" *J. Clin. Invest.* 78:1131–1135 (1986).
Beutler, et al., "2–Chlorodeoxyadenosine: Hairy Cell Leukemia Takes a Surprising Turn" *Blood Cells* 19:559–568 (1993).
Blaney, et al. "Structure–Activity Relationships of Dihydrofolate Reductase Inhibitors" *Chem. Rev.* 84:333–407 (1984).
Borchardt, et al., "Experimental and Clinical Role of S–Adenosylmethionine" *Biological Methylation and Drug Design* Humana Press pp. 363–370.
Bottiglieri, et al. "The Clinical Potential of Ademetionine (S–Adenosylmethionine) in Neurological Disorders" *Drugs* 48 (2):137–152 (1994).
Byers, et al., "The role of hypusine depletion in cytostasis induced by S–adenosyl–L methionine decarboxylase inhibiton: new evidence provided by 1–methylspermidine and 1,12–dimethylspermine" *Biochem. J.* 303:363–368 (1994).
Chrominski, et al., "Exposure to Ethylene Changes Nymphal Growth Rate and Female Longevity in the Grasshopper *Melanoplus sanguinipes*" *Naturwissenschaften* 69:45–46 (1982).
Coggeshall, et al., "Biotin Status and Plasma Glucose in Diabetics", Annals NY Acad. Sciences, 447: 389–392 (1985).
Cui, et al., "Suppression of Rat Hepatoma Cell Growth by Expression of Phosphatidylethanolamine N–Methyltransferase–2" *The Journal of Biological Chemistry* 269:24531–24533 (1994).
Dakshinamurti, et al., "Some Aspects of Carbohydrates Metabolism in Biotin–Deficient Rats", Proceedings Soc. Exp. Biol. Med. 127:346–400 (1968).
Deodhar, et al., "Regulation of Glycolysis in Biotin–Deficient Rat Liver" Life Sciences, vol. 9, Part II, pp. 581–588, (1970).
Deodhar et al., "Control of Gluconeogenesis in Biotin–Deficient Rat Liver" Arch. of Biochem. and Biopys., vol. 129: 321–328 (1969).

(List continued on next page.)

*Primary Examiner*—Rodney P Swartz
(74) *Attorney, Agent, or Firm*—Morrison & Foerster LLP

(57) ABSTRACT

A new paradigm of disease centers around the metabolic pathways of S-adenosyl-L-methionine (SAM), the intermediates of these pathways and other metabolic pathways influenced by the SAM pathways. Methods are provided to analyze and modulate SAM pathways associated with a disease or condition. Such methods permit identification and utilization of diagnostic and therapeutic protocols and agents for such disease states and conditions.

21 Claims, 15 Drawing Sheets

OTHER PUBLICATIONS

Deodhar, et al., "Restoration of Gluconeogenesis in Biotin-Deficient Rats" Arch. of Biochem. and Biopys., vol. 131:507–512 (1969).

Deodhar, et al., "Gluconeogenesis in Biotin Deficiency: In Vivo Synthesis of Pyruvate Holocarboxylase in Biotin Deficient Rat Liver", Biochem. and Biophys. Res. Communications, vol. 34, No. 6, (1969).

Dubois, et al., "Variation of choline–substituted lipid metabolism in doxorubicin–resistant leukemia cells" Biomed & Pharmacother 46:485–490 (1992).

Eliasson, et al., "Interaction of 2'–Modified Azido– and Haloanalogs of Deoxycytidine 5'–Triphosphate with the Anaerobic Ribonucleotide Reductase of Escherichia coli" The Journal of Biological Chemistry 269:26116–26120 (1994).

Erlichman, "Novel chemotherapeutic agents in clinical development" Current Opinion in Oncology 3:1037–1042 (1991).

Friedel, "S–Adenosyl–L–Methioniney" Drugs 38 (3):389–416 (1989).

Gündüz, et al. "Absence of RNA–guanine transglycosylase in a human colon adenocarcinome cell line" Biochimica et Biophysica Acta 1139:229–238 (1992).

Harrison, "Ethylene, an Ovulatory Hormone?" The Lancet pp. 438 (1981).

Hartman, "Molecular Aspects and Mechanism of Action of Dihydrofolate Reductase Inhibitors" Journal of Chemotherapy 5:369–376 (1993).

Hopkin, "Move Over, Mutations: DNA Methylation May Drive Cancer, Too" The Journal of NIH Research 7:26–28 (1995).

Hrycyna, et al., "Modification of Eukaryotic Signaling Proteins by C–Terminal Methylation Reactions" Pharmac. Ther. 59:281–300 (1993).

Huang, et al., "Relationship of the Queuine Content of Transfer Ribonucleic Acids to Histopathological Grading and Survival in Human Lung Cancer" Cancer Research 52:4696–4700 (1992).

Kamatani, et al., "Selective killing of human malignant cell lines deficient in methylthioadenosine phosphorylase, a purine metabolic enzyme" Proc. Natl. Acad. Sci. USA 78:1219–1223 (1981).

Kerr, "Competing Methyltransferase Systems" The Journal of Biological Chemistry 247:4248–4252 (1972).

Kido, et al., "Effects of Methylthiodeoxyadenosime and Its Analogs on in vitro Invasion of Rat Ascites Hepatoma Cells and Methylation of Their Phospholipids" Jpn. J. Cancer Res. 82:1104–1111 (1991).

König, "A Long–Term (Two Years) Clinical Trial With S–Adenosylmethionine for the Treatment of Osteoarthritis" The American Journal of Medicine 83:89–93 (1987).

Laird, et al., "Suppression of Intestinal Neoplasia by DNA Hypomethylation" Cell 81:197–205 (1995).

Luckhardt, et al., "Clinical Experiences With Ethylene–Oxigen Anesthesia" J. Amer. Med. Assoc. 81:1851–1857 (1923).

Marton, "Polyamines as Targets for Therapeutic Intervention" Annu.Rev. Pharmacol. Toxicol. 35:55–91 (1995).

Nishimura, et al., "Characterization and Analysis of Oncofetal tRNA and Its Possible Application for Cancer Diagnosis and Therapy" Recent Result in Cancer Research 84:401–412 (1983).

Pegg, et al., "S–Adenosylmethionine Decarboxylase as an Enzyme Target for Therapy" Pharmac. Ther. 56:359–377 (1992).

Purifoy, et al., "Review of Research Leading to New Anti-Herpesvirus Agents in Clinical Development: Valaciclovir Hydrochloride (256U, the L–Valyl Ester of Acyclovir) and 882C, a Specific Agent for Varicella Zoster Virus" Journal of Medical Virology Supplement 1:139–145.

Reddi et al , "Bioten Supplementation Improves Glucose and Insulin Tolerance in Genetically Diabetic KK Mice"; Life Sci., 42:1323–1330, 1988.

Reddi, et al., "Diabetes Mellitus in the KK Mouse: Similarities and Differences Between Genetic and Other Types of Diabetes"; Secondary Diabetes: The Spectrum of the Diabetic Syndromes, edited by S. Podolsky and M. Viswanathan. Raven Press, New York, 455–469, 1980.

Selhub, et al., "The Pathogenesis of homocysteinemia: interruption of the coordinate regulation by S–adenosylmethionine of the remethylation and transsulfuration of homocysteine" American Society for Clinical Nutrition 55:131–138 (1992).

Smith, et al., "Tumor–specific, Hypomodified Phenylalanyl-tRNA is Utilized in Translation in Preference to the Fully Modified Isoacceptor of Normal Cells" The Journal of Biological Chemistry 260:147–151 (1985).

Sufrin, et al., "Differential kinetic properties of L–2–amino–4–methylthio–cis–but–3–enoic acid, a methionine analog inhibitor of S–adenosylmethionine synthetase" Biochimica et Biophysica Acta, 1202:87–91 (1993).

Swift, et al., "Gram–negative bacterial communication by N–acyl homoserine lactones: a universal language?" Trends in Microbiology 2:193–198 (1994).

Wolfe, et al., "S–Adenosyl L–homocysteine Hydrolase as a Target for Antiviral Chemotherapy" Journal of Medical Chemistry 34:1521–1530 (1991).

Williams–Ashman et al., "Trends in the Biochemical Pharmacology of 5'–Deoxy–5'–Methylthioadenosine" Biochemical Pharmacology 31:277–288 (1982).

Wolos, et al., "Selective Inhibition of T Cell Activation by an Inhibitor of S–Adenosyl–L–Homocysteine Hydrolase" The Journal of Immunology 150:3264–3273 (1993).

Abstract Biophysical Journal 61:A39 (1992).

Impairment of Glucose Utilization in Biotin Deficiency, Arch. Biochem. Biophys., 96:674–675 (1962).

If Love Can Last, Why Not Flowers? Houston Chronicles Feb. 12, 1992.

* cited by examiner

S-ADENOSYL METHIONINE REGULATION OF METABOLIC PATHWAYS AND ITS USE IN DIAGNOSIS AND THERAPY

This application is a 371 of PCT/US96/05799 filed Apr. 25, 1999 and a continuation in part of Ser. No. 08/476,447 filed Jun. 7, 1995 now abandoned and a continuation in part of Ser. No. 08/428,963 filed Apr. 25, 1995.

BACKGROUND OF THE INVENTION

1. Field of the Invention

The invention relates to a new paradigm of disease centering around the metabolic pathways of S-adenosyl-L-methionine (SAM), the intermediates of these pathways and other metabolic pathways influenced by the SAM pathways. Specifically, the invention relates to analyzing and regulating SAM pathways that exist in association with a disease or condition including cancer and a number of diseases or conditions connected with degeneration and aging. More specifically, the invention concerns designing analytical, diagnostic and therapeutic protocols and agents for such disease states and conditions through recognition of the central role of SAM and its metabolic pathways in controlling cell metabolism, cell growth and intercellular communication.

2. Description of the Background Art

It is commonly believed that an understanding of cellular metabolism and function, as well as the nature of biological degeneration and the creation of disease conditions, can be achieved by ascertaining the genetic information contained in eukaryotic cells and understanding how this genetic information is transcribed and translated into proteins which then control chemical conversions within the cell. The present conceptual frame work considers DNA as the core of life. Within this framework, the function of proteins is commonly assumed to be regulated in large part by phosphorylation and dephosphorylation of relevant proteins at appropriate times.

The present invention was made in response to the absence of a greater unifying relationship between small molecule biochemistry and the macromolecules RNA, DNA and protein. Present-day molecular biology is focused completely on macromolecules and has provided essentially no connection with the small molecules which carry out the chemical reactions of life. In fact, the study of small molecules in the biological and biochemical sciences has not been in vogue for the last 20 years.

The present inventors have recognized that the focus of the present paradigm for metabolic management are at best very incomplete. Such a recognition demands a "paradigm shift" of the sort described by Thomas Kuhn in *The Structure of Scientific Revolutions* (2nd ed., University of Chicago Press (1970)). The prevailing view will change completely when a single paradigm shift is made which defines the conceptual basis for the present invention. This paradigm shift is to the view of the present invention, that life is regulated by S-adenosyl-L-methionine (SAM) through at least eight "donor/cleavage" pathways. In addition, as conceived by the present inventors, significant regulation occurs at the RNA level as opposed to the DNA level.

It is proposed here that our present state of knowledge and interpretation of disease has evolved into two classes which are termed by the present inventors: (1) "exogenous disease", for example that caused by viruses, bacteria and organisms exogenous to the affected subject, and (2) "endogenous disease", such as cancer and arthritis, largely associated with internal changes in the affected subject and frequently associated with aging. At present, understanding of exogenous disease is greater due to our knowledge of the external and identifiable causative agents. This knowledge has provided diagnostic and therapeutic procedures which are quite effective against many pathological states, such as bacterial infections. Comparatively speaking, we understand surprisingly little about endogenous diseases. While an enormous body of facts surrounding most endogenous diseases exists, we unfortunately have minimal molecular understanding of their etiology. The reason for this is simple: we have been adhering to the wrong paradigm, a DNA-centered conceptual framework which does not include regulation through RNA or through the eight pathways of SAM.

With the new view of life in accordance with the paradigm shift described herein, the diseases of man can be understood from an entirely new perspective. Most importantly, and practically, from this novel view of life and biochemical processes, the present invention suggests ways to discover and implement new diagnostics and therapeutics for virtually every endogenous disease of man, as well as many exogenous diseases such as bacterial and viral infections.

The recognition of the centrality of the eight "donor/cleavage" pathways of SAM by the present inventors and their application to disease will radically alter the existing paradigm since SAM merges the biochemistry of small molecules with that of macromolecules. In order to design methods to assess the overall metabolic state of a eukaryotic organism and to modulate this state in response to a disease or a dysfunctional condition, the central role of SAM in controlling a host of biochemical reactions must be recognized and employed.

A number of publications which describe SAM and SAM metabolism are delineated below.

Several U.S. patents describe SAM, its activity, and various metabolites and utilities thereof U.S. Pat. No. 4,369,177 discloses a stable composition of SAM which includes a salt of SAM in a pharmaceutically acceptable water-soluble salt of a bivalent or trivalent metal. SAM is said to have pharmaceutical effects in various disorders including adipohepatica, hyperlipemia, arteriosclerosis, depression, arthritis deformans, pains in some neurological manifestations and sleeplessness.

U.S. Pat. No. 4,956,173 discloses use of ademethionine (a common name for a SAM salt) for the preparation of pharmaceutical or cosmetic compositions for counteracting aging of the skin. Ademethionine is said to be a physiological molecule of virtually ubiquitous distribution in the tissues and liquids of the organism where it is involved in important biological processes as a donor of methyl groups in numerous transmethylation reactions and as a precursor of physiological sulfur compounds such as glutathione, cysteine, taurine and CoA. Levels of SAM are known to be high in children and adolescents whereas they are lower in adults and subsequently decrease in presenility and senility. SAM is the active principle of drugs used especially for the treatment of degenerative osteoarthropathy where it has an important role through its antiphlogistic and analgesic activity due to its intervention in the metabolism of arachidonic acid and prostaglandins. Ademethionine is also indicated in the treatment of depressive syndromes.

U.S. Pat. No. 4,764,603 discloses SAM salts with water-soluble polyanions such as polyphosphates, polyvinylsulfonates, sulfates or phosphates, polyacrylates, polystyrene sulfonates.

U.S. Pat. No. 5,073,546 discloses liposoluble salts of SAM with acyl derivatives of taurine. This reference lists a number of important biochemical functions of SAM and summarizes various pharmacologic effects of SAM in test models and the use in clinical pathologies.

U.S. Pat. No. 4,605,625 discloses production of S-adenosyl-L-homocysteine (SAH) by contacting adenosine with D-homocysteine in an aqueous medium in the presence of Pseudomonas cells having the ability to racemize D-homocysteine to D-L-homocysteine and in the presence of SAH hydrolase to synthesize SAH. SAH is said to be an important biologically active substance formed by a methyl group donating reaction in vivo involving SAM. SAH was said to be efficacious as a sedative and a sleep-inducing agent.

U.S. Pat. No. 4,562,149 discloses yeast cultures containing SAM in high concentrations and a process for producing SAM by cultivating the yeast in a liquid culture medium containing methionine.

U.S. Pat. No. 4,242,505 discloses stabilized SAM compositions a sulfuric acid equivalent and a nucleoside sulfate. U.S. Pat. No. 4,057,686 discloses stable sulfonic acid salt of SAM.

U.S. Pat. No. 4,028,183 discloses preparation of double salts of SAM by the action of the enzyme ATP-methionine-adenosyl-transferase on a mixture of ATP and methionine. U.S. Pat. No. 3,954,726 discloses double salts of SAM with sulfuric acid and p-toluene sulfonic acid.

U.S. Pat. No. 3,962,034 discloses production of SAM and methylthioadenosine by yeast cultured in media containing L-methionine.

U.S. Pat. No. 4,599,309 discloses treatment of yeast cells following cultivation to facilitate product recovery. Among the many substances recoverable from such cells are SAM.

U.S. Pat. No. 5,100,786 discloses a gene which provides cellular resistance to at least one methionine derivative and is capable of enhancing accumulation of SAM in a cell. Also disclosed are a plasmid containing this gene, a cell transformed with the plasmid and a process for producing SAM using the above cells in a large amount at low cost. SAM is said to participate in metabolism of fats, proteins, sugar chains and the like and to have effects in the therapy of excessive lipemia, arteriosclerosis, psychosis manifestations such as depression and neuropathic diseases, degenerative arthropathy, neuropathic pain, sleeplessness, brain damage, and the like. The gene described in this reference is referred to as the "SAM gene" which enables cells to accumulate SAM in large amounts though the gene also provides the cell with ethionine resistance.

U.S. Pat. No. 5,132,291 discloses antiviral purine nucleosides, analogs and prodrugs and methods of enhancing the antiviral activity of AZT. Some of the purine nucleoside analogs inhibit SAH hydrolase, an enzyme which converts SAH to adenosine and homocysteine. Inhibition of this enzyme causes a build-up of SAH, which in turn inhibits SAM-mediated methylation and the conversion of SAM to SAH. This latter inhibition is said to destabilize viral mRNA which is normally stabilized in part by methylation at the 5'-terminus to form the cap structure found in mammalian mRNA.

U.S. Pat. No. 4,376,116 discloses compounds which inhibit polyamine biosynthesis and cites U.S. Pat. Nos. 3,954,726 and 4,028,183 as describing the preparation of stable salts of SAM which is the parent compound of decarboxylated SAM (dcSAM). Such polyamine synthesis inhibitors are said to be useful as antiparasitic agents and in the treatment of cancer and cystic fibrosis.

U.S. Pat. No. 5,087,417 states that the biosynthetic path leading to ethylene formation begins with conversion of methionine to SAM, SAM to 1-amino-cyclopropane-1-carboxylic acid (ACC), and thence to ethylene. This reference describes the isolation and identification of the compounds which inhibit senescence in perishable plant tissue from petals of senescing carnation flowers. The active compound, a glucose ester of ferulic acid, inhibits ACC-to-ethylene conversion, ethylene formation in vitro and lipoxygenase activity.

U.S. Pat. No. 4,275,150 discloses an assay for measurement of normetanephrine in biological systems of patients in particular for hypertension or for detection of pheochromocytoma. This method utilizes conversion of normetanephrine to its N-methylated (and tritiated) derivative, metanephrine, utilizing SAM as methyl donor U.S. Pat. Nos. 5,264,355 5,198,358 5,149,701 discloses a new methylating enzyme from Streptomyces, which uses SAM as a methyl donor in methylating various FK 506-related agents. These immunosuppressants are said to be useful for treating autoimmune diseases, infectious diseases, graft rejection, reversible obstructive airway disease, inflammatory and hyperproliferative skin disease, cutaneous manifestations of immunologically mediated illness, male pattern alopecia and alopecia senilis.

None of the documents cited above provide any insight into the present invention nor do they lead a person of ordinary skill in the art to the present claims.

SUMMARY OF THE INVENTION

The invention provides a new and useful paradigm for understanding a number of disease states or unwanted conditions and for identifying suitable molecular targets for intervention to control or ameliorate such diseases or conditions. This approach allows assessment of the overall biochemical/metabolic status of an organism. The methods and compositions focus on the eight metabolic pathways involving, and ultimately controlled by, SAM.

Thus, in one aspect, the invention is directed to a method to identify a therapeutic composition or protocol which modulates metabolism of a SAM pathway in a subject having a disease or undesired condition associated with altered SAM metabolism. The intended composition or protocol identified here, which is useful in ameliorating the disease or condition, is one which has not been previously identified as being useful for treating the particular disease or condition. The method comprises a number of steps:

a) determining the presence of the disease or condition in the subject or a biological fluid thereof;

b) identifying one or more of the SAM pathways or a metabolite of the pathways which is abnormal in amount, activity or modification and/or association with other cellular proteins, in the disease or condition;

c) determining which of the abnormal pathways or metabolites should be increased or decreased in activity or amount in order to ameliorate the disease or condition, thereby generating a first data set of target pathways or metabolites;

d) identifying a therapeutic composition or protocol which stimulates or suppresses the target pathway or increases or decreases the amount of the target metabolite, thereby identifying the therapeutic composition or protocol useful in ameliorating the disease or condition.

In another embodiment, this method further comprises, after step (b) above, the step of prioritizing the pathways or metabolites of the first data set in order of deviation from normal to obtain a second data set of one or more target pathways and/or metabolites which are most abnormal, and wherein step (d) comprises identifying a therapeutic composition or protocol which stimulates or suppresses the second data set target pathway or increases or decreases the amount of the second data set target metabolite.

In the above methods, the first or second data set may be converted into digital computer-readable form for storage, access, manipulation, analysis and educational use. The results of any determination or identification made in any of the steps of the various methods disclosed herein may likewise be converted into digital computer-readable form.

In the above method, the identifying step (b) may be performed by subjecting a biological fluid obtained from the subject to (i) direct measurement of the concentration of one or more of the metabolites or the activity of an enzyme; or (ii) affinity chromatography with immobilized affinity ligands which bind to SAM metabolites or macromolecules involved in a SAM pathway. Such an affinity-based identification ("hardwiring") approach may not identify all the potential SAM paradigm-based targets. For example, proteins, nucleic acids, lipids, sugars, and other small molecules may be modified by SAM or SAM pathway intermediates. These aberrant modifications in diseased states may not always be detected by the above affinity-based method. In these instances an additional approach (iii) termed "labeling" is preferred, comprising the following steps:

(a) obtaining a biological fluid from a subject having the disease or condition;

(b) contacting the fluid representing the disease state, which may be in the form of isolated enzyme(s), proteins, nucleic acids, a cell-free system, cultured cells, or an in vivo model of the disease state, with detectably labeled, preferably radiolabeled, SAM or a SAM pathway intermediate, and thereby allowing labeling of SAM pathway intermediates or of molecules to which the radiolabel is donated from the labeled SAM pathway precursor (intermediate);

(c) isolating any labeled components from the fluid;

(d) identifying any such labeled components;

(e) performing steps (a) to (d) with a biological fluid from a normal subject or a subject not having the disease or conditions or from another appropriate control fluid: and (f) comparing the results of step (d) with the results in step (e), thereby identifying the change in the activity or amount of the components.

Alternatively, the labeling technique can be altered to examine kinetic vs. thermodynamic differences between the diseased and non-diseased states. For such an approach the steps (a) and (b) are carried out as above followed by:

(c) administering a large pulse of a radiolabeled metabolite;

(d) after an appropriate interval, stopping the reaction or adding unlabeled metabolite;

(e) isolating and identifying labeled components (labeled either under steady-state or pulse-chase conditions) in the sample;

(f) performing steps (a) to (e) with a biological fluid from a normal subject or a subject not having the disease or conditions or from another appropriate control fluid: and (g) comparing the results of step (d) with the results in step (f), thereby identifying the change in the activity or amount of the components.

Yet another alternative involves assaying growth conditions of the biological fluid containing cells by adding a combination of SAM metabolites (pathway intermediates) and/or an inhibitor thereof in a combinatorial manner.

Another method provided herein is directed to evaluating a test compound which is a small molecule which is a SAM pathway component or a component which influences a SAM pathway, and which molecule has a molecular weight preferably below 5 kDa, for its utility in a therapeutic composition or protocol for treating disease or condition associated with altered SAM metabolism. In one embodiment of this method, cells associated with the disease or condition (obtained from a subject or from a cultured cell line) are grown in a selected medium which includes one or several concentrations of the small molecule (or a combination of small molecules) being evaluated, preferably in a combinatorial manner. The impact of the small molecule on a target cellular process characteristic of the disease or condition is determined by measuring the target cellular process using any analytical method well-known in the art. Examples of target processes include: transport of molecules across the cell membrane, intracellular localization of molecules in organelles or compartments, intercellular and intracellular signalling pathways, metabolic processes, and the like. The results obtained from this determination are compared with the results obtained using the same cells grown without the added test compound or compounds. Alternatively, or additionally, the results are compared to the results obtained with normal cells (not associated with the disease or condition) grown in the presence of the same concentrations of the same test compound or compounds. Such a comparison will identify compounds which are capable of altering the target cellular process and are thereby useful in a therapeutic composition or protocol for the disease or condition. This method is particularly useful with cancer cells grown in culture.

In a different embodiment of the above method, rather than evaluating a compound's action on cells in vitro, an animal model of the disease or condition is administered the test compound or compounds in vivo. The target cellular process analyzed by obtaining a biological fluid, preferably including cells, from the animal and analyzing it as above. A comparison is made with a normal animal counterpart of the disease model. This method is particularly amenable to evaluating a compound for its utility in diabetes, various autoimmune diseases, or any genetically based metabolic disorder for which an animal model is known or becomes known in the future.

In all the above methods the disease or condition is preferably selected from the group consisting of a wound, cancer, multiple sclerosis, Alzheimer's disease, Parkinson's disease, depression and other imbalances of mental stability, atherosclerosis, cystic fibrosis, diabetes, obesity, Crohn's disease, and altered circadian rhythmicity. The invention can also be practiced with any other disease or condition not specifically listed or exemplified herein. Such diseases are described, for example, in Scriver et al (Eds), THE METABOLIC BASIS OF INHERITED DISEASE, McGraw Hill Information Services Company, New York. Volumes I and II, 1989; Graig et al., MODERN PHARMACOLOGY, 4th Edition, Little Brown and Company, Boston, 1994). Other categories of diseases amenable to the methods of the present invention include arthritis, psoriasis and other skin diseases, autoimmune diseases, allergies, hypertension, anxiety disorders, schizophrenia and other psychoses, osteoporosis, muscular dystrophy, amyotrophic lateral sclerosis and circadian rhythm-related conditions. The methods and approaches disclosed herein are in fact applicable to an exogenous or endogenous disease or metabolic alteration in any living organism, ranging from unicellular organisms to plants and higher animals. Preferred subjects for the present methods are mammals. Preferred mammals are animals of agricultural importance. Most preferred subjects are humans.

When the condition is a wound, the target metabolites preferably comprise one or more of SAM or a SAM derivative, methionine, adenosine, cysteine, homocysteine, cystathionine, choline, ethylene, biotin, biotin analogues, ACC, polyamines, queuosine, queuine and nicotinamide. For cancer the target pathways or metabolites preferably comprise one or more of methylation products of RNA, methylation products of DNA, methylation products of protein, methylation products of a small molecule, queuosine, queuin, wye-base incorporation into tRNA or effects promoted by queuine, SAM synthesis, folate and vitamin $B_{12}$ transfer of methyl groups, methionine synthesis, methylthioadenosine or its catabolic products, homoserine lactone, 5-deoxyadenosine, polyamine synthesis and catabolism, ethylene synthesis, biotin levels, hypusine synthesis on eIF-5A (formerly termed eIF4D), diphthamide synthesis on EF-2 and salvage of methylthioadenosine (specifically, adenine phosphoribosyl transferase, APRT) and the enzymes which convert the ribose moiety to methionine. When the disease is multiple sclerosis, the target pathways or metabolites preferably comprise one or more of: levels of SAM, S-adenosyl homocysteine, folate and vitamin $B_{12}$ levels in serum and cerebrospinal fluid, methyl transferase activity, myelin basic protein methylation and phosphatidylcholine levels. For Alzheimer's disease and the target pathways or metabolites preferably comprise one or more of methylation levels, SAM, biotin, polyamines, $Ca^{2+}$/calmodulin methylation and levels, folate, vitamin $B_{12}$, ubiquinone and alternative splicing of mRNA for β-amyloid protein. For Parkinson's disease, the target pathways or metabolites preferably comprise one or more of polyamines, nonspecific N-methylase, acetyl-L-carnitine, $Ca^{2+}$/calmodulin-dependent protein kinase II, lysolecithin, sphingomyelin, SAM and vitamin $B_{12}$. When the disease is atherosclerosis, the target pathways or metabolites preferably comprise one more of methylation levels, homocysteine and its catabolites, polyamines, acetyl-L-carnitine, calmodulin, and essential phospholipids. For cystic fibrosis the target pathways or metabolites preferably comprise one or more of calmodulin, polyamine levels, polyunsaturated fatty acids, total saturated and monounsaturated fatty acids and the cystic fibrosis transmembrane conductance regulator. When the condition is obesity the target pathways or metabolites preferably comprise one or more of methylation levels, serotonin, calmodulin, carnitine and ubiquinone.

The present invention is further directed to a method of treating a subject having a disease or undesired condition associated with altered SAM metabolism, comprising administering a therapeutic composition or protocol identified by the method described above to the subject, with the proviso that the therapeutic composition or protocol is one which has not been previously identified as being useful for treating the disease or condition.

The present invention is directed to a therapeutic composition or protocol identified by the above method, with the above proviso. The therapeutic composition or protocol is preferably one which is used to treat a disease or condition is selected from the group consisting of (but not limited to) a wound, cancer (including leukemias and lymphomas), multiple sclerosis, Alzheimer's disease, Parkinson's disease, amyotrophic lateral sclerosis, depression or other mental instabilities, atherosclerosis, cystic fibrosis, diabetes, obesity, arthritis, autoimmune diseases (such as Crohn's disease), arthritis, psoriasis, allergies, hypertension, osteoporosis, cystic fibrosis, and altered circadian rhythmicity.

In one embodiment, the above therapeutic composition is for treating a wound and comprises adenosine, methionine, 1-amino-cyclopropane-1-carboxylic acid, biotin and nicotinamide in amounts effective for treating the wound.

Also provided is a pharmaceutical composition useful in treating a disease or undesired condition in a subject, which comprises an effective amount of the above therapeutic composition and a pharmaceutically acceptable excipient, optionally in combination with one or more additional agents useful for treating the disease or condition. A preferred pharmaceutical composition for treating a wound comprises adenosine, methionine, 1-amino-cyclopropane-1-carboxylic acid, biotin and nicotinamide.

The invention provides a method to treat a disease or undesired condition associated with altered SAM metabolism in a subject, which comprises administering to the subject a therapeutic composition or protocol or a pharmaceutical composition, as above.

The present invention further is directed to a method to characterize a disease or undesired condition, or to characterize the progress of the disease or condition, which disease or condition is associated with altered SAM metabolism, the method comprising:
  (a) identifying one or more metabolic pathways associated with the disease or condition which metabolic pathway is a SAM pathway or is influenced by a SAM pathway or a metabolite of a SAM pathway;
  (b) determining which of the one or more metabolic pathways identified in (a) is altered from normal in the presence of the disease or condition and which pathway changes in response to the progression thereof;
  (c) measuring the activity, amount or association with other proteins, of selected enzymes or metabolites of the one or more pathways determined in step (b) as a function of time after onset of, or diagnosis of, the disease or condition, to obtain a metabolic data set;
  (d) recording clinical manifestations of the progression of the disease or condition to obtain a clinical data set
  (e) comparing the metabolic data set with the clinical data set to obtain a combined data set,
wherein the metabolic, clinical or combined data sets characterize the disease or condition, or characterize the progression thereof Any of the above data sets may be converted to digital computer-readable form.

Also provided is an electronically retrievable profile characterizing a disease or undesired condition or the progression thereof, which disease or condition is associated with altered SAM metabolism, which profile is obtained by the above method.

Also included is a method for identifying or measuring a change in the activity, amount or association with another protein, of (i) a component of a SAM pathway or (ii) a component of a metabolic pathway which is influenced by a SAM pathway, in a subject having a disease or undesired condition associated with altered SAM metabolism, which method comprises:
  (a) obtaining a biological fluid from a subject having the disease or condition;
  (b) contacting the fluid with an affinity matrix to which is immobilized at least one first affinity ligand, which ligand (or ligands) binds to an enzyme or metabolite of a SAM pathway, and allowing material in the fluid to bind to the ligand;

(c) removing any material of the fluid not bound to the ligand;

(d) eluting material bound to the ligand from the affinity matrix to produce a first eluate, in a single fraction or as sequential fractions eluted with increasing salt concentrations or with different competitive ligands;

(e) identifying the presence or measuring the amount of any previously bound and subsequently eluted material in the first eluate;

(f) performing steps (a)–(e) with a biological fluid from a normal subject not having the disease or condition; and (g) comparing the results of step (e) with the results of step (f), thereby identifying or measuring the change in the activity, amount or association of the components.

The above method may comprise the additional steps, prior to step (e), of (h) contacting the first eluate of step (d) with a second affinity matrix to which is affixed at least one second affinity ligand different from the first affinity ligand, which second ligand binds an enzyme or metabolite of a SAM pathway, and allowing material in the eluate to bind to the second ligand;

(i) removing any material of the first eluate not bound to the second ligand of step (h);

(j) eluting any material bound to the second ligand from the affinity support, thereby producing a second eluate;

(k) identifying the presence or measuring the amount of any previously bound and subsequently eluted material in the second eluate;

(l) performing steps (a)–(e) and (h)–(k) with a biological fluid from a normal subject not having the disease or condition; and (m) comparing the results of step (l) with the results of step (k), thereby identifying or measuring the change in the activity, amount or association, of the components.

Also provide herein is a method for identifying or measuring a change in the activity or amount of (i) a component of a SAM pathway or (ii) a component of a metabolic pathway which is influenced by a SAM pathway, in a subject having a disease or undesired condition associated with altered SAM metabolism, which method comprises:

(a) obtaining a biological fluid from a subject having the disease or condition;

(b) contacting the fluid with a detectably labeled compound selected from the group consisting of SAM, a SAM pathway metabolite other than SAM and a molecule which indirectly affects a SAM pathway, thereby allowing the detectable label to be donated to any other molecule in a SAM pathway or a pathway influenced by a SAM pathway, thereby resulting in labeled products in the fluid;

(c) identifying the presence of, or measuring the amount of, any of the labeled products;

(d) performing steps (a)–(c) with a biological fluid from a normal subject not having the disease or condition; and (e) comparing the results of step (e) with the results of step (f), thereby identifying or measuring the change in the activity, amount or association of the components.

In the above method, the subject may be a non-human animal model of the disease or condition.

Another method involves determining the concentration of intermediates of the SAM pathways in biological fluids including any types of clinically relevant samples. This method, which may be used alone or in combination with the methods described above, includes the steps of:

(a) obtaining a biological fluid from a subject having the disease or condition;

(b) determining the concentration of SAM and/or SAM pathway intermediates and/or molecules influenced by SAM and/or SAM pathway intermediates. These concentrations can be determine by any or a number of methods known in the art of which HPLC is preferred. The metabolites or intermediates may include, SAM, methionine, SAH, 5'-deoxyadenosine, 5'-methylthioadenosine, dcSAM, putrescine, spermine, spermidine, derivatized forms of these polyamines such as acetyl spermine, acetyl spermidine or glutathione-conjugated spermidine, homocysteine, cAMP, cGMP, adenosine, inosine, homoserine lactone, queuine, queuosine, wye-base, etc.

(c) performing step b) with a biological fluid from a normal subject not having the disease or conditions: and (d) comparing the results of step b) with the results in step c) thereby identifying the change in the activity or amount of the components.

From the data generated above with these methods, both pharmaceuticals and diagnostic products can be developed. In some instances in a diseased state, abnormal metabolism may be suspected which involves binding of proteins or enzymes to the cytoskeleton. In such a case, a preferred approach employs cytoskeletal molecules, e.g., actin or tubulin, immobilized to an affinity matrix. This affinity matrix is then used to examine a biological fluid from a diseased and non-diseased state for interaction of SAM and SAM-intermediates with the affinity matrix or with cell components previously bound to the affinity matrix. This information is then used to developed pharmaceuticals or diagnostic products.

Diagnostic Products

The presence or absence of any component (SAM pathway or intermediate) in the disease state or, alternatively, a large difference in any component between the normal and disease state, will lead to the development of a diagnostic assay by methods known in the art. As an example an antibody can be developed against the targeted SAM pathway component by standard procedures known in the art. This antibody can be used in an immunoassay, preferably an solution-based enzyme inmmunoassay (EIA) which may be measured by colorimetry, fluorescence or chemiluminescence. Alternatively, an in situ assays or a dipstick-based assay may be preferred.

In situations wherein the concentrations of the components being measured is at an appropriate detectable level, direct assays may be used, for example colorimetric, fluorometric chemiluminescent, HPLC, gas chromatographic, etc.

Therapeutic Products

When the concentration of one or more SAM pathway intermediates is found to be aberrant in a disease state, the condition is treated by administering the appropriate SAM intermediate or intermediates to the subject. Alternatively, the condition is treated by inhibition of stimulation of the particular SAM pathway or pathways. For example, the SAM/SAH ratio can be decreased by the use of SAH hydrolase inhibitors (Wolfe et al., *J. Med. Chem.* 34:1521–1530 (1991)) or adenosine deaminase inhibitors. Similarly, the use of the polyamine antagonist DL-α-difluoromethylornithine, can increase SAM concentrations as much as 48-fold (Bacchi et al., In: *Parasitic Protozoa and Polyamines in Inhibition of Polyamine Metabolism*, McCann, P. P. et al., eds., Academic Press, New York, pp 317–344 (1987)).

Aberrant Binding of a Ligand to a Target Molecule in a Disease State

In some disease states, a ligand such as a protein, nucleic acid, lipid, sugar, or other molecule may bind abnormally to a target molecule. In these cases, displacement of the ligand from its target may improve the subject's condition and ameliorate the disease. An assay, preferably in microtiter plate format, that measures the ligand having the undesired binding, is used according to procedures known in the art as a screening assay to develop active compounds. Particularly preferred is the use of a screening assay in combination with combinatorial drug discovery procedures (see for example, Desai et al., *Drug Devel Res*. 33:174–188 (1994); Jacobs et al., *Trends in Biotech*. 12:19–26 (1994)) to develop active compounds. Similarly a therapeutic approach may involve decreasing or increasing the activity of one or more enzymes. Thus, enzyme inhibitors or activators may be developed with the use of the appropriate screening assay and combinatorial drug discovery approach.

Figure 1:
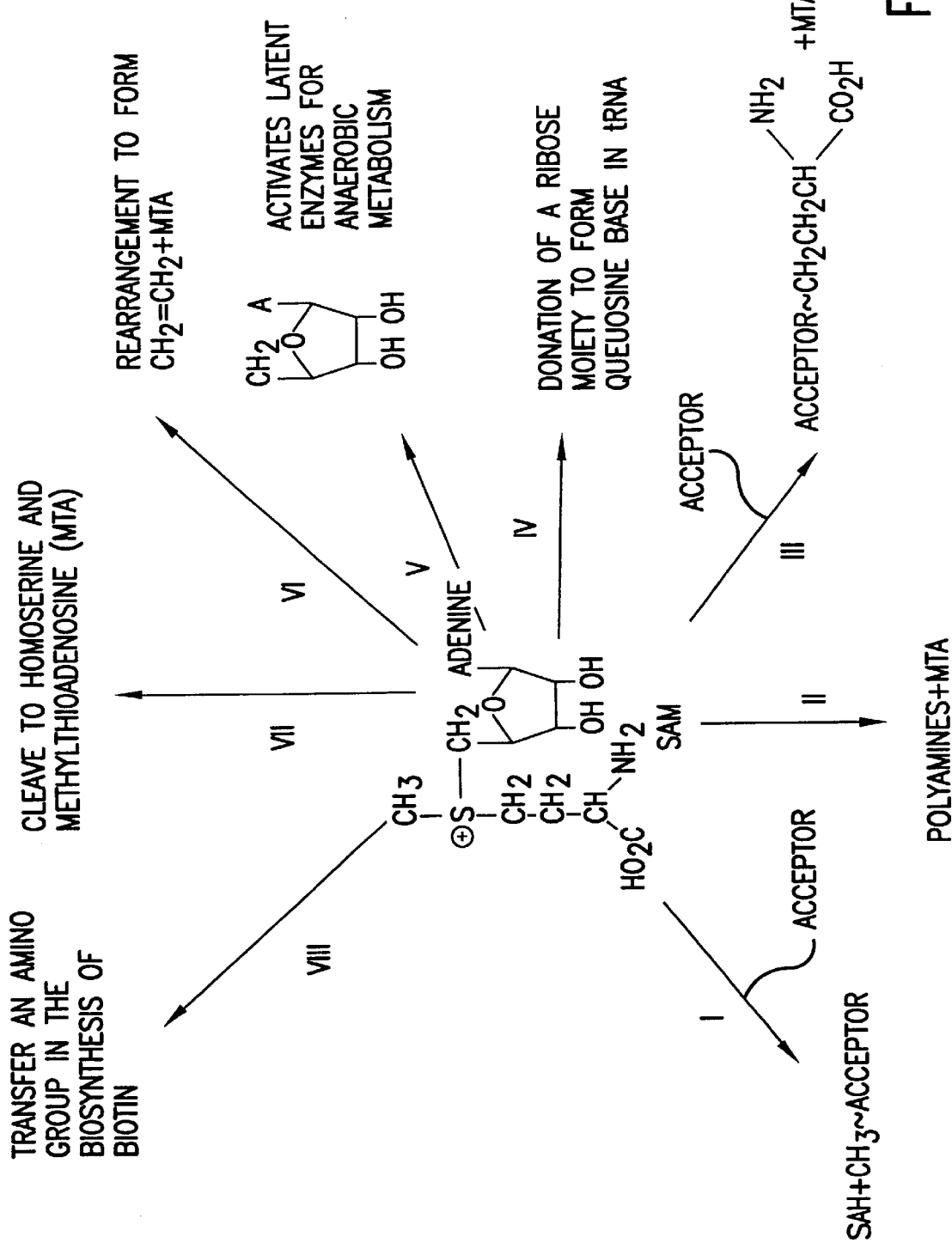
FIG. 1 shows an overview of the eight known metabolic pathways resulting from reactions and degradation of SAM. The eight SAM pathways are numbered I–VII. These pathways are described in more detail in FIGS. 2–9.

1. N-5-methyltetrahydrofolate:homocysteine methyltransferase; 2. methylenetetrahydrofolate reductase; 3. betaine:homocysteine methyltransferase; 4. serine hydroxyacetyl transferase; 5. cystathione β-synthase; 6. S-adenosylmethionine synthetase; 7. Series of reactions involved in polyamine synthesis; 8. various methyltransferases; 9. S-adenosyl homocysteine hydrolase

DESCRIPTION OF THE PREFERRED EMBODIMENTS

Definitions

"SAM Metabolite" or "Degradation Product of SAM"

Any catabolite or anabolite of SAM. This term includes any moiety cleaved from SAM (e.g., ethylene), or any moiety donated by SAM to an acceptor molecule, the resulting product of such a donation or the residual product remaining after the donation reaction. The donated moiety as well as the resulting products formed by combining with an appropriate acceptor is said to have metabolic regulatory function. Any product which results from such combining is therefore included within the scope of this definition. Also included within this definition is any cofactor (defined below) which binds to or associates with any component of a SAM pathway as defined below.

"SAM Pathway" or "SAM Metabolic Pathway":

Any of the eight pathways described in more detail below, including all enzymes, cofactors and SAM metabolites present in these pathways. This term includes, for example, the proteins whose activities are affected by the protein calmodulin, which is itself a primary target for methylation (at $Lys^{115}$ and its C-terminus). A list of such proteins is presented in Table III. Also included in this definition are additional pathways, currently known or yet undiscovered, in which SAM is a component. This definition also includes any additional metabolic pathway influenced by SAM or a SAM metabolite.

"Biological Fluid":

Any fluid derived from the body of a normal or diseased subject, including but not limited to blood, serum, plasma, lymph, biopsied cells or tissue, urine, saliva, tears, cerebrospinal fluid, milk, amniotic fluid, bile, semen, ascites fluid, wound fluid pus and the like. The term includes any cells present in such fluid. Also included within the meaning of this term is an extract of a tissue or cells or any fraction of such an extract, for example, a subcellular fraction of cytosol or membranes or nuclear material, etc. The term also encompasses culture fluid containing cells or in which any cells or any tissue preparation have been incubated.

"Small Molecule"

A biochemical entity which is not a macromolecule, generally having a molecule weight of less than 1000 daltons. Molecules having molecular weights between 1000 and 5000 may also be considered "small molecules" as intended herein. The term generally is used herein to refer to a SAM metabolite or an analogue or derivative thereof "Cofactor":

The non-proteinaceous small molecule associated either covalently or non-covalently with a protein. Examples are organic and organometaffic prosthetic groups, such as many vitamins, which associate with an apoenzyyme to form a functional holoenzyme (Smith, E. L. et al., *PRINCIPLES*

OF BIOCHEMISTRY, General Aspects, 7th Ed., McGraw-Hill Book Co., New York, 1983, p. 184).

The RNA World and SAM

Application of the methods of this invention requires a comprehensive understanding of the role of RNA and the metabolic pathways controlled by SAM and their impact on RNA both in the development of life as well as in the biochemical processes of the living cell and organism. This invention germinated in part from the present inventors' understanding that the origin of life was driven by replication of RNA. Natural selection operated initially only for replication, and energy was not of any concern. In present-day life, viruses operate in this way. SAM also drove the origin of life by initially modifying RNA, thereby causing an exponential increase in the number of sequence permutations in any given length of sequence. Chemical evolution initially produced a "prebiotic soup" (Oparin, A. L., *Orig. Life* 7:3–8 (1976); Oparin, A. L., *Adv. Enzymol.* 27:347–380 (1965); Schlesinger, G. et al., *J. Mol. Evol.* 19:376–82 (1983); Schlesinger, G. et al., *J. Mol. Evol.* 19:383–390 (1983). As RNA began to replicate on a massive scale using SAM modification for regulatory control, both RNA nucleotides and SAM were depleted from the prebiotic soup and the replicating progenote began to "starve". This led to stepwise reverse evolution which established the "universal metabolic pathways" found in present-day life (Horowitz, N. H., *Proc. Natl. Acad. Sci. USA* 31:153–157 (1945).

For each biochemical pathway, reverse evolution led eventually to a compound which was the precursor of another pathway. In this way, the biochemical pathways of life became connected. With the merging of pathways, a metabolic complexity arose that allowed evolution to become divergent. This led to the present state of biochemical pathways wherein some are universal but many are not.

Cofactors (defined above) predated proteins and were synthesized from simple reactions, often involving nucleotides. Some organic cofactors act as acceptors or donors of atoms or of functional groups that are removed from or added to the substrate of the enzyme. Such cofactors are commonly referred to as coenzymes. In present-day biochemistry, cofactors carry out the actual chemistry of many enzymes. However, such cofactor-mediated reactions do not have the speed or specificity of protein:cofactor complexes. At the beginning of life, however, speed was not essential and specificity was not desirable, given the presumed advantages of available cofactors which could carry out chemical transformations on a number of different molecules. As life progressed, however, those progenotes which could increase their rate of replication acquired a selective advantage. This created selective pressure for the evolution of a protein scaffold which would provide the cofactor with reaction speed and specificity, and sites for regulatory control.

As life evolved, there was a need to develop methods for chemical synthesis using one-carbon compounds. Natural selection thus occurred for the addition of one carbon compounds (e.g., the formyl group) as building blocks for a small number of molecules used in biosynthesis. The system that arose was the tetrahydrofolic acid system which can carry five types of one carbon groups. Another major need at the beginning of life was to assimilate $CO_2$ and fix it into molecules. This was achieved by the evolution of biotin, a prosthetic group which was essential to the genesis of life since it connects several of the universal metabolic pathways. As described below, the synthesis of biotin is controlled by a switch mechanism involving a SAM-mediated transamination of a biotin precursor.

As life progressed, the evolution of more complex progenotes became limited by the inherent instability of RNA. The solution to this problem was provided by the evolution of DNA which was much more stable. However, the regulatory rules of life would have first been written into RNA through the donor/cleavage pathways of SAM. Since evolution is conservative, it follows that the initial rules of life would have remained in RNA rather than being transferred to DNA.

The earth's atmosphere during the genesis of life (ca 3.7 billion years ago) was composed largely of methane, ammonia, hydrogen and water and contained essentially no molecular oxygen. As a result, life arose in the absence of $O_2$, and the initial biochemical pathways evolved in an anaerobic environment. After about 1.9 billion years, the first photosynthesizing ($O_2$-producing) microorganisms evolved, leading to the generation of an oxygen-rich atmosphere over a period of about 0.5 billion years. For life, the introduction of $O_2$ into the atmosphere was momentous since $O_2$ is highly reactive and readily oxidizes many molecules. Thus only highly specialized microbes could survive its oxidizing effects. This created a selective pressure for the evolution of facultative microbes that could live in either an anaerobic or aerobic environment. Such microbes accomplished this by developing a metabolic switch that allowed them to survive either in the absence or the presence of $O_2$. As will be noted below, the chosen metabolic switch occurs through use of a SAM pathway that produces a free radical of 5'-deoxyadenosine. This switch is not limited to microbes. It may be present in humans and is considered by the present inventors to be a component in normal cellular development and in the etiology of many disease states.

As the cell evolved, SAM regulated virtually all of its activities by modification of a variety of molecules, including RNA, DNA, proteins, small molecules and lipids. This control was exerted first at the intracellular level and regulated key cellular states. Later, however, this SAM-mediated intracellular control evolved to extracellular control which included regulation between cells, tissues and organs. Hence, nature used its SAM regulatory system as life evolved from simple cells to the most complex organisms. For example, SAM controls virtually all body functions in man beginning with sugar metabolism and fatty acid metabolism and extending to the immune system and even mental stability, through SAM-mediated modification of a number of critical neurotransmitters and hormones. Not surprisingly, SAM also controls aging of the organism. Hence, virtually all diseases and/or disorders associated with aging, such as diabetes, atherosclerosis, arthritis and Alzheimer's disease, are caused, in part, by abnormal perturbations of the SAM pathways.

Below is presented a detailed picture of eight SAM pathways. SAM is a sulfonium ion and, as such, can donate a number of different groups to the appropriate acceptor molecule. The driving force for each SAM reaction is the conversion of the unstable positively-charged sulfonium derivative to a stable uncharged sulfur (thioether) derivative. For the purposes of simplicity, regulation in eukaryotic cells is emphasized. The present invention is directed in particular to methods and compositions useful for eukaryotic organisms, preferably mammals, most preferably humans. To the extent that the metabolic pathways of prokaryotes impact on the metabolic state of a eukaryotic organism, such as in infectious diseases, the present invention includes the determination of the contribution of the prokaryotic metabolic pathways.

SAM is formed by the reaction of methionine with ATP, which creates an activated methyl group by virtue of the sulfonium ion contained in SAM. The activated status resulting from the presence of a sulfonium ion can be most readily reversed by demethylation through transfer of the methyl group from SAM to an acceptor; however, as shown in FIG. 1, a number of alternative routes, all of them important in regulating metabolism, effect the same result. The eight SAM pathways, designated "SAM Pathway No. 1" through "SAM Pathway No. 8" are described below. These pathways have been arbitrarily numbered. This list of pathways is not exhaustive, as SAM may be known to, or may be discovered to, participate in additional pathways which are considered within the scope of the present invention. For example, azetidine 2-carboxylic acid, known to be formed from labeled [1-$^{14}$C]-methionine (Leete, *Phytochemistry* 14:1983–1984 (1975)), may be derived from SAM.

SAM Pathway No. 1: Modification with the Methyl Group

Figure 2:
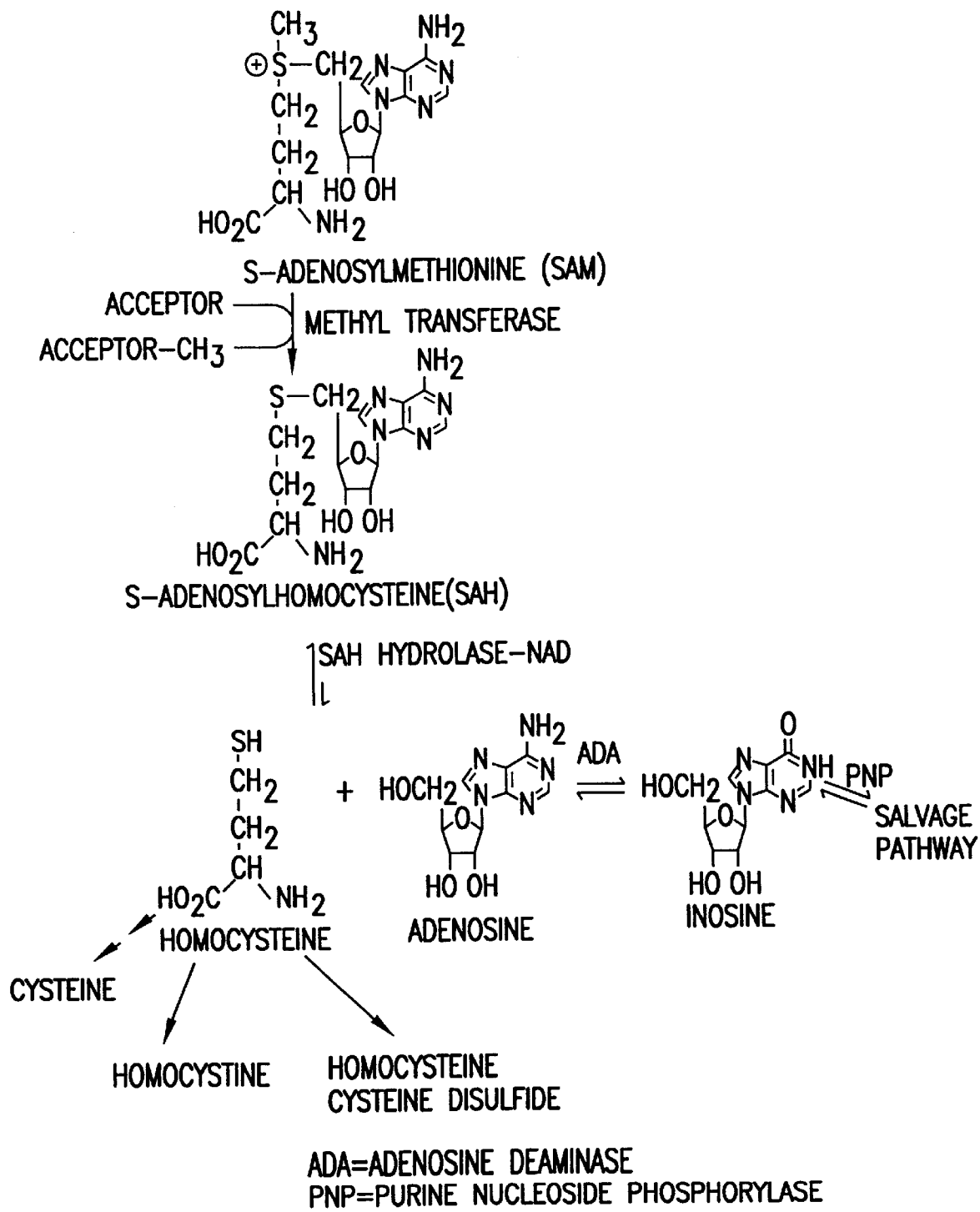
FIG. 2 is a schematic illustration of SAM Pathway No. 1 leading to SAH, homocysteine and purines.

As shown in FIG. 2, SAM Pathway No. 1, results in the donation of a methyl group to any of a large number of acceptors such as RNA, DNA, a protein or a small molecule. SAM-mediated methylation of RNA provides key elements in the master regulatory control of the eukaryotic cell. Indeed, the most heavily methylated molecules are the various RNAs (mRNA, snRNA, tRNA, ribosomal RNA, etc.). More than 60 different modifications of RNA due to donation of methyl groups are known. DNA methylation is largely restricted to the single m$^5$C modification in eukaryotes (and to m$^5$C and m$^6$A in prokaryotes). More than 30 modifications to regulatory proteins are known. A small group of proteins are methylated, which are known to have critical regulatory functions in the eukaryotic cell, including G proteins such as ras protein, calmodulin, histones, ribosomal proteins. The methylations can be reversible or irreversible, depending on the type of modification and the protein.

A select group of small molecules also methylated in the cell are those which are active in neurotaansmission and metabolism. These classes of molecules, among some of the most important regulatory molecules of life, are used in both intracellular communication, for example, regulation of fatty acid oxidation by carnitine (through transport into the mitochondria on the carnitine shuttle) and in extracellular communication, for example the neurotransmitters acetylcholine, epinephrine and norepinephrine.

The methylation of nucleic acids, proteins, and small molecules provides the primary mechanism by which SAM regulates the cell. It is through this mechanism, in part, that the immune system is modulated and the anti-viral and anti-cancer effects of the interferons are effected. It also is primarily through methylation that the aging process is regulated by several highly specific chemical mechanisms.

In addition to providing methyl groups (which have profound effects on the acceptor per se) the donation of a methyl group by SAM generates S-adenosylhomocysteine (SAH), a compound whose levels, in part, control the levels of SAM since it acts as a differential inhibitor of SAM-mediated methylations. The level of SAH is in turn affected by the levels of its own degradation products, homocysteine and adenosine. These products result from the activity of SAH hydrolase, which uses NAD$^+$ as a cofactor and which also catalyzes the reverse reaction of adenosine and homocysteine to form SAH as shown. The level of adenosine is in turn an equilibrium function of the balance between adenosine and inosine, a conversion catalyzed by adenosine deaminase (ADA). The level of inosine is regulated by purine nucleoside phosphorylase which converts inosine to ribose-1-phosphate and hypoxanthine.

Thus, by manipulating the levels of the products of this pathway, the levels of SAM, and thereby the levels of alternative degradation products of SAM, such as SAH, can be controlled. Residual SAH controls the manner in which methylation is distributed. Methylations generally are catalyzed by methyl transferases; at low SAH concentrations, these methyl transferases generally have maximal activity. However, SAH inhibits these activities differentially so that at higher SAH concentrations the activities of some methyl transferases are diminished relative to others. Thus, at one level, the concentration of SAH controls the pattern of methylation.

It will be evident that one important point of control will therefore reside in controlling the levels of SAH. The opportunities for doing so are numerous. As described above, SAH is formed either by the decomposition of SAM or by the action of SAH hydrolase in the presence of homocysteine and adenosine. Control of the levels of any of these components results in an effect on the levels of SAH. In addition, compounds which affect the activity of SAH hydrolase itself will exert relevant metabolic effects, for example nicotinamide adenine dinucleotide (NAD$^+$) and cyclic AMP (cAMP). As noted above, SAH hydrolase has an absolute requirement for NAD$^+$. SAH hydrolase is one of the three major cAMP binding proteins known in eukaryotic cells. (The others are phosphofructokinase and glyceraldehyde-3'-phosphate dehydrogenase). It is considered highly significant by the present inventors that cAMP reversibly inactivates SAH hydrolase from the lower eukaryote Dictyostelium discoidium (Hohman et al., Arch. Biochem. Biophys. 233:785–795 (1984). In the view of the present inventors, such cAMP-mediated regulation of SAH hydrolase is expected to exist in higher eukaryotes.

The levels of homocysteine and adenosine are in part controlled by their degradation pathways. Homocysteine in the presence of methylcobalamin undergoes methylation to form methionine and de-methylated cobalamin. Homocysteine is also converted by condensation with serine to form cystathionine which is then cleaved to produce 2-ketobutyrate and cysteine, a result having implications for the redox status of the cell in view of the role of cysteine in redox and its incorporation into glutathione. Adenosine is converted to inosine by ADA and thence to hypoxanthine and ribose-1-phosphate by purine nucleoside phosphorylase.

The effects of ADA enzyme deficiency are dramatic. Absence of ADA activity results in severe immunological deficiency ("the boy in the bubble syndrome"). These persons have high levels of adenosine and thus of SAH. In addition, these persons have high levels of 2'-deoxyadenosine which is also salvaged under normal conditions by ADA, and which has been shown to be an irreversible suicide inhibitor of SAH hydrolase. High SAH levels play a central role in modulating the differentiation of the B and T lymphocytes, in part due to the influence of SAH on methylation of mRNA targets which are implicated in alternative splicing.

An alternative method of controlling SAH hydrolase activity is through the, concentration of methylthioadenosine (MTA) which is a suicide inhibitor of SAH hydrolase, this molecule is produced in four of the eight SAM pathways, namely SAM Pathways No. 2, 3, 6 and 7 (all indicated in FIG. 1). Thus, the activity of SAH hydrolase and the levels of SAH can be indirectly controlled by the MTA produced in these pathways.

Another means to control SAH levels involves activation of methyl transferases that generate SAH and which themselves are not significantly inhibited by high levels of SAH. These include glycine N-methyl transferase (the activity of which has been shown to increase linearly with aging in a rat model for aging) and nicotinamide N-methyl transferase which methylates nicotinamide generated in high levels by poly(ADP-ribosylation) occurring in the nucleus. In the case of methylation by glycine N-methyl transferase, the product, sarcosine, mediates the transfer of the methyl group into the folate system which will ultimately generate additional methionine and hence additional levels of SAM.

Another approach to control of SAH levels is exemplified by the action of interferon-γ which leads to an increase in the levels of certain specific markers including the activity of indoleamine 2,3-dioxygenase, xanthine oxidase, and GTP cyclohydrolase as well as the levels of three small molecules, neopterin, tetrahydrobiopterin and kynurenine. Tryptophan and guanosine triphosphate levels, however, decrease. This pattern is consistent with enhanced breakdown of tryptophan which results in the production of at least three products that inhibit SAH hydrolase: picolinic acid, quinolinic acid and nicotinamide. These three compounds also inhibit mono(ADP-ribosyl)ase and poly(ADP-ribosyl)ase. In particular, poly(ADP-ribosyl)ase uses $NAD^+$ as a substrate and produces poly(ADP-ribosyl)ated protein and stoichiometric amounts of nicotinamide. The produced nicotinamide inhibits SAH hydrolase, which thus increases SAH levels. Alternatively, nicotinamide can be methylated which also increases SAH levels. The activities of the ADP-ribosylases also have direct and important effects on cellular metabolism.

Alternatively, methylation reactions in general can be directly inhibited by a pyridinium compound termed "pyridinoline" which is produced in vivo as a collagen crosslink following hydroxylation of lysine by lysine hydroxylase. Breakdown of collagen releases pyridinoline, thus inhibiting essential methylation reactions. The production of pyridinoline may be a natural mechanism through which the extracellular matrix communicates with nearby cells by differential inhibition of cellular methyl transferases. Aging is correlated with a decrease in methylation in general as well as an increase in collagen crosslinks. Thus, regulation can be achieved by administering pyridinoline as a small molecule or by effecting the breakdown of collagen intracellularly.

In addition, methylation pathways can be inhibited by interfering with the production of SAM; certain agents are known to be effective in such inhibition, including methotrexate which inhibits dihydrofolate reductase which ultimately prevents the transfer of the methyl group from the folate system to vitamin $B_{12}$ and then to homocysteine to obtain methionine.

In a more subtle approach, modulators of methyl transferase activity can be derived from alternative SAM pathways. For instance, SAM Pathway No. 2 generates polyamines which regulate SAM-mediated methylation (since depletion of polyamines inhibits methylation and addition of polyamines restores it). Further, biotin (formed in SAM Pathway No. 8) appears to regulate methylation, since in rabbits with biotin deficiencies, methyl transferase activity is inhibited but is restored upon addition of biotin to the diet.

Figure 3:
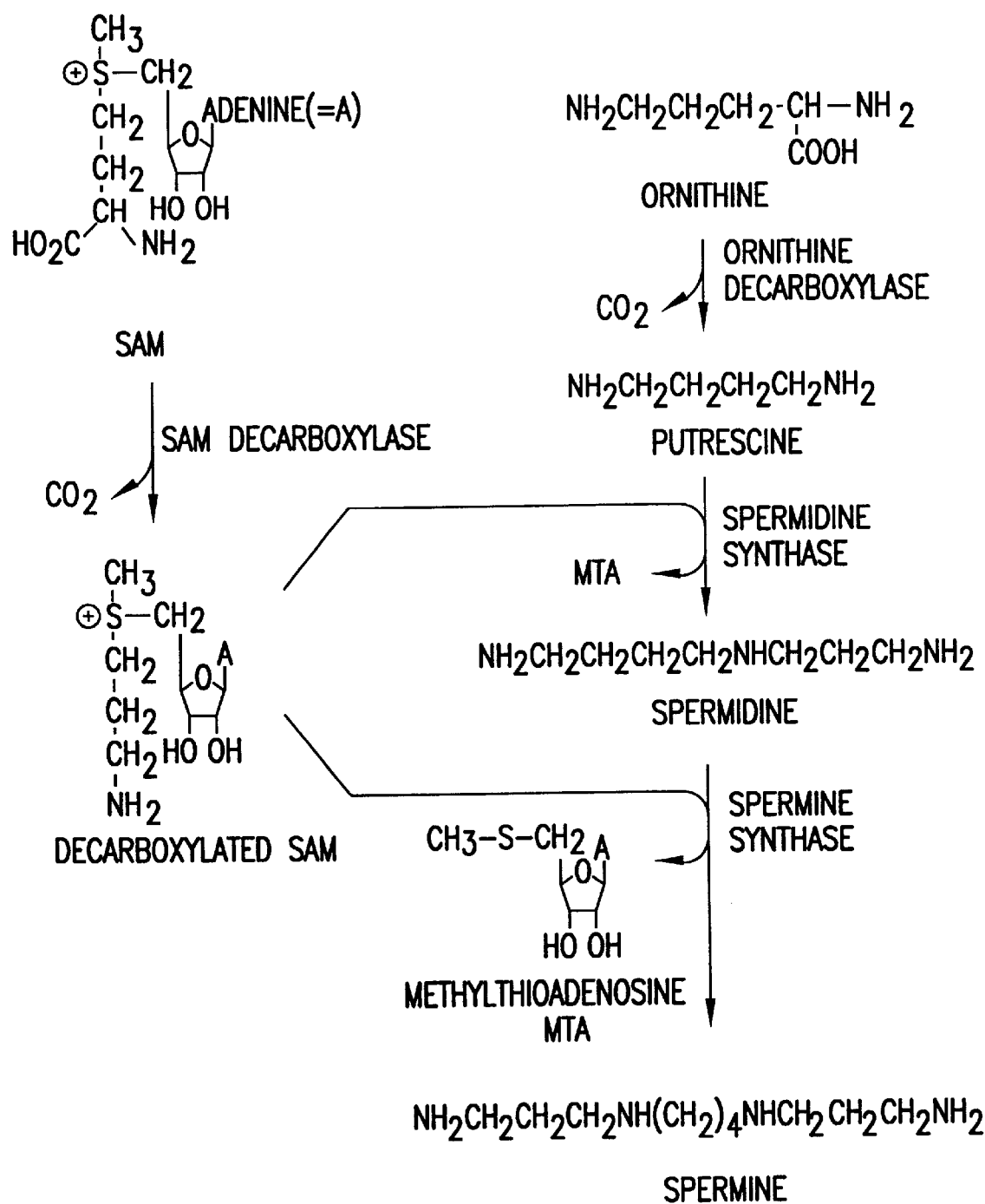
FIG. 3 is a schematic illustration of SAM Pathway No. 2 leading to polyamines.

SAM Pathway No. 2: Modification with the 3-Aminopropyl Group and Formation of Polyamines SAM Pathway No. 2, shown in more detail in FIG. 3, results from preliminary decarboxylation of SAM to decarboxylated SAM or [5'-[S-(2-aminoethyl)S-methyl] deoxyadenosine] and subsequent donation of a 3-aminopropyl group to putrescine. This results in conversion of putrescine to spermidine and then to spermine through donation of a second 3-aminopropyl group. The concentration of spermidine and/or spermine regulates virtually all major processes of the cell, including chromatin structure, DNA recombination, DNA replication, transcription, RNA processing and transport, formation of ribosomes, formation of aminoacyl tRNA, binding of aminoacyl tRNA to ribosomes, translation and readthrough of stop codons. The polyamines appear to alter shapes and functions of collections of molecules in neighboring microenvironments, including nucleic acids, proteins, and membranes. For example, the transformation and binding of the progesterone receptor and estrogen receptor to DNA is modulated by polyamines. Endocytosis through coated pits requires protein crosslinking through the action of tranglutaminases. Polyamines modulate this activity by producing (at high concentrations) mono-adducts which prevent crosslinking.

As noted above, the levels of these amines are significant in controlling the level of methylation, as is the level of MTA which is the side product of these reactions. The known salvage mechanism of MTA permits regeneration of methionine and thus additional SAM levels. The polyamines are also used in a very small number of modification reactions of proteins. For example, a spermidine modification of eukaryotic initiation factor 5A (eIF-5A) coincides with proliferation of the eukaryotic cell and therefore is likely a key event in triggering cell growth. This spermidine modifies a specific lysine in eIF-5A to form the hypusine derivative, which is currently known to occur only once in nature. In addition, under anaerobic conditions in prokaryotic cells, a substantial amount of spermidine-glutathione adduct is found. Thus, spermidine may modulate the redox state of the cell through covalent attachment with glutathione, a key cellular reducing agent.

The importance of SAM Pathway No. 2 to the process of regulating cell metabolism is suggested by the elevation of levels of SAM decarboxylase and ornithine decarboxylase (ORD) when eukaryotic cells are stimulated to divide. ORD is involved in the generation of putrescine through the decarboxylation of ornithine. Both of these decarboxylases have extremely short half-lives, as does spermidine/spermine acetylase which catalyzes reconversion of spermine to spermidine and spermidine to putrescine. This reconversion of acetylated polyamine has secondary effects thorough polyamine oxidase-mediated generation of peroxide.

The means to control these enzymes are therefore effective in controlling cellular metabolism in general, especially in view of the possible importance of ORD in the RNA polymerase-1 complex.

SAM Pathway No. 3: Modification with the 3-amino-3-carboxypropvl Group

Figure 4:
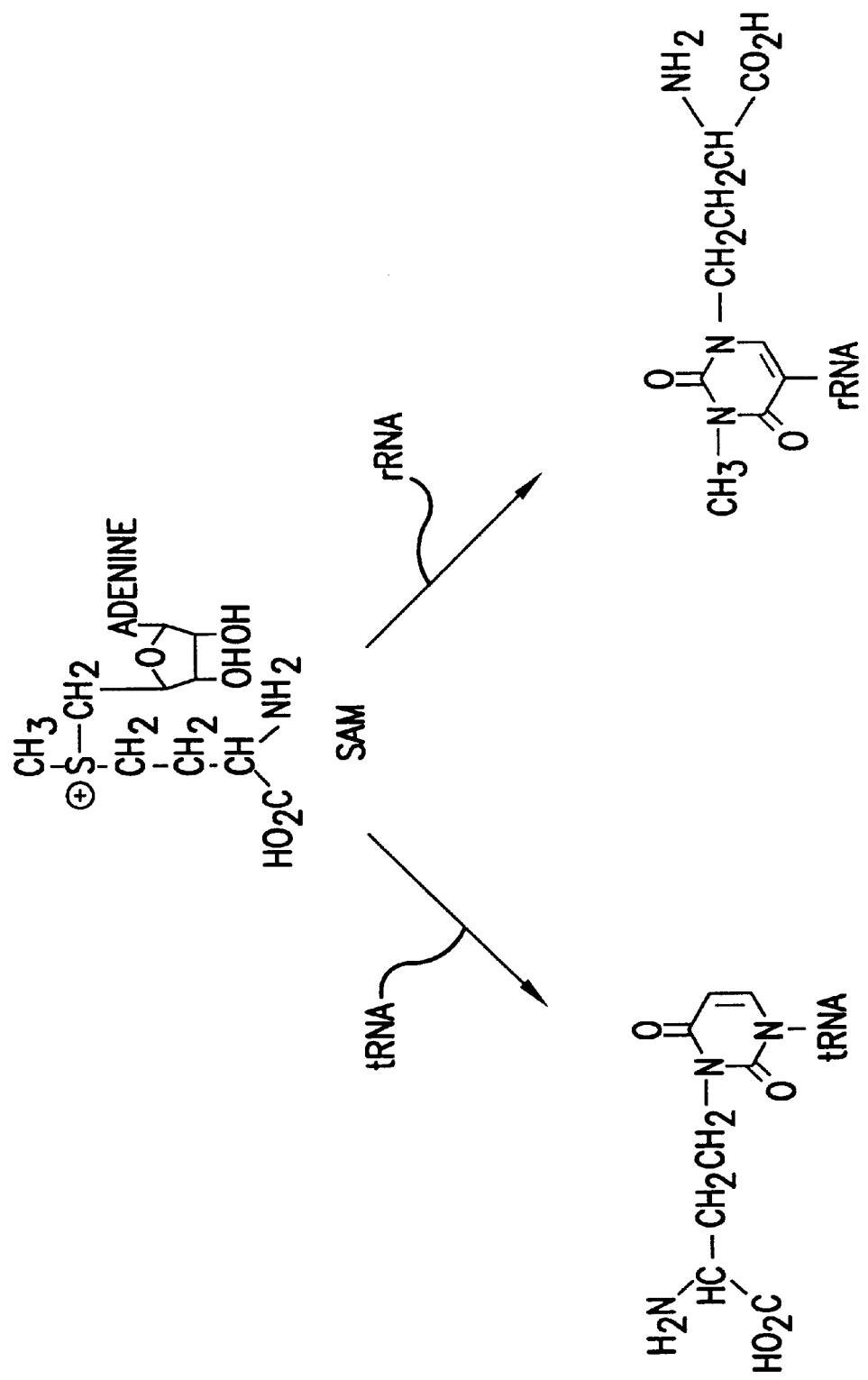
FIG. 4 is a schematic illustration of SAM Pathway No. 3 leading to modified RNAs.

SAM Pathway No. 3, and shown in more detail in FIG. 4, results in the donation of a 3-amino-3-carboxypropyl group from SAM to an appropriate acceptor, acting as an on/off switch for specific biological functions. One such acceptor is a single pseudouridine residue in one of the most conserved regions of eukaryotic 18S rRNA. This modified pseudouridine is also methylated by SAM Pathway No. 1 to form 1-methyl-3-S-(α-amino-α-carboxypropyl) pseudouridine.

The group is donated (in *E. coli*) to at least four different tRNAs at the small loop region between the anticodon loop and the D loop to produce a modified nucleotide at the $N^3$ position of uracil. The modified residue, X, is within the invariant sequence M⁷GXC in tRNA$^{Phe}$, tRNA$^{Lys}$, tRNA$^{Arg}$, tRNA$^{Val}$ and tRNA$^{Met}$. In the tRNA$^{Met}$ used for initiation of protein synthesis, X does not appear in the extra arm.

The hypermodified wye base in tRNA$^{phe}$ is also formed by this donation adjacent to the 3' side of the anticodon at the cardinal position. The donation of the 3-amino-3carboxypropyl group is followed by formation of the methyl ester and subsequent carboxylation of the amino group to obtain the carbamate which is then converted to the methyl carbamate in a separate step. The methylation steps are also mediated by the SAM Pathway No. 1, and thus at least two SAM pathways are used in the biosynthesis of the wye base.

The complexity of the wye base modification varies with evolutionary complexity. The wye base is inserted into tRNA$^{Phe}$ in increasing levels as the organism ages. Wye base substitution is elevated in cells undergoing differentiation but decreased in rapidly proliferating cells. It is not found in the tRNA$^{Phe}$ of cancer patients which is consistent with the "de-differentiation state" of cancer.

Wye base incorporation into tRNA$^{Phe}$ also produces higher fidelity in reading amber stop codons; absence of the wye base from this tRNA allows read-through and, in some cases, frameshifting. This effect is similar to and related to the effect of queuosine modification of tRNAs which results from the SAM Pathway No. 4, described below.

The 3-amino-3-carboxypropyl group is currently added to only one eukaryotic protein in all of nature, elongation factor 2 (EF-2). After addition to a histidine residue in EF-2, the 3-amino-3-carboxypropyl group is converted to an amide and further methylated with 3 methyl groups from SAM at the carboxy moiety to form the diphthamide derivative. The conversion from the histidine residue to the diphthamide residue occurs during cellular proliferation and the diphthamide residue is the target of diphtheria toxin which inactivates EF-2 by adding ADP to the histidine residue.

In the lower eukaryote, *Dictyostelium discoidium*, the 3-amino-3-carboxypropyl group is added to isopentenyladenine to form 3-(3-amino-3-carboxypropyl)N⁶-(2-isopentyl) adenine, also known as discadenine (Kersten, *Prog. Nucl. Acid. Res. Molec. Biol.* 31:59–114 (1984)). This purine base derivative inhibits spore germination, in part by inhibiting the expression of specific proteins which are required in the early period of spore germination. The discadenine-mediated effects on expression of these proteins and on spore germination itself is abolished by cAMP.

SAM Pathway No. 4: Rearrangement of the Ribose Sugar of SAM to Form the Queuine Base SAM Pathway No. 4 (FIG. 5) results in the donation of ribose from SAM to form a queuine base (and queuosine nucleoside). Eukaryotes do not perform this conversion, and the queuine group is therefore required as a vitamin, like biotin. Once formed, queuine is substituted within the anticodon region of several tRNAs to form the queuosine nucleoside. Queuine is associated with the anticodon in four tRNAs: tRNA$_{Tyr}$, tRNA$^{His}$, tRNA$^{Asp}$, and tRNA$^{Asn}$. The modified base, queuine, when present in tRNA, assures fidelity of translation by controlling read-through of stop codons and frame-shifting at stop codons, as well as ribosome hopping. Thus a simple modification of a tRNA species can lead to a radical alteration in gene expression. Viral replication is often dependent upon readthrough or hopping of a stop codon. This is also true for HIV; cells infected with HIV do not incorporate queuine into their tRNA.

The presence of queuine in tRNA appears to be associated with differentiation and aging in higher organisms. In rats, for example, queuine levels in tRNA increase with age up to nine months and then plateau until death. This parallels the levels of LDH-5 isoenzyme, leading to the notion that queuine in tRNA regulates the metabolism of lactate; the isoform LDH-5 (consisting of muscle monomeric units as the tetrameric MMM) is induced by cAM. Binding of cAMP to receptors is modulated by queuine-containing tRNAs or by queuine per se. In addition, the lactic acid produced by LDH controls intracellular pH gradients which are associated with stalk cell differentiation in plants.

Figure 5:
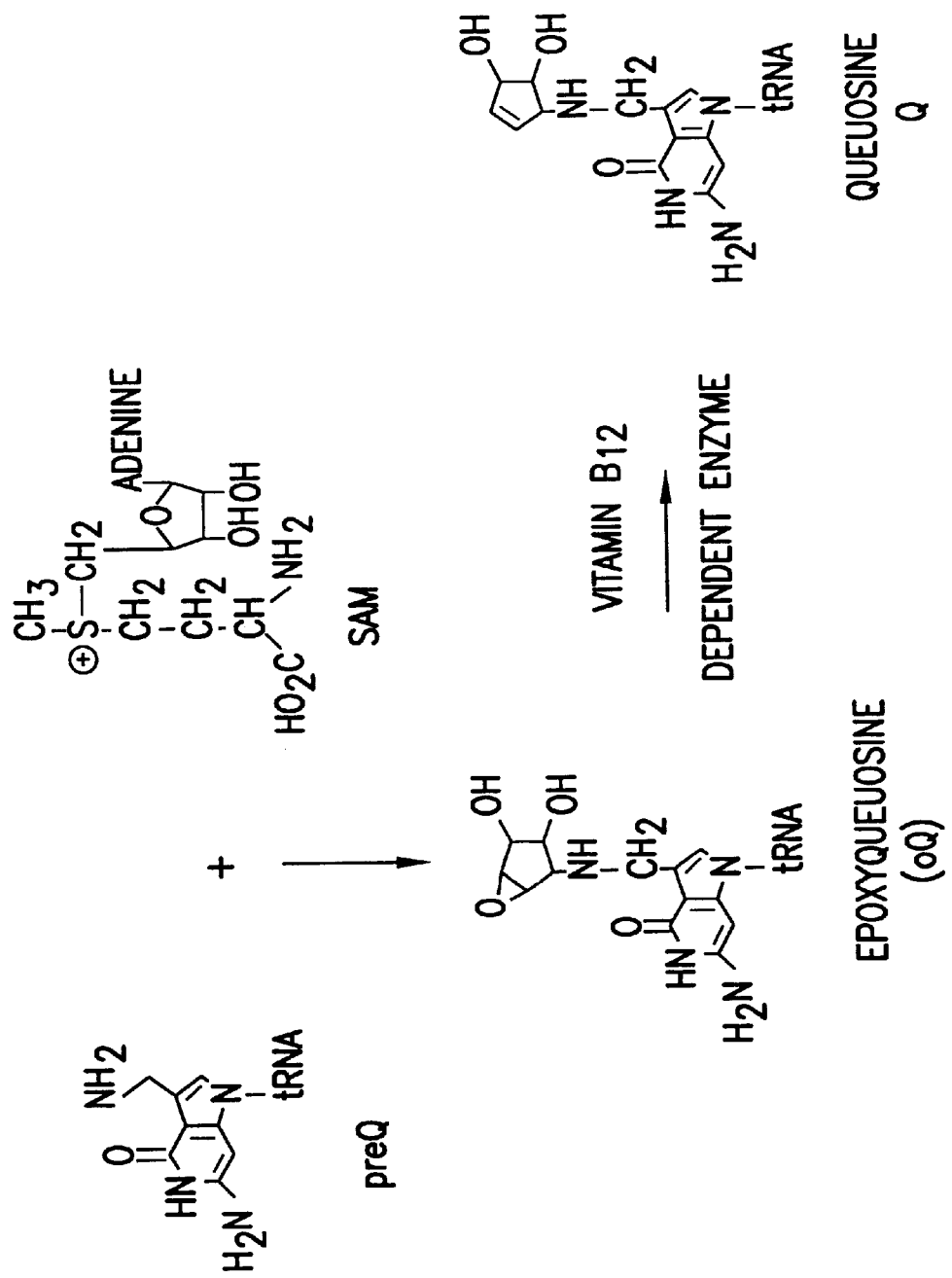
FIG. 5 is a schematic illustration of SAM Pathway No. 4 leading to queuine and queuosine bases and tRNA modified with these bases.
Figure 6:
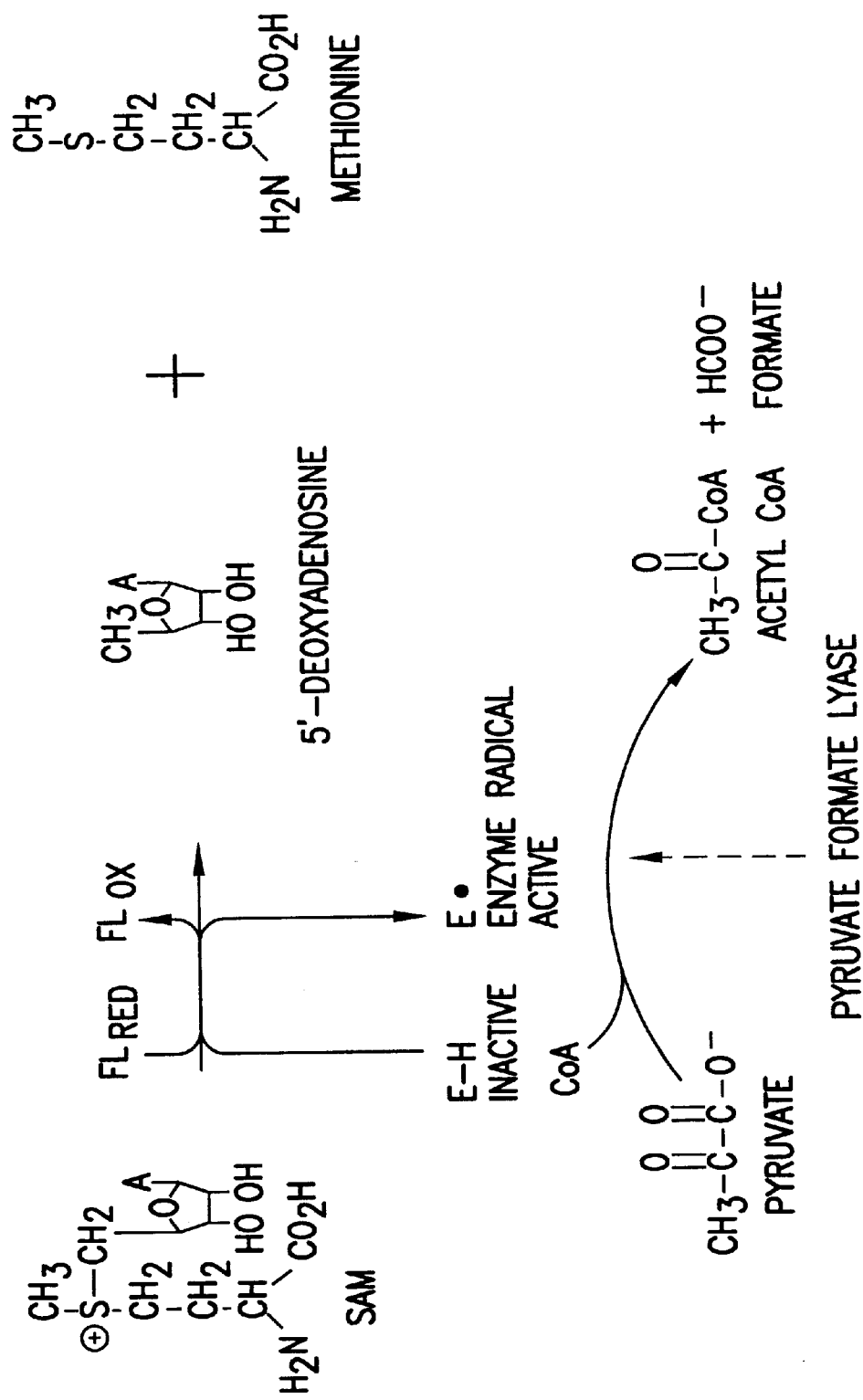
FIG. 6 is a schematic illustration of SAM Pathway No. 5 which leads to the activation of anaerobic enzymes through the formation of a free radical of 5'-deoxyadenosine.

In bacteria, the queuine conversion is effected by metabolic conversions of a 7-(aminomethyl)-7-deazaguanine which is substituted for a guanine at position 34 (the "wobble" nucleotide) by a guanine transglycosylase. As shown in FIG. 5, SAM donates a ribosyl moiety to the modified base. While this pathway is not known to occur in eukaryotes, the product of this pathway is nevertheless significant in the metabolism of higher organisms. In addition, epidermal growth factor receptor activity and related responses are modulated by queuine (Langgut et al., *Oncogene* 8:3141–3147 (1993)).

Queuosine and derivatives are widely distributed in microorganisms, animals and plants (Yokoyama et al. *Nature* 282: 107–109 (1979)). However, exogenous queuine is essential for the biosynthesis of queuosine-containing transfer RNA in mammals (Reyneiers et al., *J. Biol. Chem.* 256:11591-(1981)).

Queuine has been hypothesized to substitute for growth factors and modulates proliferation, phosphorylation and expression of proto-oncogenes c-fos and c-jun (Langgut, *Biofactors* 4:117–122 (1993); Langgut et al., *FEBS Lett.* 265:33–36 (1990)). Queuine incorporation into tRNA correlates with the degree of differentiation.

Queuine is itself regulated. Its uptake is modulated by protein kinase C; hence Ca$^{+2}$ and/or calmodulin levels may be involved in regulation (Elliot et al., *Biochem. Biophys. Res. Comm.* 171:393–400 (1990)). Queuine incorporation into tRNA is affected by pterins and oxygen partial pressure (Jacobson et al. *Nucl. Acids Res.* 9:2351–2357 (1981); Parniak et al., *Exp. Cell Res.* 195:114–118 (1991); Langgut et al., *Biofactors* 2:245–249 (1990)). Therefore in the absence of O$_2$ or in cases of decreased O$_2$ tension, queuine should be absent from the tRNA. A particular feature of tumors is the fact that they are hypoxic and survive for prolonged periods under hypoxic conditions. tRNA in tumors and virus-infected cells is hypomodified for queuine and the level of malignancy inversely correlate with the degree of Q base incorporation.

Queuine has been used to treat cancer in a mouse model. In one case it resulted in shrinkage of the tumor (Katze et al., *Biochem. Biophys. Res. Comm.* 96:313–319 (1980)). In another case, queuine had no effect (Nishimura et al., *Recent Results Canc. Res.* 84:401–412 (1983)). However, the two cancers were of different types.

SAM Pathway No. 5: Free Radical Control of Aerobic/Anaerobic Metabolism From 5'-Deoxyadenosine SAM Pathway No. 5, labeled 5, results in formation of a free radical on the 5' carbon of 5'-deoxyadenosine which activates enzymes for anaerobic metabolism, thus providing a switch between aerobic and anaerobic states.

This pathway is best known in prokaryotes. Bacteria (e.g., *E. coli*) cultured in oxygen have a few key inactive, "latent" enzymes. Upon transfer to anaerobic conditions, SAM Pathway No. 5 is activated and a free radical of 5'-deoxyadenosine is produced which specifically activates these key latent enzymes. These enzymes are described below.

This pathway contributes to the survival of facultative microorganisms when they are transferred from an aerobic to an anaerobic atmosphere where their metabolism must be altered to perform in the absence of $O_2$. Given the notion that evolution is conservative, the cells appear simply to revert to their ancestral form of anaerobic metabolism which existed before the introduction of $O_2$ into the earth's atmosphere.

Four crucial enzymes are activated under anaerobic conditions in a pathway mediated by a free radical form of 5'-deoxyadenosine generated in this pathway from decomposition of SAM. Three of these have been shown to occur in prokaryotes: pyruvate formate lyase, a ribonucleotide reductase, and lysine 2,3-aminomutase. A fourth enzyme, lactic dehydrogenase$_R$ ($LDH_K$), is believed to occur only in eukaryotes.

Pyruvate formate lyase generates the essential intermediate acetyl CoA by decomposing pyruvate in the presence of coenzyme A to obtain acetyl CoA and formate. This enzyme can comprise 3–5% of the total protein mass of *E. coli* and is only activated under anaerobic conditions by the 5'-deoxyadenosine free radical from SAM in the presence of reduced flavoprotein (and possibly other cofactors). Under aerobic conditions, this enzyme is inactivated by $O_2$, and pyruvate is converted to acetyl CoA and $CO_2$ by the pyruvate dehydrogenase complex. This process of activation of this enzyme by SAM Pathway No. 5 in the absence of $O_2$ and inactivation in the presence of $O_2$ is reversibly catalyzed by a deactivase enzyme and is essential for the survival of the microbe. The pyruvate formate lyase enzyme was discovered in *E. coli* (Knappe, J., In: *Anaerobic Dissimilation of Pyruvate in Escherichia coli and Salmonella typhimurium*, Ingraham et al., eds., Amer. Soc. Microbiol. Publ., Washington, D.C., 1987, pp.151–155) and is thought by the present inventors to have gone undetected in eukaryotic cells due to its inactivity under the aerobic conditions of most extractions procedures.

Ribonucleotide reductase accomplishes the conversion of ribonucleotides to deoxyribonucleotides under aerobic conditions using ribonucleoside diphosphates as substrate. This enzyme requires molecular oxygen for generation of a tyrosine radical at its active site and hence is inactive under anaerobic conditions. A different ribonucleoside reductase is activated under anaerobic conditions. This enzyme, in contrast to the aerobic ribonucleotide reductase, uses ribonucleoside triphosphates as substrate and has a cysteine radical at its active site that is quenched by molecular oxygen. This anaerobic enzyme is activated by the 5'-deoxyadenosine free radical generated in SAM Pathway No. 5 and permits synthesis of DNA under anaerobic conditions. When *E. coli* cells are returned to aerobic conditions, this anaerobic ribonucleotide reductase is immediately and reversibly converted to its latent form by $O_2$.

The fourth enzyme of this group, lysine-2,3-amino mutase has been found in prokaryotes and permits them to utilize lysine as a sole source of carbon under anaerobic conditions.

$LDH_K$ is thought to be an oncogene and serves as a marker for transformed and metastasizing cells. $LDH_K$ is activated only at low oxygen pressures. It has been shown that $LDH_K$ activity is present in HeLa cell extracts in the absence, but not the presence of oxygen. The present inventors have shown that addition of SAM to the assay mixture produced an 8-10-fold increase in activity of $LDH_K$. $LDH_K$ is putatively encoded in DNA of cells infected with Kirsten sarcoma virus, Harvey sarcoma virus, or Rasheed sarcoma virus, all of which contain the ras gene.

SAM Pathway No. 6: Ethylene Formation

In SAM Pathway No. 6 (FIG. 7), SAM undergoes a complex rearrangement to form a modified cyclopropane ring, which then is converted to ethylene. Ethylene is known to be an important metabolic regulator, especially in plants. A Schiff base formed between pyridoxal phosphate and the amino group on the methionine residue of SAM is rearranged and cleaved by ACC synthase to form aminocyclopropane carboxylic acid (ACC) which is ultimately converted to ethylene. The final oxidation of free ACC requires molecular oxygen, ferrous ion, ascorbic acid, α-ketoglutarate, $CO_2$ and an oxidizing agent such as peroxide.

Figure 7:
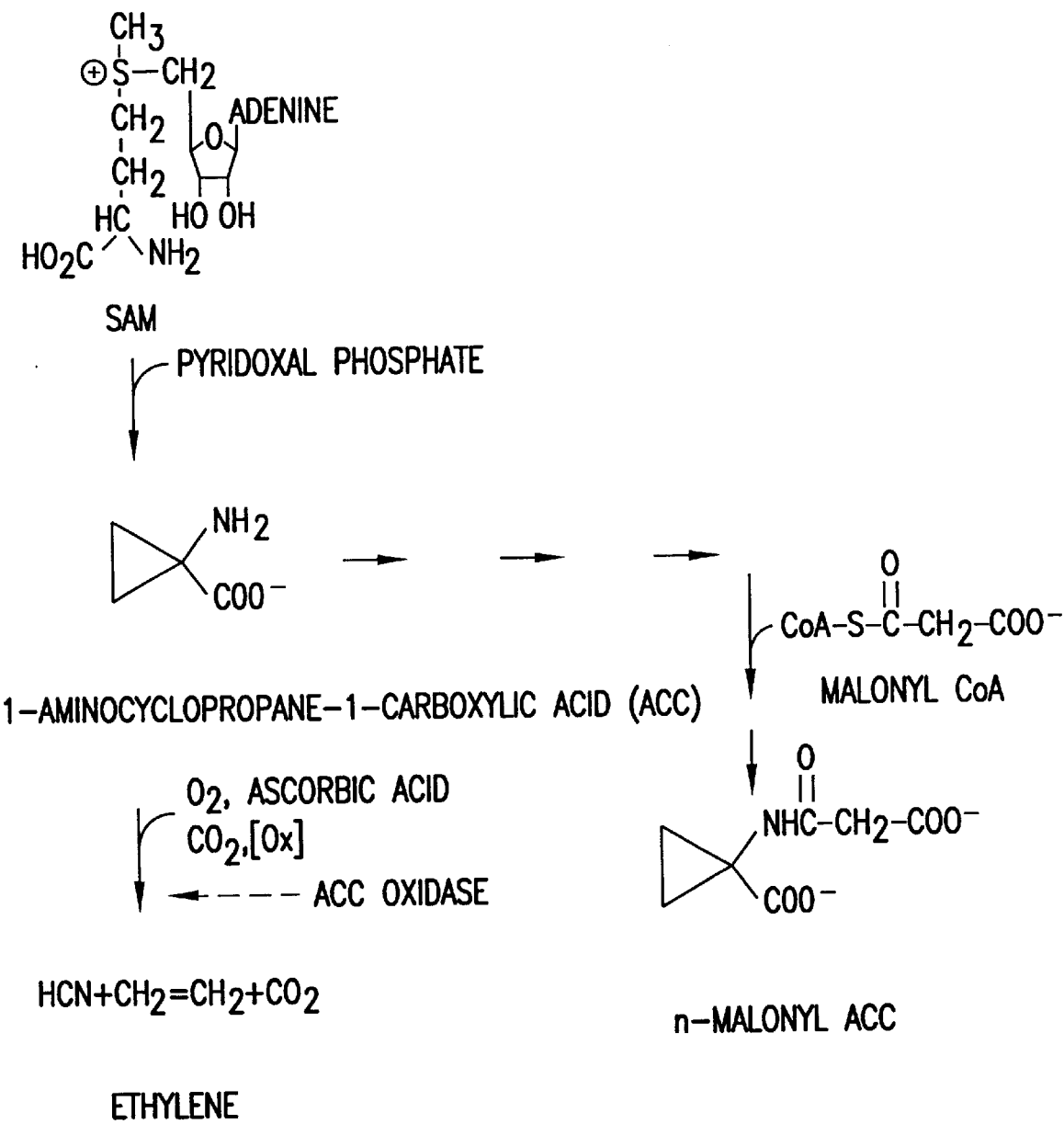
FIG. 7 is a schematic illustration of SAM Pathway No. 6 which leads to production of ethylene.

Malonyl CoA, which is produced by the biotin-mediated carboxylation of acetyl CoA, modulates the levels of free ACC as shown in FIG. 7. Thus, ethylene levels are in part controlled by biotin which is in turn controlled by the SAM Pathway No. 8 (see below) in plants. Furthermore, production of ACC by ACC synthase and its oxidation by ACC oxidase are inhibited by physiological concentrations of spermidine and spermine which are generated by the SAM Pathway No. 2 (supra). Salicylic acid is also an inhibitor of ACC oxidase.

Ethylene in plants is involved in aging, senescence (for example, fruit ripening), programmed cell death (abscission of leaves), fertility, maleness or femaleness, and the orientation of microtubule structures in the cytoskeleton. For example, when exposed to high concentrations of ethylene, the plants become females whereas those exposed to low concentrations of ethylene become males. The production of ethylene in plants is associated with certain stress conditions such as hypoxia, heat, chemical stress, gravitational stress, osmotic pressure, drought, gamma irradiation and wounding. Ethylene also induces decoupling of ATP production in the mitochondria by an alternative pathway which produces heat. Ethylene significantly accelerates the nymphal growth of the grasshopper during the 3rd and 4th instars. The observation suggests an important role in animal development.

Ethylene in animals is known to induce sleep, including, at higher concentrations, the induction of a catatonic state under which surgery can be performed without pain. These observations further suggest that ethylene may be produced naturally during sleep and during the body's response to major injury. In animals, ethylene may play a major role in wound healing as it does in plants; the poor wound healing in subjects with scurvy may reflect the requirement for ascorbic acid in the synthesis of ethylene from ACC.

Tumor cells release five-fold more ethylene than do normal cells, thus connecting this pathway with cancer. Ethylene is excreted in the breath of humans and is found to peak during the period of ovulation in human females. The latter suggests a role in sexual development and/or regulation in humans.

SAM Pathway No. 7: Cleavage to Methylthioadenosine and Homoserine

Figure 8:
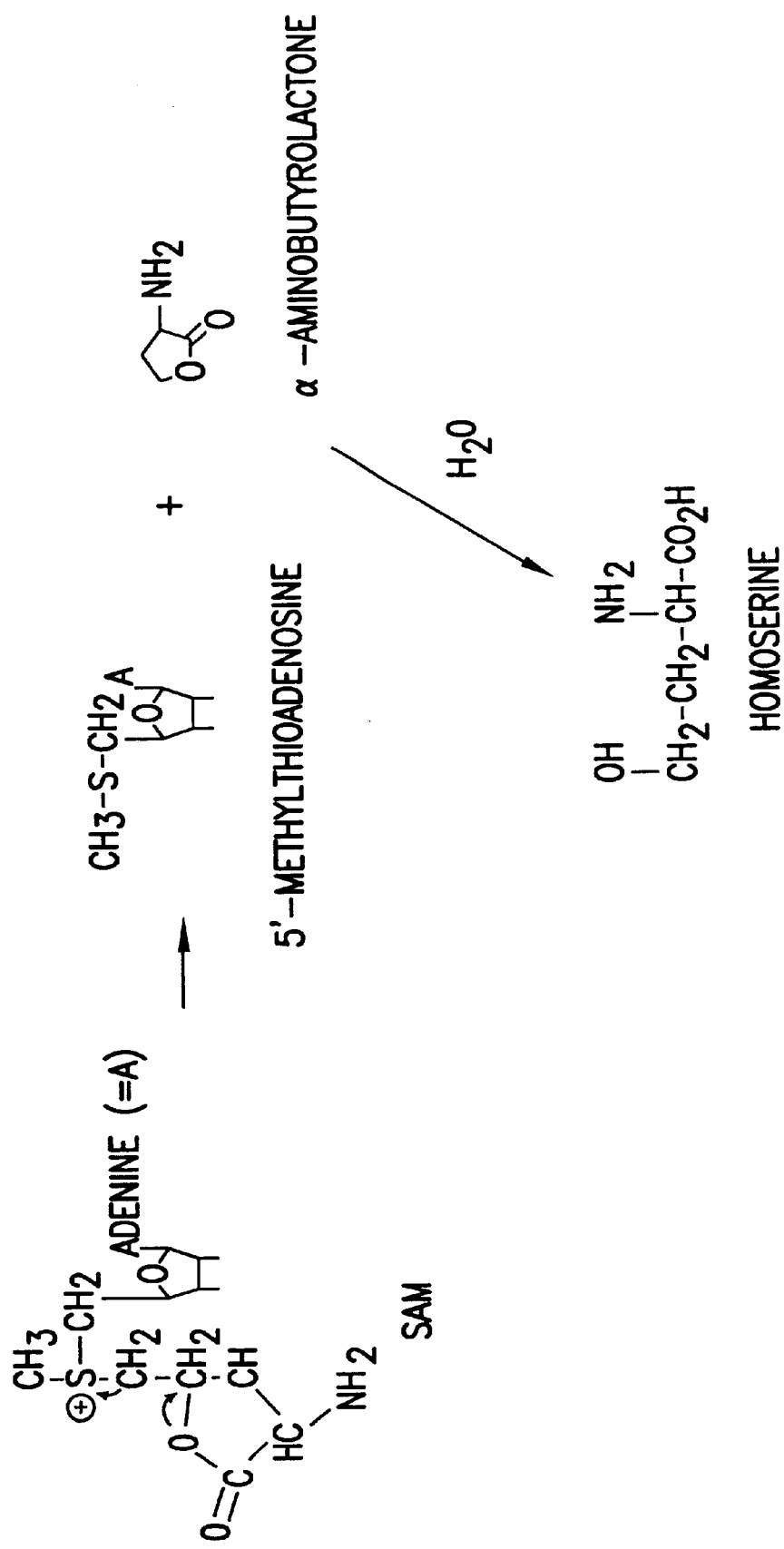
FIG. 8 is a schematic illustration of SAM Pathway No. 7 which generates MTA and homoserine.

In SAM Pathway No. 7 (FIG. 8), SAM undergoes internal cleavage to generate 5'-methylthiodeoxyadenosine and homoserine lactone (γ-aminobutyrolactone). The latter product is transitory and spontaneously forms homoserine by ring opening (nonenzymatic hydrolysis). Homoserine lactone and 5'-methylthioadenosine can also recombine nonenzymatically to yield SAM. Thus, this pathway appears to regulate the levels of SAM in vivo as well as contributing to processes through its product 5'-methylthioadenosine which has significant physiological properties as previously reviewed (Williams-Ashman et al., *Biochem. Pharmacol.* 31:277–288 (1982). In addition to its production in SAM Pathway No. 7, MTA is also produced in SAM Pathways Nos. 2, 3 and 6. MTA is an inhibitor of the diphthamide formation in EF-2 and appears to modulate specifically the biosynthesis of diphthamide in EF-2 in murine lymphoma cells (Yamanaka et al., *Biochim. Biophys. Acta*, 888:157–162 (1986)). MTA caused profound elevations of adenine nucleotides as well as inhibition of 5-phosphoribosyl-1-pyrophosphate accumulation in Sarcoma 180 cells (Savarese et al., *Biochem. Pharmacol.* 30:189–199 (1981)).

It is believed that the coupling of the homoserine lactone to 5'-methyladenosine may have provided one of the prebiotic synthetic pathways for SAM based on the facts that (1) homoserine can be converted readily via an intramolecular cyclization to γ-aminobutyrolactone by simple heating and (2) γ-aminobutyrolactone reacts spontaneously with 5'-methylthioadenosine to form SAM in high yield. Hence, it is likely that the lactone was present in the prebiotic soup, and these two simple chemical reactions could have allowed the continuous chemical production of SAM in that environment. Homoserine was a product of the spark discharge experiments of Miller and colleagues (Van Trump et al., *Science* 178:859–860 (1972)) and has been found in carbonaceous meteorites.

Several homoserine lactone analogs are of known importance in particular biological activities. N-(β-oxo-hexan-1-oyl)1-homoserine lactone induces bioluminescence in *Vibrio fischeri*. N-(β-oxo-octan-1-oyl)-1-homoserine lactone increases conjugal transfer efficiency of the Ti plasmid between various strains of *Agrobacterium tumefaciens*. Homoserine lactone may therefore modulate recombination events in the cell.

MTA is a product of four SAM pathways, namely SAM Pathways No. 2 (polyamines), 3 (3-carboxy-3-aminopropyl group), 6 (ethylene) and 7 (homoserine lactone). Although some of these pathways produce very large amounts of product such as the polyamines, only very small amounts of MTA are found in the normal cell. It follows that a rapid and highly efficient system must exist for removal of MTA. Addition of exogenous MTA to cells has confirmed this, and some of these effects are listed below. MTA is a suicide inhibitor of SAH hydrolase and acts as an inhibitor of spermidine synthase, spermine synthase and PRPP synthetase. MTA disposal is often disrupted in cancer cells (see Example II, below).

SAM Pathway No. 8: Biotin Biosynthesis

Figure 9:
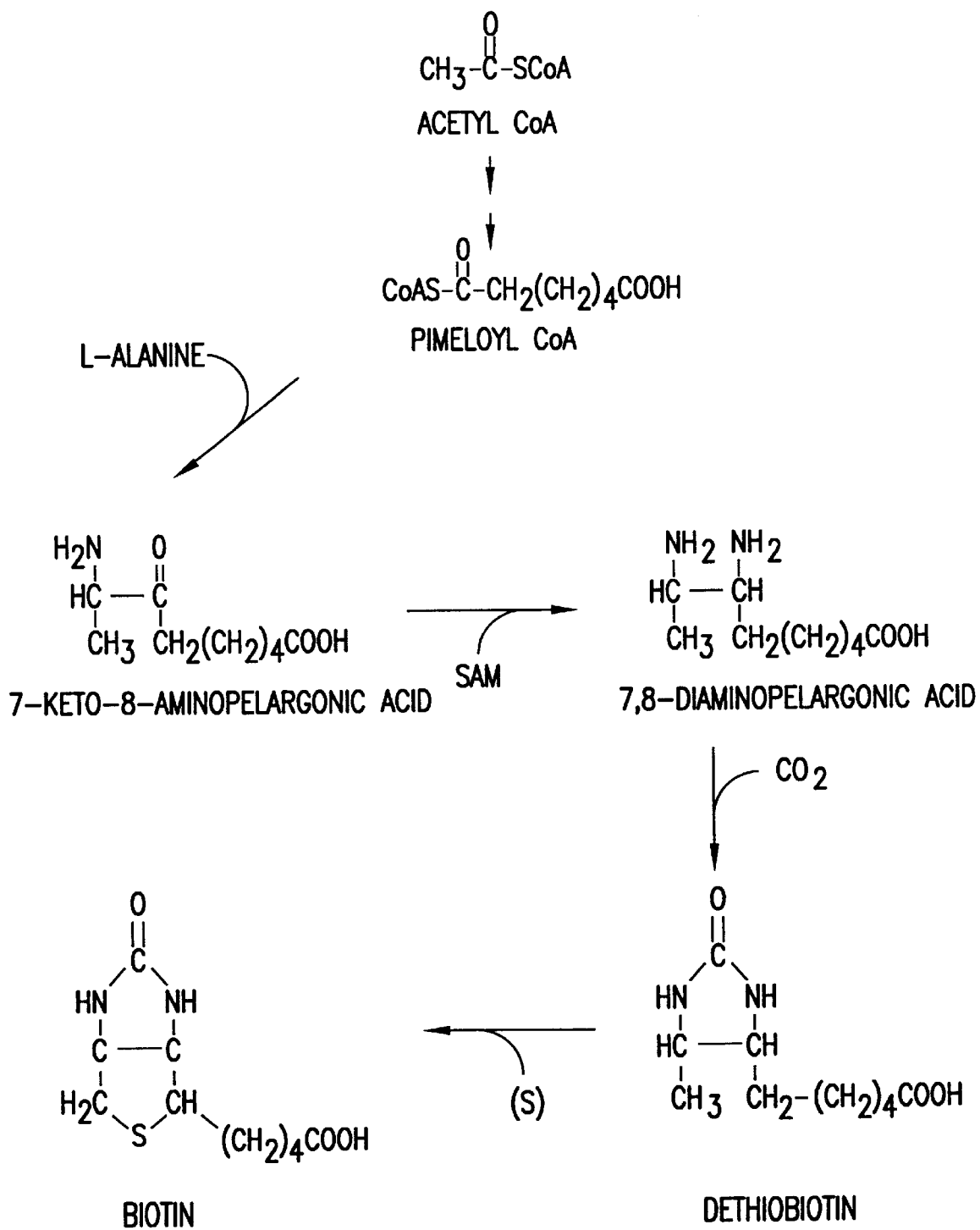
FIG. 9 is a schematic illustration of SAM Pathway No. 8 leading to biotin synthesis.

SAM Pathway No. 8 (FIG. 9) results in the transfer of the amino group of the methionyl portion of SAM for the synthesis of biotin, one of the most important cofactors in nature. Although the synthesis of biotin is regulated by repressor and corepressor proteins at the genetic level in *E. coli*, the pathway of biotin biosynthesis, shown in FIG. 9, demonstrates that SAM Pathway No. 8 exerts a critical influence on biotin levels. The donated amino group is required to convert the intermediate 7-keto-8-aminopelargonic acid (7-KAP) to 7,8-diaminopelargonic acid (DAPA). Regulation of this SAM pathway governs the levels of biotin available per se. In mammals however, biotin is required as a vitamin and a different regulatory mechanism has evolved to control its availability. Biotin uptake is coupled to Na$^+$-gradient-dependent uptake in a number of cell types (liver cells, human intestinal cell line Caco-2, bovine brain microvessel endothelial cells). In this biotin-saturable carrier-mediated system it was shown that the ratio of biotin to sodium was 1:1. Additionally, it is known that: (a) cerebrospinal fluid biotin concentrations are 2.5 times higher than serum concentrations, (b) biotin-deficient cells accumulate about 16-fold more biotin than do normal cells when incubated with a physiological concentration of biotin for 24 hrs and (c) 2-deoxyglucose pretreatment of basolateral-to-apical transport of biotin was substantially attenuated in bovine brain microvessel endothelial cells.

In addition to the uptake step for biotin, there also appears to be a Na$^+$-independent but saturable carrier-mediated exit transport system in the basolateral membrane of the small intestinal mucosa. The intestinal mucosal carrier-mediated transport system is adaptable and includes a feedback loop that reflects body biotin levels (Said et al., *Am. J. Physiol.* 256:G306–311 (1989)). Biotinidase is a salvage enzyme that hydrolyzes biotin esters and biotin peptides. Biotinidase activity in mouse serum is enhanced by the action of methylation inhibitors (Kontinen et al., *Mol. Cell. Biochem.* 76:85–91 (1987)).

The above points suggests the existence of multiple regulatory mechanisms for controlling local biotin concentrations, potentially involving SAM pathway metabolites. This amino transfer from SAM is highly specific; this is its only known occurrence in nature, suggesting that it was selected for an unusually important function during the origin of life. Once synthesized, biotin is conjugated to only four known enzymes in the eukaryotic cell where it functions as a prosthetic groups to fix $CO_2$ into four small molecules. Not surprisingly, each of these $CO_2$-fixed molecules lies at an intersection between major and universal pathways of metabolism. A fifth biotin-containing enzyme has been found in pig liver and is involved in degradation of farnesyl and geranyl groups.

Biotin has a critical role in regulating metabolism at various levels. Four biotin conversions are known in mammalian metabolism wherein biotin mediates $CO_2$ fixation using four carboxylase enzymes: (1) acetyl CoA carboxylase to convert acetyl CoA to malonyl CoA; (2) propionyl CoA carboxylase to convert propionyl CoA to D-methylmalonyl CoA; (3) 3-methylcrotonyl CoA carboxylase to convert β-methylcrotonyl CoA to β-methylglutaconyl CoA which is then hydrated to form β-hydroxy-β-methylglutaryl CoA (HMG CoA); and (4) pyruvate carboxylase to convert pyruvate to oxaloacetate. Another central reaction is (5) biotin-mediated catabolism of geranyl and farnesyl groups.

Malonyl CoA is the source of two carbon units in the formation of lipids, provides a means to control levels of ethylene through reaction with ACC synthesized in SAM Pathway No. 6 (supra), and may be required for the synthesis of mevalonic acid, an intermediate in the biosynthesis of isoprenoid compounds including the steroid hormones.

Biotin functions as a prosthetic group in carboxylations, transcarboxylations and decarboxylations. Biotin is therefore required for replacement of components of the citric acid cycle that have been removed for biosynthetic purposes, including synthesis of oxaloacetate from pyruvate and synthesis of succinyl CoA from valine, isoleucine or methionine. Biotin also mediates the reactions which convert leucine to HMG CoA, which in turn can replenish a citric acid cycle intermediate (i.e., acetyl CoA) or which can function as precursor to intermediates in the synthesis of isopentenyl derivatives, as well as in other cellular transformations such as modification of transfer RNA at the anticodon and generation of cytokins.

Biotin-mediated $CO_2$ fixation is involved in degradation of geranyl and farnesyl groups in microbes; this degradation system is also present in extracts of pig liver. Geranyl and farnesyl groups are responsible for the prenylation reactions that are required for the function of certain proteins involved in signal transduction.

In general biotin is required for the growth of human cells, this can be demonstrated by the successful growth of human cells in culture media containing adult bovine serum or dialyzed fetal calf serum when these media are supplemented with biotin. However, in the absence of this biotin supplement, the cells grow poorly. When biotin-deficient animals are fed labeled biotin, it first localizes in the cell nucleus in the area of the chromatin and restores RNA synthesis. This restoration may be due to stimulation of cGMP synthesis through the known biotin-mediated stimulation of guanylate cyclase (Vesely et al., *Molec. Cell. Biochem.* 60:109–114 (1984)). cGMP has been proposed to be have a major role in the transformation of cells to malignancy. cGMT is known to induce RNA polymerase II and thereby, the synthesis of mRNA In biotin-deficient rats, there was a 2-fold increase in both RNA polymerase II and in the synthesis of RNA within 2 hours after injection of biotin. Increased levels of mRNA were associated with ribosomes. In such animals, the biotin was transported first to the nucleus. This in vivo outcome contrasts with in vitro studies wherein cells showed no transport of biotin to the nucleus. Therefore, an important nuclear role of biotin may need to be satisfied before biotin is delivered to the cytoplasm or mitochondria where it can be bound as a prosthetic group to the appropriate enzymes for $CO_2$ fixation. Biotin also appears to be required for activity of certain cellular methyl transferases; biotin levels thus modulate SAM Pathway No. 1.

Biotin affects the expression and/or activity of key cellular proteins. Free biotin induces the expression of the asialoglycoprotein (AsG) receptor in cells of the hepatocyte cell line, HepG2. Levels of surface AsG receptor are directly correlated with the differentiation state of the hepatocyte. This relationship may be critically important in human disease since the AsG protein binds cobalamin (and its derivatives) and delivers it to cells containing the AsG receptor. In rat cells, the AsG receptor is lost progressively as oncogenic transformation occurs, such that fully transformed cells contain no AsG receptor. Note that the loss of AsG receptor in some tumor cells could lead to a loss of cobalamin and thus a reduced ability to synthesize methionine from homocysteine. This phenotype is observed in many tumor cells. (See discussion below on methionine dependence of many tumor cells). Also, certain biotin effects could be mimicked with cGMP, indicating that the effect was related to biotin inducing cGMP synthesis.

Biotin is important in cell proliferation. There are significantly abnormal levels of biotin in cancer cells relative to normal cells. Generally, but not always, biotin levels are increased to the levels found in the same tissue during embryogenesis. Antitumor effects have been induced using the biotin analogue desthiobiotin and the biotin-binding protein avidin (Briggs, Sci. *Progress* 47:468–475 (1959). In these cases, further tumor growth was prevented, though tumor size attained prior to treatment was not reduced. Because low levels of biotin in tumors have also been observed (Briggs, supra), it is useful to characterize tumor types for levels of free and protein-bound biotin in a method for developing therapeutic compositions or protocols. In the studies mentioned above, total biotin was measured with no information about free versus protein-bound forms. This may be an important distinction for cancer diagnostics and therapeutics.

Biotin plays an important role in development. Biotin deficiency is a teratogenic condition in fetal mice and leads to severe malformations such as cleft palate and growth retardation. Biotin deficiency in rats produced significant reductions in luteinizing hormone and serum testosterone, the latter being reversible by treatment with gonadotrophins or biotin. The involvement of biotin in the control of testosterone levels suggests regulatory connections ("crosstalk") between the SAM Pathway No. 8 and SAM Pathway No. 2 (which generates polyamines) since testosterone can raise polyamine levels several hundred-fold in some cell types. Biotin deficiency in the adult mammal has major effects on the sloughing of seminiferous tubules which could be reversed by biotin treatment but not by treatment with testosterone. Biotin deficiency also causes gray hair, alopecia, skin lesions, and disorders of the reproductive system, the immune system, and the neuromuscular system. In addition, biotin-deficiency delays spermatogenesis (which in mammals is dependent on testosterone), reduces sperm count, and reduces testicular size.

The axonal degeneration in uremic neuropathy may be due to uremic toxins which inhibit microtubule formation. This effect is reversible by treatment with biotin. These biotin-mediated effects on microtubules may involve biotin binding to GAPDH (as discovered by one of the present inventors) which previously was reported to be a microtubule bundler.

A specific cellular system is responsible for biotin transport into cells. As rats age, the $K_m$ of the transport system remains constant but the $V_{max}$ increases substantially. Thus net transport of biotin increased significantly with aging. Consistent with this are the increased levels of biotin in the plasma. The only known biotin-binding protein in blood, biotinidase, is responsible for cleaving biocytin (biotin-lysine) to lysine and free biotin. In serum, biotinidase also binds to the lipoic acid-lysine conjugate cleaving the conjugate and producing free lipoic acid. Lipoic acid is found in several key complexes in human metabolism: the pyruvate dehydrogenase complex, α-ketoglutarate dehydrogenase complex, branched-chain ketoacid dehydrogenase complex, and the glycine cleavage system. In human breast milk, however, specific cleavage systems are found for both the biotin-lysine and lipoic acid-lysine conjugates.

Biotin also plays a role in differentiation. Biotin is the single factor required by 3T3 cells for their differentiation from adipocytes. During this process, levels of 11 proteins increase (5 of which are involved in glycolysis or lipid synthesis) and together account for 40% of total cellular protein. Three proteins, GAPDH, LDH, and aldolase, account for 20% of the total. GAPDH, aldolase, and glycerophosphate dehydrogenase increased 8 fold, 20–30 fold, and 2,000- fold, respectively. Two proteins decreased, one of which was actin (from 12.7% to 3.2% of total protein) the most abundant cellular protein prior to treatment with biotin. These biotin-dependent alterations were associated with increased levels of mRNAs for the glycolytic enzymes and, moreover, were also dependent on the presence of insulin. These results suggest that biotin has major effects on the differentiation of certain cells, and that some of the biological activities of biotin are interdependent on insulin in as yet undefined ways.

Free biotin also induces the expression of the insulin receptor. The insulin receptor and insulin-like receptors are tyrosine kinases which are known to be involved in proliferation. Free biotin also regulates the transcription of the glucokinase gene, which is expressed specifically in liver cells and pancreatic β-cells which produce insulin. Other enzymes and functions which are affected by biotin deficiency (in vitro or in vivo) are glucokinase, phosphofructokinase, pyruvate kinase, and pyruvate carboxylase, and the methylation and phosphorylation of histones. Consistent with this, biotin-deficient rats were found to be deficient in protein biosynthesis. The defect was found in tRNA at the level primarily of aminoacylation and was most likely due to improper modification and improper or inhibited methylation (SAM Pathway No. 1). Biotin-deficient cells have blocks in the synthesis of purines and carbamyl phosphate (a direct precursor of arginine and the pyrimidines). The enzymatic steps blocked involved $CO_2$ fixation which implicates biotin as being involved in $CO_2$ fixing reactions without being attached to a protein as a prosthetic group. Biotin-deficient rats exhibit inhibition of glyceraldehyde-3-phosphate dehydrogenase and pyruvate decarboxylase, and significant reduction in the ratio of NADH/NAD. This produces high levels of pyruvate and lactate.

Biotin plays a role in the anaerobic state of the cell. The levels of protein-bound biotin (due to the $CO_2$ fixing activity of biotin) may also affect the $pO_2$ levels in the blood by regulating the ratios of $CO_2/O_2$ bound to hemoglobin. This, in turn, would affect activation of the SAM Pathway No. 4 which results in release of the free radical of 5'-deoxyadenosine and activation of anaerobic enzymes. That biotin regulates $CO_2$ levels in humans is shown by the use of anticonvulsants such as phenobarbital to prevent grand mal seizures in epileptics. Such seizures can be triggered by improper levels of $CO_2$ in the blood. Anticonvulsants alter $CO_2$ levels by competing for biotin binding sites on biotin-binding proteins. For example, a linear relationship exists between the most effective anticonvulsants (e.g., phenobarbital, carbamazepine and phenytoin) and their ability to displace biotin from the biotin-binding site of the biotin scavenger biotinidase in human serum.

Biotin levels are aberrant in many disease states, including cancer, late onset diabetes, Crohn's Disease, sudden infant death syndrome (SIDS) and many others.

Cross Talk: Interrelationships Between the SAM Pathways

The series of SAM pathways described above subserves a cohesive view of how metabolic reactions are controlled. While the nature of these pathways has been outlined. individually, it should be clear that the pathways are interrelated and that the status of one influences the status of others. Such interrelationships are termed "cross-talk" between the pathways. Important examples of such cross-talk are given below.

The role of biotin whose synthesis is controlled by SAM Pathway No. 8, provides a means to control ethylene levels produced by SAM Pathway No. 6. For example, in plants, biotin-mediated carboxylation of acetyl CoA produces malonyl CoA which subsequently reacts with aminocyclopropane carboxylic acid (ACC), as discussed above and shown in FIG. 7, to produce N-malonyl ACC, which is then stored in vesicles. Later, it appears the N-malonyl ACC is excreted or, in some cases, converted back to ACC and subsequently to ethylene.

Figure 10:
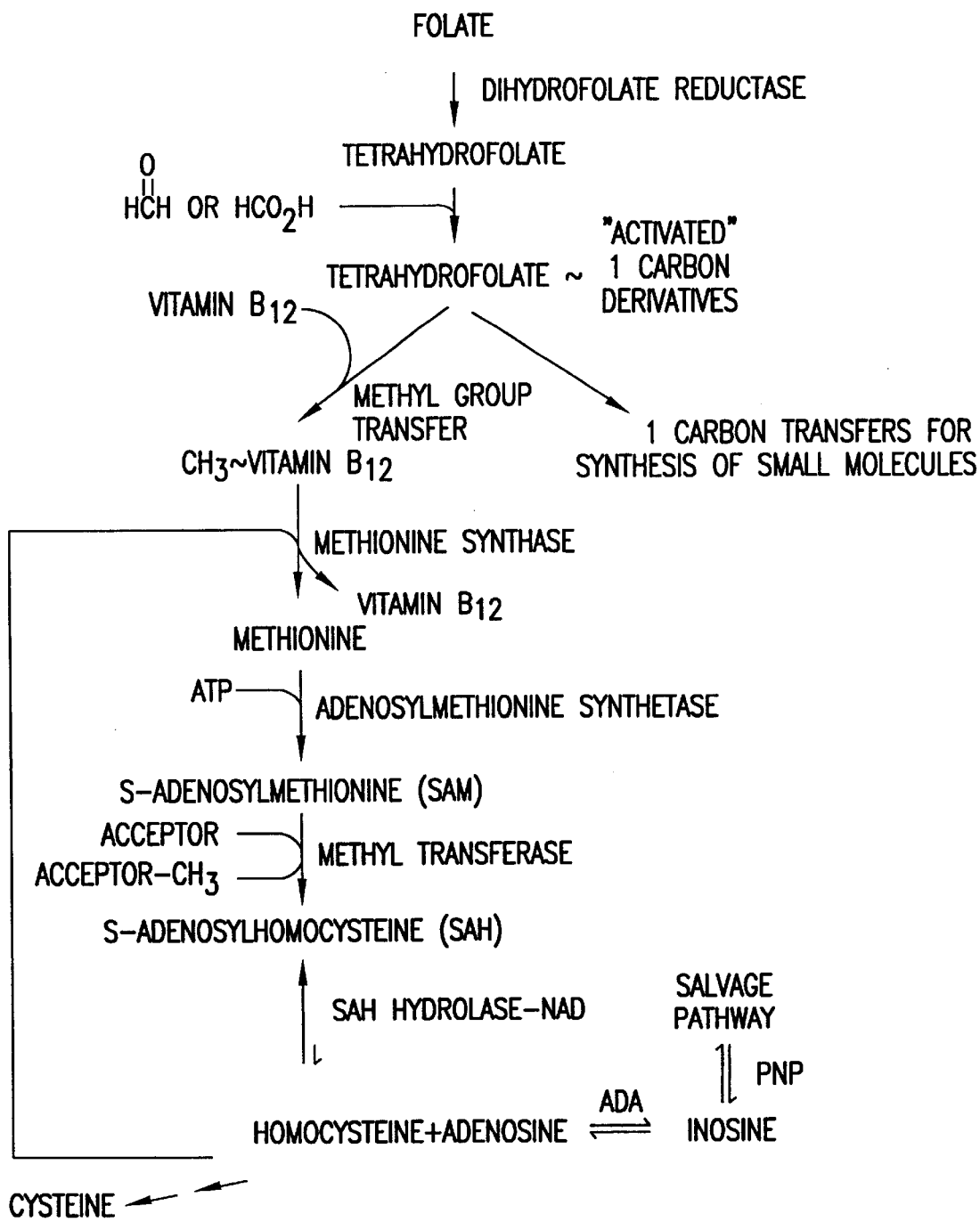
FIG. 10 is a schematic illustration of a pathway of folate metabolism showing the relationship of one-carbon metabolism through the folate/cobalamin system to the SAM pathways.

Biotin levels, in particular, influence the one-carbon metabolic system illustrated in FIG. 10, since biotin stimulates the expression of the gene for the asialoglycoprotein receptor which is reported to be a binding protein for cobalamin in serum. Enhanced availability of this receptor leads to increased delivery of cobalamin to the relevant cells. As shown in FIG. 10, cobalamin is needed to transfer a methyl group from the folate system to homocysteine to generate methionine and, therefore, SAM. Furthermore, reduced levels of biotin significantly inhibit the methylation state of cells.

The formation of spermidine and spermine by the SAM Pathway No. 2 also provides a means to control the production of ethylene by SAM Pathway No. 6, since ACC synthase and ACC oxidase are inhibited by these compounds. Reduced levels of polyamines significantly inhibit the methylation state of cells. In prokaryotes and lower eukaryotes, spermidine is found conjugated to glutathione (an indirect product of SAM Pathway No. 1) under anaerobic conditions.

The formation of methionine, and ultimately of SAM, depends finally on 1-carbon metabolism. This metabolism is regulated by the tetrahydrofolate ($FH_4$) system and the cobalamin (vitamin $B_{12}$) systems, summarized in FIG. 10. These known metabolic pathways may be modulated to regulate the levels of SAM available in the system so as to control SAM pathways of degradation in general. In particular, it is important to note that nature uses one-carbon groups within the folate system or on vitamin $B_{12}$ for the biosynthesis of less than ten small molecules. When the one carbon group is transferred to homocysteine to generate methionine and subsequently to generate SAM, it is used for regulatory purposes. In this case, the one carbon group can be transferred to both small molecules and macromolecules. Moreover, in addition to the one-carbon methyl group, regulation is achieved through the seven other SAM pathways described herein.

CONTROL OF KEY PATHWAYS THROUGH THIOL/DISULFIDE EXCHANGE

Homocysteine can be disposed of by three reaction pathways. First, it can be converted to methionine by methylation. Second, it can be oxidized and excreted. Third, it can be condensed with serine by cystathionine synthase to form cystathionine. Cystathionine then is cleaved by cystathionase to produce cysteine and a-ketobutyrate.

Cysteine, in turn, has several fates. It can be incorporated into proteins, it can undergo transamination to form α-ketopyruvate (which subsequently can be excreted), it can donate its sulfur group in key modifications of tRNA (e.g., the conversion of uridine to thiouridine in tRNA), and it can be incorporated into glutathione (γ-glutamylcysteinylglycine or GSH). Glutathione is found typically in a reduced form (GSH) or an oxidized form (GSSG). Moreover, this cellular concentrations of GSH and GSSG are regulated by four enzyme systems: peroxidase, reductase, transhydrogenase and protein transhydrogenase. These four enzyme systems constitute the glutathione cycle.

It is noteworthy that the reducing environment of the cell is set primarily by four thiol-containing species: homocysteine, cysteine, glutathione, and CoASH. Since homocysteine is one of the products of the SAM-mediated methylation pathway, SAM Pathway No. 1 plays a major role in adjusting the redox state of the mammalian cell by providing hoinocysteine which is the precursor of cysteine and ultimately glutathione.

The redox state of the cell sets the structural state of a thiol since its reduced form may be converted to its disulfide form by oxidation as shown below:

$$2RSH \rightarrow RSSR + 2H^+ + 2e^-$$

In addition, two thiol/disulfide pairs can undergo a process of thiol/disulfide exchange as shown below:

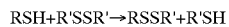
$$RSH + R'SSR' \rightarrow RSSR' + R'SH$$

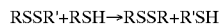
$$RSSR' + RSH \rightarrow RSSR + R'SH$$

These reactions take place quickly although the equilibrium of the reactions depends on the relative redox potentials of RSH or R'SH. The most reactive functional group within proteins is is generally the thiol group of cysteine which provides a potential system of enzyme regulation through thiol modification. For example, an enzyme can be modified by oxidized glutathione disulfide as shown directly below. It is also important to note that oxidized homocysteine (homocystine) or oxidized cysteine (cystine), as well as any of the possible mixed disulfides between glutathione, homocysteine and cysteine can also participate in these reactions.

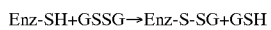

Enz-SH+GSSG→Enz-S-SG+GSH

These thiol exchange reactions occur rapidly and depend on the concentrations and the relative ratios of GSH and GSSG. Most importantly, such thiol-mediated modifications of enzymes have important effects on a small number of enzymes involved in regulation. A table of the key enzymes in metabolism which appear to be regulated by thiol/disulfide exchange switches are shown below. These enzymes can be regulated reciprocally by thiol modification (e.g., glycolysis versus gluconeogenesis).

TABLE I

SOME ENZYMES REGULATED BY THIOL/DISULFIDE EXCHANGES (Enz-S-S-R)

Pentose Phosphate Shunt

| | |
|---|---|
| Glucose-6-phosphate dehydrogenase | Abrogates inhibition by NADPH |

Glycolysis and Gluconeogenesis

| | |
|---|---|
| Glycogen Synthase D | Inactivated |
| Glycogen Synthase-1 | Inactivated |
| Phosphorylase phosphatase | Inactivated |
| Hexokinase | Inactivated |
| Glucose-6-phosphatase | Inactivated in absence of GSSG |
| Phosphofructokinase | |
| Fructose-1, 6-diphosphatase | Inactivated |
| Aldolase | Activated |
| Pyruvate kinase | 10-fold increase in $K_i$ for activator fructose-1-6-bisphosphate) |

Synthesis of acetyl CoA

| | |
|---|---|
| Pyruvate dehydrogenase | Inactivated |

Lipid and Isoprenoid Metabolism

| | |
|---|---|
| Fatty acid synthase | Inactivated |
| ATP citrate lyase | Inactivated |
| HMG-CoA reductase | Inactivated |

RNA Binding Proteins

| | |
|---|---|
| Adenosine-uridine binding factor | Inactivates RNA binding activity |
| Iron response element binding protein (cytoplasmic aconitase) | Inactivates RNA binding activity |

Protein synthesis

| | |
|---|---|
| Protein kinase which phosphorylates EIF-2α | Activated |

Signal transduction

| | |
|---|---|
| Adenylate kinase | Reduced response to activation |
| Guanylate kinase | Reduced response to activation |

Melatonin synthesis in the pineal

| | |
|---|---|
| Indoleamine-N acetyl transferase | |
| Acetyl CoA hydrolase | |

Other enzyme activities

| | |
|---|---|
| Heat shock proteins | |
| Leukocyte collagenase | Activated |
| Tyrosine amino transferase | Inactivated |
| Xanthine oxidase | |
| Sucrose synthase | Inhibits cleavage but not synthesis of sucrose |

Regulation Through Homocysteine Oxidation Products

Many carcinomas in cell culture are unable to grow on homocysteine as a carbon source and require methionine. This inability to grow on homocysteine is due in part to a failure to synthesize a metabolite of homocysteine (such as methionine) in adequate supply or to the accumulation of toxic metabolites of homocysteine. Homocysteine can be oxidized to homocystine or can be cyclized to the lactone, rearranged to homocysteine diketopiperazine and through oxidation, polymerized to homocysteine diketopiperazine. Any number of these products of oxidation could have adverse effects on the cell. In addition homocysteine levels can be reduced by the enzyme cystathionine synthase or methionine synthase. High levels of homocysteine have a strong correlation with heart disease. Malignant cells also have increased levels of homocysteine thiolactone. Cells from patients deficient in cystathionine synthase have growth patterns similar to malignant cell cultures. Whereas normal cells readily convert homocysteine to a sulfate ester of proteoglycans, cultured malignant cells cannot. Therefore these homocysteine metabolites may play a large role in the disease state.

SAM Pathway ON/OFF Switches and Rheostats

SAM regulation involves a combination of both on/off switches and rheostat effects. The modification of molecules or macromolecules with the 3-carboxy-3-aminopropyl group is an on/off switch, for example, the diphthalnide group in EF-2 which is necessary for elongation during protein synthesis. In contrast, polyamines generally function as rheostats, i.e., many enzyme activities are altered progressively as low concentrations of polyamines are raised to high levels. Polyamines, however, can function also as switches as in the modification of eIF-5A with spermidine, which subsequently is modified to hypusine. Protein synthesis and proliferation are "tied" to the conversion of the apoenzyme forms of EF-2 and eIF-5A to their holoenzyine forms by formation of the diphthamide and hypusine derivatives, respectively. As such, both of these derivatives are key targets of the present invention to stop proliferation of cancer cells and thereby, treat a subject with cancer.

SAM Pathway No. 1 is also a combination of on/off switches and rheostat effects. The on/off switch is the methylation of the substrate. The rheostat is the modulation of SAH hydrolase activity (by multiple mechanisms) which generates different SAH levels. The concentration of SAH, in turn, regulates methylation by differential inhibition of methyl transferase activities.

The important concept is that by combining on/off switches, particularly in the form of modification of specific molecules, with rheostats, wherein many macromolecules are globally affected by concentration differences as found with polyamines, nature has provided a highly complex system of cellular regulation which could be modulated at a higher level by simple mechanisms involving the SAM pathways.

When defining the regulation of metabolism through the SAM pathways, these switches should always be considered in normal cellular processes. In particular, these switches should also be considered in the disease states of man associated with aging. For example, a key link to atherosclerosis in many patients is an excessively high level of cellular homocysteine which has major effects on cellular metabolism.

MARKERS FOR DISEASE: ABERRANT LEVELS OF METHYLATED NUCLEIC ACIDS, PROTEINS AND SMALL MOLECULES

According to the present invention, aging is a programmed process which is regulated on a global level by the SAM pathways. In particular, aging and senescence are controlled, in part, by a progressive and continuous decrease in the methylation state of a variety of macromolecules and small molecules. This decrease is evident in both cellular methylation, and in the methylation state of neurotransmitters which allow communication between cells and organs. Disease states will arise when the normal homeostatic balance between modified RNAs, DNAs, proteins, and small molecules is significantly altered. Hence, aberrant levels in appropriate tissues of the macromolecules and small molecules will serve as diagnostic markers for disease states. Methods to determine and identify these markers are described herein. When such abnormal levels exist, the present invention provides therapeutic approaches which comprise bringing the methylation state of key macromolecules and small molecules back into homeostatic balance which insures a return of metabolism to the normal state. There are a number of ways to achieve this goal. For instance, since the SAM/SAH ratios determine the level of methylation in the cell, inhibition of SAH hydrolase as an example would decrease transmethylation reactions. In contrast a supplement of SAM to the cell would increase the ratio and stimulate transmethylation reactions.

METHYLATION OF RNA

1. Processing of rRNA

Alterations in RNA processing is particularly important in assessing disease states according to the present invention, since such processing is controlled extensively by RNA methylation. For example, processing of the ribosomal 45S RNA precursor (about 13 kb) requires extensive modification before the mature 18S rRNA (about 1.8 kb) and 28S rRNA (about 4.5 kb) are formed. These modifications are evolutionarily conserved during processing and are extensive (18S rRNA, 46 methylations, pseudouridines; 28S rRNA, 70 methylations). Treatment of cultured cells with specific inhibitors to reduce the state of cellular methylation alters rRNA processing such that very little 18s rRNA is formed whereas moderate levels of 28S rRNA and high levels of 45S rRNA are formed (Cabone et al., Europ. J. Biochem. 74:19–29 (1977)). In normal cells, the 45S rRNA is almost undetectable whereas both 18S and 28S rRNA are abundant.

It thus is of great interest (see CANCER section, below) that in acute lymphoblastic leukemia, very little 18S rRNA, moderate levels of 28S rRNA, and large amounts of 45S rRNA are detected. These levels of the precursors and mature forms of rRNA are hallmarks of perturbed cellular methylation within leukemia cells. In addition, several leukemic cell types can be switched by treatment with coformycin (an adenosine deaminase inhibitor) or deazaadenosine (an analogue of adenosine which subsequently is used by SAH hydrolase to form an analogue of SAH). Both of these inhibitors alter cellular methylation, thus suggesting that the various leukemias represent differentiated cell types which arise in excessive abundance due to simple perturbation of cellular methylation levels within erythropoietic stem cells.

2. Processing of mRNA

Pre-mRNA is also methylated, with major effects on its synthesis and processing. There are only a small number of modified bases in the mRNA of eukaryotes as shown below. All of these occur post-transcriptionally through methylation by SAM. In contrast, no similar modifications have been found in mRNA of bacteria. The known methylated bases in eukaryotic mRNA are:

| Symbol | Name |
|---|---|
| $m^7G$ | 7-methylguanosine |
| Cm | 2'-O-methylcytidine |
| Um | 2'-O-methyluridine |
| Gm | 2'-O-methylguanosine |
| Am | 2'-O-methyladenosine |
| $m^6Am$ | 2'-O-methyl-N6-methyladenosine |
| $m^6A$ | N6-methyladenosine |
| $m^5C$ | 5-methylcytidine |

Most mature mRNAs have the structure indicated below, wherein methyl groups are located externally at the 5'-terminal cap structure and internally at $m^6A$ and $m^5C$ residues.

5'$m^7$GpppN$_1$mN$_2$m - - - internal $m^6A$ and $m^5C$ - - - poly(A) 3'

Two SAM-mediated methylations which produce $m^7$GpppN$_1$m - - - occur immediately after initiation of pre-mRNA synthesis and appear in RNA transcripts over 30 nucleotides long. These methylations are thought to be required for initiation of RNA synthesis but not elongation, since addition of SAH (which is a methylation inhibitor) to a cell-free system before the start prevents RNA synthesis, whereas addition of SAH after initiation of RNA synthesis and extension beyond 30 nucleotides) has no effect on RNA synthesis. This methylation-related regulatory control clearly has major implications for the initiation of transcription of DNA and thus the control of gene expression.

After initiation and during or after elongation, the pre-mRNA is modified internally at specific sites to form $m^6A$ and $m^5C$. After, or as part of the splicing process, $m^6A$ and $m^5C$ are found in mature mRNA at levels of 1 per 800 nucleotides and 1 per 4000 nucleotides, respectively. In addition, for some pre-mRNAs (e.g., SV40 pre-mRNA), splicing and transport out of the nucleus does not occur if methylation is significantly inhibited. Following transfer of the mature mRNA to the cytoplasm, a fraction of the mRNA may be modified at the penultimate position of the 5'-terminus to form $N_2m$. For most, if not all eukaryotic mRNAs, there is an absolute requirement for the $m^7G$ modification before translation can occur.

Therefore methylation of mRNA functions to control initiation, splicing, transport and translation. In addition, as discussed below, methylation regulates alternative splicing of pre-mRNA An example of the translational effect is illustrated by 3-deazaadenosine which acts via its homocysteine derivative by interfering with a specific post-transcriptional methylation of influenza A viral mRNA. This influences the concentration of both early and late proteins, which inhibits the viral infectious cycle (Fischer et al., Virology 177:523–531 (1990)).

3. Regulation of Alternative Splicing by Modulation of Pre-mRNA Methylation

Indirect evidence shows that methylation is involved in alternative splicing of pre-mRNA. In Rous sarcoma virus (RSV)-infected cells, three size classes of mRNA are found. The first mRNA is the 35S species which encodes the gag core proteins (as a fusion polypeptide) and the gag-pol read-through product (also a fusion polypeptide) encoding the reverse transcriptase and integrase. The second mRNA is the 28S species which is generated by alternative splicing. It contains a spliced segment of over 300 nucleotides from the 5' end (the "leader sequence") of the 35S RNA and a long exon from the 3'-end of the 35S RNA. The 28S mRNA encodes the two envelope proteins. The third mRNA is the 21S species. It contains the "leader" sequence spliced to a shorter exon from the 3' end of the 35S RNA The 21S mRNA encodes the transforming protein pp60$^{src}$.

When cells are infected with RSV, there are specific, regulated levels of cellular 35 S, 28S and 21S RSV-specific mRNAs. When infected cells are treated with the methylation inhibitor cycloleucine at concentrations which inhibit 95% of cellular methylation, only the 35S viral mRNA is found (along with only trace amounts of the viral 28S and 21S mRNAs).

These results suggest a role for methylation in pre-mRNA splicing. Such regulatory methylation could occur at the pre-mRNA level and/or at the level of the small nuclear RNAs (snRNAs). The U1, U2, U4, U5 and U6 snRNAs are located in the spliceosome and are involved in pre-mRNA splicing. These five snRNAs range from 100–190 nucleotides in length and contain clusters of modifications consisting of methylated nucleotides and pseudouridines. The active sites of the snRNAs for pre-mRNA splicing have been identified and are about 6–8 nucleotides long. Most importantly, these active sites contain the most prominent clusters of modified nucleotides suggesting that modification (methylation) is important for splicing activity. In addition, some of the proteins contained within the spliceosome are modified with methyl groups. These results collectively suggest that SAM-mediated methylation can modulate alternative splicing of pre-mRNA in the nucleus.

The differentiation switch in many cell types consists of perturbations of alternative splicing of pre-mRNAs. This splicing, in turn, produces new protein isoforms with altered properties characteristic of the new differentiation state. Such changes in alternative splicing occur, for example, during development, during aging, and during progression into a specific disease states (e.g., solid tumors, leukemias, diabetes).

The control of pre-mRNA alternative splicing through methylation represents an epigenetic system for the regulation of gene expression. In this system, a linear sequence of DNA is copied into a co-linear sequence in the form of a pre-mRNA The pre-mRNA, however, can be alternatively spliced to produce multiple different mRNAs which, in turn, can produce multiple different protein isoforms. Modulation of the alternative splicing of pre-mRNA by methylation thus allows a single DNA sequence to be used for the synthesis of multiple protein isoforms with biological activities which are altered in minor or major ways. This suggests that perturbations of the methylation status of a cell can lead to a major reprogramming of its genetic information, for example, in ADA deficiency, where high levels of adenosine and SAH are produced, leading to inhibition of specific cellular methylases and preventing the differentiation of stem cells into the B and T cells of the immune system. In addition, other SAM pathways which can modulate methyltransferase activities also would be expected to play a major role in such reprogramming of gene expression, for example, polyamines produced by SAM Pathway No. 2. Regulation of gene expression through alternative splicing of pre-mRNA suggests that life still operates within an "RNA world". Viewed another way, by analogy with computers, RNA is in part the "software of life," serving as the program for manipulating information, whereas DNA is the "hard disk of life," operating as the stable repository for information storage.

Production of Aberrant β-amyloid Protein by Alternative Splicing in Alzheimer's Disease In Alzheimer's Disease (AD) patients, the major β-amyloid isoform found in insoluble deposits is generated from an alternatively spliced β-amyloid pre-mRNA. In accordance with the present invention and the SAM paradigm, the production of this alternatively spliced pre-mRNA and its protein isoform arise as a result of the lowered methylation status of the cells of AD patients. Consistent with this, a number of markers of methylation are reduced in AD: acetylcholine, ubiquinone, carnitine, etc. Also consistent with this, calcium levels and calmodulin activity are significantly altered in the cells of AD patients. Since calmodulin is methylated at its carboxyl terminus and also at Lys$^{115}$, alterations in its activity would be expected when the methylation status of the cell is significantly reduced.

4. Methylation of tRNA

The most heavily modified RNAs in nature are the tRNAs. As shown in Table II, below, 53 modified nucleosides have been found in tRNA Those listed are known in eukaryotes or in prokaryotes. Of these, 41 are directly modified in part by SAM-mediated methylation. Of the remaining nucleotides, 4 appear to be precursors of SAM-methylated nucleotides (conversion of N$^6$-isopentenyladenosine to 2-methylthio-N$^6$-isopentenyladenosine, N-((9-β-D-ribofuranosylpurine-6-yl)carbamoyl)-threonine to N-((9-βD-ribofuranosylpurine-6-yl)n-methyl-carbamoyl)-threonine, 2-thiouridine to 5-methyl-2-thiouridine, uridine-5-oxyacetic acid to uridine-5-oxoacetic acid methyl ester). The remaining 6 modified nucleotides are N$^4$-acetylcytidine, dihydrouridine, pseudouridine, inosine, 2-thiouridine, and 4-thiouridine. Of these 6 nucleotides, three additional nucleotide modifications may be related to SAM-mediated methylation. Thus inosine is a constituent of the salvage pathway of SAH (the by product of SAM-mediated methylation) and both the thiol group in 2-thiouridine and 4-thiouridine are derived from cysteine, which itself is generated in the salvage of homocysteine in eukaryotes. Thus, of the 53 known nucleotide modification, only 3 appear to be unrelated to SAM-mediated methylation, indicating the overwhelming importance of SAM-mediated methylation in nucleotide modification.

This potential for control is even more significant when it is realized that the 3-carboxy-3-aminopropyl group of SAM can be donated to RNA by a SAM Pathway No. 3, and the ribose sugar of SAM may be used in other RNA modifications.

Many of these modified nucleotides are not made in simple one-step conversions. Instead, a number of nucleotides are "hypermodified" through a series of complicated chemical steps, e.g., formation of wybutosine and its derivatives. This modification does not come without cost to the organism. It has been estimated that up to 3% of the genome of *E. coli* encodes proteins involved in RNA and DNA modification. Hence, nature has invested a significant amount of its genetic information into the modification of nucleic acids which supports the present inventors' recognition of a pivotal role for SAM-mediated modification of nucleic acids in the regulation of biological processes.

TABLE II

Modified Bases in tRNA

| | | | |
|---|---|---|---|
| $m^1A$ | 1-methyladenosine | Q | queuosine |
| $m^2A$ | 2-methyladenosine | manQ | β-D-mannosylqueuosine |
| 1Am | 2'-0-methyl-1-methyladenosine | galQ | β-D-galactosylqueuosine |
| $i^6A$ | N6-isopentenyladenosine | T | 5-methyluridine |
| $ms^2i^6A$ | 2-methylthio-N6-isopentenyl-adenosine | $s^2T$ | 5-methyl-2-thiouridine |
| | | Tm | 2'-0-methyl-5-methyluridine |
| $m^6A$ | N6-methyladenosine | $mam^5U$ | 5-methylaminomethyluridine |
| $t^6A$ | N-((9-β-D-ribofuranosylpurine-6-yl)carbamoyl)-threonine | $s^2U$ | 2-thiouridine |
| | | Um | 2'-0-methyluridine |
| $mt^6A$ | N-((9-β-D-ribofuranosylpurine-6-yl) n-methyl-carbamoyl)-threonine | $s^4U$ | 4-thiouridine |
| | | $cm^5U$ | 5-carbamoylmethyluridine |
| | | $mcm^5U$ | 5-methyoxycarbonylmethyluridine |
| $ms^2t^6A$ | N-((9-β-D-ribofuranosyl-2-methyl thiopurine-2-yl)-carbamoyl) threonine | $mam5^s2U$ | 5-methylaminomethyl-2-thiouridine |
| | | $mcm^5s^2U$ | 5-methoxycarbonylmethyl-2-thio-uridine |
| $s^2C$ | 2-thiocytidine | $o^5U$ | uridine-5-oxyacetic acid |
| Cm | 2'-0-methylcytidine | $mo^5U$ | 5-methoxyuridine |
| $ac^4C$ | N4-acetylcytidine | Mv | uridine-5-oxoacetic acid methyl ester |
| $m^5C$ | 5-methylcytidine | | |
| $m^3C$ | 3-methylcytidine | $cmnm^5U$ | 5-carboxymethylaminomethyl-uridine |
| $acp^2C$ | N2-(5-amino-5-carboxypentyl) cytidine | $cmnm^5s^2U$ | 5-carboxymethylaminomethyl-2-thiouridine |
| D | dihydrouridine | | |
| F | pseudouridine | $chm^5U$ | 5-(carboxyhydroxymethyl)uridine |
| $m^1F$ | 1-methylpseudouridine | $acp^3U$ | 3-(3-amino-3-carboxypropyl) uridine |
| Fm | 2'-0-methylpseudouridine | | |
| $m^1G$ | 1-methylguanosine | $mchm^5U$ | 5-(carboxyhydroxymethyl)uridine methyl ester |
| $m^2G$ | N2-methylguanosine | | |
| Gm | 2'-0-methylguanosine | Yw | wybutosine |
| $m^{2,2}G$ | N2,N2-dimethylguanosine | $o^2yW$ | wybutoxosine |
| $m^{2,2}Gm$ | 2'-0-methyl-N2,N2-dimethyl-guanosine | Cz | cis-zeatin |
| $m^7G$ | 7-methylguanosine | | |
| I | inosine | | |
| $m^1I$ | 1-methylinosine | | |

The levels and types of modifications of tRNA are different from tissue to tissue in eukaryotes, and change during embryogenesis, differentiation, proliferation, aging, starvation, hormone alteration, cancer, treatment with carcinogens, and infection with viruses (NIH Symposium, Cancer Res. 31:591–721 (1970)). In vitro tRNA methylase activities in liver and kidney homogenates from chickens infected with Marek's disease virus were elevated up to 3-fold compared to those in noninfected control animals (Mandel et al., Cancer Res, 31: 613–616 (1971)).

tRNA modification is also aberrant in cancer cells, with known increases in activity of tRNA methylation. In addition, SAM synthase is associated in a complex with tRNA methyltransferases in cancer cells but not in normal cells. tRNA modification is known to play a role in progression through cell cycle. In yeast, a mutant deficient in a modification enzyme for tRNA$^{lys}$ does not allow progression through G2. In higher eukaryotes, tRNAs and their modifications appear to play a role in cell cycle regulation.

METHYLATION OF DNA

This section describes the metabolic regulatory importance of DNA methylation, the understanding of which is important to the practice of the present invention.

Paternal and maternal genomes are not equivalent, and bothare required for mammalian development. During development of the embryo and after birth, some genes can "remember" from which parent they originated. This is possible because they inherit molecular imprints from the respective germ lines. As a result, only one parental copy of the gene is active in developing embryos. Methylation appears to function as a heritable molecular tag, able to regulate gene expression. Mutant mice with impaired methylation lost imprints on three genes, resulting in the expression or repression of both parental copies and the death of mutant embryos (Surant, M. A., Nature 366:302–303 (1993)). The SAM/SAH ratio in liver was positively correlated with DNA methylation, and negatively with transcription of three proto-oncogenes. Additionally decreased SAM/SAH ratios and hypomethylation of DNA were early features of hepatocarcinogenesis in rats (Simile et al., Cancer Lett. 79:9–16 (1994)).

Global DNA methylation decreases progressively in cervicalneoplasia and may serve as a biochemical marker (Kim et al., Cancer 74:893–899 (1994)). It has been shown that DNA methylation inhibits transcription indirectly via a methyl-CpG binding protein Boyes et al., Cell 64:1123–1134 (1991)). Stein et al., Infect. Immun. 56:112–116 (1988), demonstrated that transformation of gonococcal plasmid pFT 180 isolated from E. coil HB 101 or N. gonorrhoeae WR302 into gonococcal strain PGH3-2 required in vitro methylation with a special methylase. In the absence of methylation, transformation frequency was decreased five orders of magnitude. Razin et al. (Nucl. Acid Res. 2:1967–1974 (1975)), showed that methylation of bacteriophage DNA takes place during the last stage of DNA replication. Inhibition of this DNA methylation was accompanied by a corresponding decrease in phage production, indicating the vital role of methylation in the maturation of the virus.

METHYLATION OF PROTEINS

A wide variety of proteins with a diverse number of functions may be methylated (Pai et al (Eds), Protein

*Methylation*, CRC Press, Inc., Boca Raton, Fla., 1990). Abnormal methylation of these proteins may cause a detrimental effect to the cell. These proteins are divided into various categories below.

1. Nuclear Proteins

Histone H1, H2B, H3 and H4; lamin B; high mobility proteins 1 and 2 (HMG-1, HMG-2); A-1 protein of hnRNP; nucleolar protein C23 (also called nuclear specific phosphoprotein C23 or nucleolin); 34 kDa nucleolar protein (associates with U3 snRNA); and nucleolar scleroderma antigen.

2. Cytoskeletal Proteins

Myosin, actin, myelin basic protein, and myofibrillar protein.

3. Signal Transduction Proteins

Calmodulin, calcium dependent cyclic nucleotide phosphodiesterase, ras, G proteins, rhodopsin 4. Proteins Involved in Protein Synthesis a. Eukaryotes Ribosomal proteins (Spots 3, 20, 28, 50,51, 52, and 55); factors such as EF-1α, EF-31, EF-2 and eIF-5A (proteins modified with diphthamide and hypusine, respectively).

b. *E. coli*

Ribosomal proteins (S3, S9, S11 and L3, L7–L12, L11, L16, and L33, and translational such as EF-Tu, IF-3, IF-3.

5. Proteins Involved in Metabolism

Glutathione S-transferase, ferredoxin, apocytochrome c, citrate synthase, opsin, α-amylase, 6. Proteins Involved in Chemotaxis and Movement che Z, che R, pilin, flagella proteins;

7. Miscellaneous Other Proteins

Heat shock protein(s), IF-31, phycobiliprotein, allophycocyanin.

SMALL MOLECULES WHICH ARE METHYLATED OR FORMED BY METHYLATION

1. Various Metabolic Intermediates, etc.

Creatine, carnitine, nicotinamide, nicotinic acid, ornithine, betaine aldehyde, betaine, trimethylglycine, dimethylglycine, sarcosine (monomethyl glycine), glycine, vitamin $B_{12}$, ubiquinone, thiols, thiopurines, ovothiol;

2. Lipids

Phosphatidylcholine, vaccenic acid

3. Neurotransmitters

Acetyl choline, epinephrine, norepinephrine, dopamine, L-DOPA, melatonin, vanillic acid, mandelic acid, γ-butyric acid, histamine, carnosine, anserine 4. Steroid Hormones Estrogen, ergosterol (vitamin $D_3$)

5. Bacterial and Plant Molecules

Vitamin K and $K_2$ (menaquinone), tocopherol, multiple other vitamins

6. Miscellaneous Molecules

Antibiotics, natural products, mercury, lignin

With respect to signal transduction proteins and pathways, calmodulin affects the activity of a number of important cellular proteins either by binding directly as a subunit of the protein (e.g., phosphorylase kinase) or by interacting with the protein (e.g., adenylate kinase and guanylate kinase). Calmodulin affects $Ca^{++}$ levels in the cell by binding to 1–4 $Ca^{++}$ ions. The level of bound $Ca^{++}$ also dictates the relative activity of many of the calmodulin-regulated proteins. Superimposed on this modulation are two types of methylation of calmodulin which likely have a primary regulatory importance.

The first type of SAM-mediated methylation of calmodulin is at the carboxyl terminus, yielding a methylester derivative. Calmodulin is one of the major protein targets for such an esterification, and it is considered to have significant regulatory importance. For example, it has been shown that such methyl esterification reduces its ability to activate cyclic nucleotide phosphodiesterase activity.

Consistent with their regulatory role, it is noteworthy that the G proteins involved in signal transduction are also methylated at their carboxyl termini to form methyl ester derivatives, which like the calmodulin methyl ester exhibit a rapid rate of turnover.

The second type of SAM-mediated methylation of calmodulin occurs at $Lys^{115}$ to produce a trimethyllysine derivative. This modification is important since it is thought to affect the half-life, and thus the amount, of cellular calmodulin because $Lys^{115}$ is the residue targeted by the ubiquitin degradation system of the cell. This lysine receives multiple ubiquitin residues which targets the modified calmodulin for degradation. In contrast, when $Lys^{115}$ is converted to a trimethylysine derivative, calmodulin becomes completely resistant to degradation by the ubiquitin system, which would markedly increase its half life. This is of particular importance in regulation of the cell cycle, which is known to be temporally regulated by the amounts of available intracellular calmodulin.

As one of the central tenets of the present invention is the observation that methylation in general is altered in many disease states and is progressively inhibited with aging, it follows that calmodulin methylation will also be altered. This will in turn alter the $Ca^{++}$ balance within the cell and will change the properties of enzymes and structural proteins which either have calmodulin as a subunit or which are otherwise regulated by calmodulin. These proteins are listed in Table III, below. In many disease states, alteration in the activities of one or more of these enzymes will be indicative that the methylation state of calmodulin has been abnormally perturbed. Calmodulin may also be associated with protein kinase C as protein kinase C activity is inhibited by phenothiazine, an inhibitor of calmodulin binding. Also included in this list are proteins phosphorylated by kinases which are stimulated by calmodulin.

Methylation in the Modulation of Energy Metabolism

It is important to note that the trimethyllysine derivative in calmodulin has another critical role, since it leads ultimately to free trimethyllysine upon proteolysis and then to carnitine. The trimethyllysine derivative is found in over ten proteins in the. eukaryotic cell: calmodulin, cytochrome c, citrate synthase, myosin, actin, histones $H_3$ and H4, heat shock proteins HSP83 and HSP70, elongation factor-1α, ribosomal protein $L_{11}$, and α-amylase (in plants). When such proteins are degraded, they provide the cell with its only non-dietary source of free trimethyllysine. This modified amino acid subsequently is converted in a three-step reaction (one of which requires ascorbic acid) to carnitine, which has a critical regulatory role in mammalian cells in the transport of fatty acids into mitochondria.

TABLE III

A. Class I Calmodulin-Regulated Proteins
(calmodulin is a subunit of protein complex)

| | |
|---|---|
| Band-1 protein | myelin-basic protein |
| MAP-2 | phospholambin |
| fodrins (mciuding spectrin) myosins LC1 and LC2 | $(Ca^{++}/Mg^{++})$-ATPase |
| | adenylyl cyclase |
| caldesmon | myosin light chain kinase |
| lipovitellin | phosphorylase kinase |
| phosphorylase b | $Ca^{++}$-ATPase (transports $Ca^{++}$ out of cytosol) |
| calcineurin | protein phosphatase 2b |
| tau factor | inositol kinase (catalyzes transformation of |
| tubulin | inositol$(1,4,5)P_3$ to inositol $(1,3,4,5)P_4$) |
| gap-junction protein | inducible NO synthase |
| troponin-1 | |
| histones H3 and H4 | |

B. Class II Calmodulin-Regulated Proteins
(calmodulin is not a protein subunit)

| | |
|---|---|
| adenylyl cyclase | dolichol kinase |
| guanylyl cyclase | NAD kinase |
| cyclic nucleotide phosphodiesterase | dynein ATPase (regulated by $Ca^{++}$ which is |
| myosin-light chain kinase | regulated by calmodulin) |
| myosin-heavy chain kinase | phospholipase $A_2$ (activated by calmodulin in |
| phosphorylase kinase | platelets to release arachidonic acid) |
| multi-function kinases | cGMP protein kinase |
| $(Ca^{++}-Mg^{++})$-ATPdse | phospholipase $A_2$ |
| protein phosphatase 2b | tryptophan 5'-monooxygenase |
| calcineurin | succinate dehydrogenase |
| dynein | O-methyltransferases |
| ATPase | N-methyltransferases |
| NADH semi-hydroascorbate oxoreductase | constitutive NO synthase |
| NADPH oxidase | cAMP response element binding protein |
| phospholipid methylase | (CREB)* |

*CREB is phosphorylated by either of two calmodulin-dependent kinases (CaM1 and CaM2).

Although fatty acids provide the main sources of energy in the mammalian cell through oxidative phosphorylation in the mitochondria, they are not free to diffuse into the mitochondria and must be transported. Hence, fatty acids are first acylated with carnitine (generated from the trimethyllysine as above) which allows them to be transported into the mitochondria on the carnitine shuttle. Once in the mitochondria, the fatty acids are cleaved from the carnitine and then oxidized to produce ATP. The carnitine itself is transported by the shuttle back to the cytosol where it can pick up another fatty acid to repeat the shuttle process. Carnitine levels, however, are also highly regulated and such regulation provides a simple means for modulating fatty acid oxidation.

The production of energy from sugars, fats, amino acids, and ketone bodies is a highly orchestrated process which changes by the hour in mammals (and which can only be understood within the context of the SAM paradigm). When sugar is made available to a human in a morning meal containing carbohydrate, energy is produced mainly by glycolysis and the citric acid cycle. After several hours, glucose and glycogen stores are nearly depleted and alternative energy stores must be mobilized. Fatty acids will not be available as major energy sources as carnitine will not be present in large quantities, creating a situation in which the carnitine shuttle is not operative. In this case, energy will be derived in part by degrading proteins to amino acids, which subsequently are converted to acetyl CoA, pyruvate, or succinyl CoA (all of which are subsequently oxidized in the citric acid cycle to produce ATP). As these proteins are degraded, however, free trimethyllysine will be produced and converted to carnitine. Once produced, the carnitine shuttle will begin to operate, and fatty acids can be efficiently transported into the mitochondria where they will be oxidized (after conversion to acetyl CoA or succinyl CoA) to produce large amounts of ATP. The carnitine shuttle will operate until carbohydrate is again ingested. At that time, fatty acid transport and oxidation can be terminated by degradation of carnitine, and sugars can be oxidized by glycolysis and the citric acid cycle to produce the required ATP.

Although the above picture is presented in simplified form, it illustrates how methylation can be involved in the modulation of energy. Moreover, it illustrates how energy production can begin to fail as aging occurs. With age, cellular methylation levels will fall, leading to the eventual reduction in trimethyllysine levels and therefore carnitine levels. This in turn will reduce the efficiency of oxidation of fatty acids and thus increase the levels of fat within adipose tissue (as in obesity). A key small molecule in the mitochondria is ubiquinone, which receives electrons (reducing equivalents) from three pathways and transfers them into the cytochrome chain for production of ATP. The rate-limiting step in ubiquinone biosynthesis is SAM-mediated methylation. Hence, as an organism, such as a human, ages, it will make significantly less ubiquinone. Coupled with the reduced production of carnitine, this creates significant reductions in energy, potential increases in oxidative destruction of mitochondria, and increases in adipose tissue (fat) in aging humans. Thus, in a real sense, these naturally occurring small molecules become "vitamins" as we age. Consistent with this, ubiquinone has major effects in preventing heart attacks in the geriatric population. Ubiquinone also has been shown to aid in the recovery following myocardial infarction. Moreover, as will be noted below, reduced carnitine and ubiquinone levels are hallmarks of a number of diseases associated with aging such as late-onset diabetes, Alzheimer's disease, multiple sclerosis, and others.

Important Energy Relationships

Energy control and production from glycolysis falls under the methylation umbrella as described herein. Linear glycogen with α-1,4-linkages is made by glycogen synthase. After at least eleven residues are polymerized, six or seven residues are cleaved away and transferred to form a "branch" with an α-1,6-linkage. The branching enzyme requires an RNA for activity; branching itself may be RNA-catalyzed. The 31 nucleotide RNA contains 10 modified nucleotides (Korneeva et al., *Eur. J. Biochem.* 96:339–347 (1979)). Six of these modifications are SAM methylations and the remaining four consist of two pseudouridines and two dihydrouridines. Hence, cellular inhibition of methylation would be expected to alter the modification of this RNA and perhaps its activity to form branched glycogen.

The rapid mobilization of energy from glycogen is accomplished in part through the hormones norepinephrine and epinephrine. Norepinephrine levels are regulated by SAM-mediated methylation: O-methylation of norepinephrine produces normetanephrine which is excreted. N-methylation of norepinephrine converts it to epinephrine. Epinephrine in turn can be O-methylated to metanephrine, which is excreted. SAH hydrolase which regulates SAM-mediated methylations would be expected to play a major role in this regulation. Epinephrine initiates the rapid conversion of glycogen to glucose (the so-called "fight or flight" response) by binding to receptors on cells (e.g., muscle, adipose tissue and liver) and activating intracellular production of cAMP which, in turn, activates protein kinases initiating a cascade of events some of which are calmodulin-regulated.

As noted above, it has been proposed that cellular cAMP levels are regulated by binding to SAH hydrolase (and GAPDH and phosphofructokinase). In addition, cAMP reversibly inactivates SAH hydrolase in the lower eukaryote, *Dictyostelium discoidium*, and is likely to do so in higher eukaryotes. Thus, free cAM levels are regulated in part by binding to SAH hydrolase, and cAMP may itself regulate SAH activity. The foregoing indicates the existence of intertwined relationships between cAMP levels, SAH hydrolase levels and activity, and cellular methylation.

In addition, it is important to note that calmodulin is a subunit of cyclic nucleotide phosphodiesterase and is required for the activity of this enzyme. Hence calmodulin is a critical factor in regulation of intracellular cAND levels. Calmodulin stability is highly dependent on the methylation of Lys[115], as unmethylated Lys[115] is a target for ubiquitin-mediated protein degradation. In addition, methylation of the terminal carboxyl group of calmodulin may also affect its regulatory effects on cAMP phosphodiesterase,. These relationships of calmodulin with cAMP suggest fundamental interlinling relationships between four cellular components: calmodulin, cAMP, SAH hydrolase and cellular methylation.

EMPIRICAL DETERMINATION OF ABERRATIONS IN SAM PATHWAYS

As illustrated above, the known metabolic reactions which are influenced by the various SAM pathways are available for consideration in determining appropriate protocols for alleviation of conditions that affect, or are the result of, particular alterations in these metabolic processes.

However, this invention is not limited to utilizing the knowledge of metabolism related to and organized by the SAM pathways that is already available in the art. It is also possible empirically to determine which of the critical SAM-related metabolites is present at abnormal levels for a particular disease or condition, as well as to determine empirically which SAM pathways are associated with that metabolite and contribute to its aberrant level.

In one approach, a biological fluid or sample of tissue or cells is obtained from the subject organism having the disease or condition. Where appropriate, such as with tissue or cells, the sample is extracted using conventional lysing and solubilizing techniques to obtain total tissue/cell extracts, or extracts of subcellular fractions such as of the nuclear, cytoplasmic or mitochondrial material. The contents of these extracts are then assessed using any available assays or methods known in the art, for example, by HPLC or gas chromatography, and the levels of specific compounds or the activity of one or more enzymes associated with the various SAM pathways are determined. The patterns obtained are compared to those present in corresponding biological fluids of normal subjects or subjects known not to have the disease or condition being tested.

Preferably, the presence and levels of the compounds listed in Table IV, below should be measured and/or monitored. This list is not intended to be complete, as other compounds may also be measured as would be evident to one skilled in the art in light of the present disclosure. A list of the most preferred compounds is show in Table V.

Also intended to be measured and or monitored are modifications in proteins, measured as methylated amino acids after hydrolysis of purified protein or total protein. Additional modifications of proteins include mono- or poly (ADP-ribose) groups, geranylgeranyl groups, farnesyl groups, etc.

TABLE IV

| | | |
|---|---|---|
| biotin | hypusine (after protein hydrolysis) | creatine |
| folate derivatives | | phosphocreatine |
| p-aminobenzoic acid | diphthamide (after protein hydrolysis) | creatinine |
| vitamin $B_{12}$ | | carnosine |
| NAD*/NADH | wye base in tRNA (after hydrolysis) | anserine |
| NADP*/NADPH | | methylated estrogen |
| FAD | queuine | carnitine |
| ubiquinone | queuosine | ubiquinone |
| CoA | Modified nucleotides, nucleosides or bases | histamine |
| thiamine pyrophosphate | | N-methyl histamine |
| pyridoxal phosphate | 5'-deoxyadenosine and breakdown products | histidine and catabolites |
| ascorbic acid | | taurine |
| FMN | acetyl CoA | Small mol. methylation inhibitors: |
| lipoic acid | malonyl CoA | |
| retinol A | aminocyclopropane-carboxylic | 3-hydroxypyridinium |

TABLE IV-continued

| | | |
|---|---|---|
| methionine | acid (ACC) | derivative methinin |
| ATP | N-malonyl ACC | Tyrosine Catabolites: |
| | | |
| SAM | ethylene | melanins |
| SAH | homoserine lactone | L-DOPA |
| adenosine | cAMP | dopamine |
| inosine | cGMP | norepinephrine |
| homocysteine (and oxidation products) | inositol derivatives diacylglycerol, | normetanephrine epinephrine |
| cystathionine | ATP/ADP ratios, | metanephrine |
| homoserine | GTP/GDP ratios, | 3-methoxy4-hydroxy- |
| cysteine | 5-phosphoribose-1-pyro- | mandelic acid |
| glutathione (GSH/GSSH | phosphoric acid | Tryptophan Catabolites: |
| ratios) | glucose | tryptamine |
| ornithine | fructose 1,6-bisphosphate | N,N-dimethyltryptamine |
| decarboxylated SAM | Substrates/products of | serotonin |
| putrescine | GAPDH | melatonin |
| spermidine | pyruvate | picolinic acid |
| spermine | lactate acid | quinolinic acid |
| N1-acetylspermine | Substrates/products of LDH | nicotinamide |
| N1-acetylspermidine | betaine | γ-interferon-induced |
| acetylputrescine | choline | Tryptophan Catabolites: |
| spermidine-glutathione | acetylcholine, | GTP |
| hydrogen peroxide | phosphatidyl choline | tryptophan |
| methylthioadenosine | phosphatidyl ethanolamine | kynurenine |
| methylthioribosyl-1-phosphate | phosphatidyl serine | neopterin |
| adenine | trimethylysine | tetrahydrobiopterin and |
| purine intermediates | N,N-dimethylglycine | derivatives |
| AppppA | N-methylglycine | Interferon-specific Molecules: |
| | glycine, serine and ratios N-methylnicotinamide | 2-5A oligoribonucleotides. |

TABLE V

Most Preferred Compounds

| | |
|---|---|
| biotin | substrates/products of GAPDH |
| folate derivatives | betaine (trimethyl glycine) |
| ubiquinone | dimethyl glycine |
| methionine | trimethylysine |
| SAM | diphthamide (after protein hydrolysis) |
| SAH | carnitine |
| adenosine | vitamin $B_{12}$ |
| inosine | Tyrosine Catabolites: |
| homocysteine | melanins |
| cystathionine | L-DOPA |
| glutathione | norepinephrine |
| decarboxylated SAM | epinephrine |
| putrescine | Tryptophan Catabolites: |
| spermidine | serotonin |
| spermine | melatonin |
| methylthioadenosine | γ-Interferon-induced Tryptophan |
| methylthioribosyl-1-phosphate | Catabolic Pathway |
| adenine | GW |
| hypusine (after protein hydrolysis) | kynurenine |
| wye base in tRNA (after hydrolysis) | picolinic acid quinolinic acid |
| queuine | neopterin |
| queuosine | tetrahydrobiopterin |
| 5'-deoxyadenosine | Interferon-specific Molecules: |
| aminocyclopropane-carboxylic acid (ACC) | 2-5A oligoribonucleotides. |
| AppppA | |
| ethylene | |
| homoserine lactone | |

The biological fluids may be subjected to any or all of the following measurements, as appropriate:

(a) pH, which is modulated in part by lactic acid;

(b) $pO_2$ and $pCO_2$, which are modulated in part by fructose 1,6-bisphosphate and biotin-mediated carboxylations;

(c) oxidation/reduction potential; and (d) levels of any gases such as NO or ethylene.

In implementing the methods of the present invention, a number of SAM pathway ligands are used as a standard screen as a first approach in those cases where little is known about the disease state relative to SAM metabolism. This approach typically employ batch affinity chromatography procedure using microcentrifuge tube filters (for example, from PGC Scientific, Gaithersburg, Md.). It is anticipated that up to 24 different ligands can be evaluated at the same time. Depending on these results this may then be expanded if necessary. When analyzing a disease state for which more information is available, the candidate compounds can readily be selected considering the SAM paradigm presented herein. See, for example, the section on wound healing, below

AFFINITY CHROMATOGRAPHY

In addition to directly assessing biological fluids for SAM-related molecules and enzyme activities, the targets of the SAM pathway that are abnormal in diseased cells or tissues can be identified using small molecule ligands by affinity chromatography. The small molecules are chosen by virtue of their importance in the SAM-mediated control of metabolism. Generally, subsets of the following molecules, listed in Table VI, are appropriate as affinity ligands. This list is not intended to be exhaustive.

Generally, a subset of these compounds for example, six or preferably four compounds are used as affinity ligands in sequential columns. Alternatively, more than one ligand is immobilized on a single solid support. These compounds or derivatives thereof are immobilized on any solid phase support or carrier capable of binding these molecules provided that the solid phase support is not deleterious to the biochemical moieties to be bound to the afinity ligands such that the biochemical moieties can be measured or used after elution therefrom. Such affinity matrix materials are well-known in the art and include silicon oxide (glass or quartz), styrene, polystyrene, polypropylene, polycarbonate, polyethylene, divinyl benzene, dextran, nylon, amylases, natural and modified celluloses such as nitrocellulose, polyacrylamides, agaroses, magnetite and the like. Standard chromatographic techniques are used and need not be elaborated here.

TABLE VI

AFFINITY LIGANDS

| | |
|---|---|
| folate analogues | betaine (trimethylglycine) |
| vitamin $B_{12}$ analogues | dimethylglycine |
| homocysteine | estrogen |
| methionine | testosterone |
| SAM analogues | choline |
| SAH analogues | phosphatidyl choline |
| adenosine analogues | phosphatidyl serine |
| inosine analogues | carnitine |
| ornithine | lactate |
| putrescine | pyruvate |
| spermidine | fructose 1,6-bisphosphate |
| spermine | glyceraldehyde 3-phosphate |
| spermidine-glutathione conjugate, | N-methyl glycine |
| acetylspermidine and acetylspermine, | N-methyl nicotinamide |
| decarboxylated SAM, | nicotinamide |
| methylthioadenosine (and its metabolites) | quinolinic acid |
| hypusine | picolinic acid |
| 3-carboxy-3-aminopropyl analogues, e.g., | 2-5A oligomers |
| wye base and diphthamide | AppppA |
| queuine and queuosine (and precursors) | acetyl CoA |
| 5'-deoxyadenosine group | arachidonic acid |
| amino-cyclopropane-carboxylic acid (ACC) | prostaglandins |
| N-malonyl ACC | thromboxanes |
| ethylene | leukotrienes |
| homoserine lactone | retinol A |
| homoserine | β-carotene |
| biotin and analogues | vitamin D and analogues |
| cAMP | ubiquinone |
| cGMP | vitamin E (tocopherols) |
| poly(ADP)ribose | vitamin K (phylloquinone) |
| inositol | vitamin K2 (menaquinone) |
| diacylglycerol | thyroxin |
| $NAD^+$ and/or NADH | Monoamine |
| $NADP^+$ and/or NADPH | neurotransmitters |
| | |
| cystathionine | DOPA |
| cysteine | dopamine |
| glutathione | norepinephrine |
| | epinephrine |
| | serotonin |
| | melatonin |

In general, in the present method, a biological fluid from a subject having a disease or condition, or from abnormal cells of such a subject, is compared with a corresponding biological fluid from a normal healthy subject not having the disease or condition, or from normal cells. Each sample biological fluid is applied to an affinity column containing one or more appropriate affinity ligands, as above, and any material in that fluid capable of binding to the affinity ligand is allowed to absorb to the ligand. After appropriate washing steps, the bound sample material is eluted and appropriate samples are compared. By comparing the nature and concentration of the biochemical components which are retained by columns run on biological fluids from abnormal subjects with those from normal subjects, the status of the SAM pathway or pathways which is altered in association with the disease or condition can be determined.

If sequential columns are used, it is possible to focus on a small number of macromolecules (e.g., proteins) or small molecules whose levels are elevated or lowered in the abnormal sample.

For example, a first column might be loaded with spermidine as the ligand; a second with ACC; a third with biotin; and a fourth with SAH. Examination of eluates consisting of the bound components from each of these columns in sequence provide a pattern of alteration characteristic of the sample from the abnormal subject.

As an example, wound healing is discussed (see also, Example I, below). Since wound healing appears to be influenced by multiple SAM pathways, a combination of the following affinity columns would be used to compare a biological fluid obtained from a wound and from normal tissue from the same or a different subject:

(1) Biotin column. Biotin influences general growth properties (2) SAM (nitrogen analogue) column. SAM is involved in the methylation of DNA and RNA and in controlling processes such as DNA transcription and RNA translation.

(3) Ethylene antagonist column. Ethylene has growth and wound healing properties in plants which may occur in mammals, including humans.

(4) double stranded (ds) DNA and single stranded (ss) DNA columns. Specific ss DNA- and ds DNA- binding proteins are involved in timing of cell proliferation and differentiation. Differences between normal and wound samples will allow the development of appropriate treatment approaches as discussed herein, which may include more than one active compound.

Instead of, or in addition to, the affinity ligands listed above, other substances such as drugs or enzymes may also be used as affinity ligands. A non-limiting list appears in Table VII.

TABLE VII

| |
|---|
| Drugs |
| taxol, |
| colchicine |
| antiinflammatory drugs |
| salicylic acid |
| acetyl salicylic acid |
| ibuprofen |
| Enzymes |
| glucose 6-phosphate dehydrogenase |
| phosphoglycerate kinase (in primer recognition complex) |
| glycogen synthase kinase-3 |
| GAPDH |
| LDH |
| $LDH_K$ |
| pyruvate kinase |
| phosphofructokinase |
| calmodulin |
| protein kinase C, $pp60^{src}$, p36 (in primer recognition complex and primary target of $pp60^{src}$), p53, and RB protein |
| Glycolytic enzymes (specific isoforms) |

CELL CULTURE OR ANIMAL MODEL APPROACH

In addition to the methods described above based on hardwiring (affinity chromatography) and labeling, the present invention is used to evaluate SAM pathway intermediates in disease using cell culture and/or animal model approaches. This approach employs any cell line reflecting a disease state, such as a tumor cell line, or any animal model of a disease, such as autoimmune mouse strains, diabetic mouse or rat s , animals genetically susceptible to a disease, etc.

One important difference between normal and cancer cells in relation to the SAM paradigm of the present invention concerns methionine dependence. Cancer cells growing in culture, such as a long term cell line, as well as tumors growing in vivo, are almost always dependent upon methionine for their growth. In contrast, "normal" cell lines do not have this strict dependence.

In a preferred embodiment, the present invention comprises providing small SAM pathway metabolite molecules to cells in culture or to an animal model in vivo and examining the appropriate cellular responses. Typically, normal cells and cells representing the disease state (from a cell line or derived from a subject with the disease or model disease) are grown in culture. Cell growth is then tested by transferring cells to culture medium containing altered concentrations of a small molecule compound that is a SAM metabolite or is related to a SAM pathway as defined herein. These molecules will be added in a combinatorial assays which measure growth or other processes listed below. Examples of such compounds include, but are not limited to polyamines, homocysteine, MTA, folate, queuine, ethylene, biotin, glutathione, methionine and adenine. Also included in this group are any of the small molecules listed in the Tables herein.

The effects of these added molecules are assessed by examining cellular processes known to be affected in the disease state, for example, transmembrane transport, intracellular and organelle localization and processing, intracellular signalling and resultant functions such as antigen recognition. These processes are measured using conventional methods well-known in the art. In addition, the levels or concentrations of small molecule or enzymes in SAM pathways or affected by SAM pathways are measured. In this way, similar to the direct measurement, affinity chromatography and labeling approaches, the "cell growth" method described herein allows identification of a therapeutic composition or protocol which modulates metabolism of a SAM pathway and is useful in ameliorating the disease.

IDENTIFICATION OF METHYLTRANSFERASES AS THERAPEUTIC TARGETS

PCR methods permit identification of gene families by exploiting homologies among family members (Gautam, et al. (1989) *Science* 244:971–974). Little homology has been noted between methyltransferases, however, recently the SAM binding site of these enzymes has been identified over several regions of extended homology (Kagan, R. M. et al. (1994) *Arch. Biochem. Biophys.* 310:417–427; Ingrossa, D. et al. (1989) *J. Biol. Chem.* 264:20131–20139). Of the three regions of homology found (designated I, II and III), region II does not appear to have extensive homology compatible with PCR technique. By comparing the known human sequences (excluding DNA methyltransferases which appear to be in a separate class (Koonin, E. V. (1993) *J. Gen. Virol.* 74: 733–740) the consensus sequences of Regions I and III are as follows (separate rows indicate alternate amino acids at the indicated positions):

```
Region I:     I-V-D-V-G-S-G-P-G-T-I
              L-L-E-I-·-G-·-S-T-·-·
              V-·-·-L-·-A-·-M-·-·-·
              ·-·-·-·-·-·-·-A-·-·-·

Region III:   L-L-K-P-G-G-X-L-L-I
              V-·-R-F-·-·-·-I-V-L
              ·-·-·-·-·-·-·-I-A
```

Oligonucleotide primers corresponding to these regions are made using conventional methods. Primers with several thousand-fold degeneracy are preferred to target all possible methyltransferase family members. Preferred primers are those which result in a PCR product extending between Regions I and III or from region I or III to the poly A tail.

PCR protocols used are those routinely employed for identifying gene families. The DNA source can vary, and includes, for example, genomic DNA or cDNA made from mRNA obtained from particular tissue sources (Ikayama-H. et al. (1987) *Methods Enzymol.* 154:3–28). Several combinations of oligonucleotides are used. For example, the sense strand encoding Region I and the antisense strand for region III are combined to identify unique PCR products. Alternatively the sense strand encoding region III and oligo dT are used for amplifying the cDNA to the poly A tail.

In one embodiment, the resultant PCR products are individually cloned and verified as being potential targets based on their sequence. Alternatively, if the product is observed to be a discrete band on an agarose gel, the PCR mixture is used in the form of a library as a probe set. By using the PCR product as a probe, libraries can be screened to identify the fill length cDNA encoding a methyltransferase. The screening is preferably performed by random primer labeling of the PCR products and their use as hybridization probes.

The PCR products are used to identify methyltransferase genes from various tissues, both normal and diseased (e.g., tumors). It is expected that some methyltransferases are expressed in a tissue-specific manner, and that these enzymes are or upor down-regulated in a given disease state. For example, immunosuppressive agents such as methotrexate and deoxycoformycin affect SAH levels. In fact, inhibitors of SAH hydrolase have immunosuppressive activity (Wolos, J. A., et al., *J. Immun.* 150: 3264–3273). Hence, activation of T-cells is thought to involve the induction of methyltransferase activity, whereas immunosuppression is achieved by raising SAH levels, thereby inactivating the methyltransferase. Therefore, according to this invention, cDNA from activated and non-activated T-cells is screened for PCR products as described above. Any differences observed may be related to the one or more methyltransferase enzymes involved in T-cell activation.

(a) In another embodiment, the PCR products described above are used in Northern analysis to probe mRNA from activated versus non-activated T-cells to evaluate up- or down-regulation of methyltransferase gene expression. The methyltransferases so identified are cloned using conventional methods employing the PCR products and investigated as therapeutic targets. The way in which a therapeutic target is evaluated depends on the disease state. In the case of upregulation of a methyltransferase, for example, an immunosuppressant, an inhibitor of the enzymatic activity of the particular methyltransferase is made by conventional methods. The potential of this inhibitor to suppress immune response or T-cell activation is analyzed using well-known assay methods for characterizing immune responsiveness in vivo or immune reactivity, in particular T cell activation, in vitro.

THE SAM PARADIGM AND PARTICULAR DISEASES OR CONDITIONS

A. Wound Healing

Application of the methods of the present invention to identify a therapeutic composition or protocol which is useful in treating a disease state is discussed below in relation to wound healing. The process of wound healing can be divided into three phases, inflammatory, fibroblastic and maturation phases (Bryant, *J. Enterostom. Ther.* 14:262–266 (1987)). SAM pathway intermediates or metabolites modulated by SAM pathway intermediates are related to wound healing in a number of ways.

Mouse fibroblast L-cells were adapted to grow on a chemically defined medium in the absence of serum. When biotin was excluded from this medium, this medium proved to be incapable of sustaining cell proliferation (Haggerty et al., *Biochem. Biophys. Res. Comm.* 34:812–815 (1969)). Additionally, biotin stimulates production of proteins that have growth factor properties in Rous sarcoma virus-transformed BHK cells (Mosekowitz et al., *Ann. NY. Acad. Sci.* 447:212–221 (1985)).

Biotin, an essential vitamin, is supplied exclusively from the mother to the fetus. Deficiency of biotin in pregnancy leads to impaired fetal growth and development. Rapid deposition of collagen without scar formation have been reported in fetal wounds (Longaker et al., *J. Pediat. Surg.* 25:63–69 (1990)). These observations suggest an important role for biotin in cell growth and wound healing.

Methionine powder is known to be beneficial to wound healing (Salim, *Clin. Exp. Dermat.* 17:427–432 (1992)). DL-cysteine and DL-methionine-methylsulphonium chloride, stimulate the healing of venous ulcerations.

It is well known in the plant literature that ethylene plays an important role in wound healing. The presence of ethylene has been observed in studies of animals, suggesting a similar role in mammalian tissue.

Functionally different, alternatively spliced fibronectin isoforms may be involved in the maintenance of normal cornea as well as in wounding, where the isoforms are primarily synthesized in the stroma rather than in the epithelium (Vitale et al., *Invest. Ophthalmol. Vis. Sci.* 35:3654–3672 (1994)). Macrophages and fibroblasts express alternatively spliced embryonic fibronectins during cutaneous wound healing, indicating that alternative splicing can function as a modulatory or on/off switch for crucial regulatory proteins. Methylation may play a role in alternative splicing as discussed above.

Expression of protooncogenes c-fos and c-myc is involved in the mechanism of polyamine-stimulated healing of gastric mucosal stress ulcers. This healing process was significantly inhibited by difluoromethylornithine (DFMO), an inhibitor of polyamine synthesis. (Wang et al., *Am. J. Physiol.* 266:G878–86 (19994)).

The $Ca^{++}$/calmodulin system has been implicated in the early stages of wound healing (Mizumoto, *Hokkcaido Igaku Zasshi* 62:332–345 (1987)). The methyltransferase enzyme that catalyzes the trimethylation of $Lys^{115}$ in sheep brain has been isolated (Han et al., *Biochemistry* 32:13974–13980 (1993)). Des(methyl)calmodulin is a substrate for ubiquitination and subsequent ATP-dependent proteolysis, whereas N-methylated calmodulin is not degraded thus providing a mechanism for the conservation of calmodulin. The dynamics of calmodulin protein levels, calmodulin methylation and calmodulin-binding proteins during plant growth and development has been studied (Oh et al., *Arch Biochem. Biophys.* 297:28–34 (1992)). Calmodulin methylation is low during the lag and early exponential stages, but increases substantially as exponential growth proceeds and becomes maximal in the post-exponential phase. This suggested to the present inventors that (a) calmodulin methylation is regulated by the state of cell growth, and (2) calmodulin and its target protein are modulated during early plant development. Similar regulation is expected in mammalian cells. Protein knase activity is modulated by enhanced $Ca^{2+}$ binding to calmodulin (Uyama et al., *Pflug. Arch.*, 426:363–370 (1994)). Protein kinase C inhibitors inhibit corneal re-epithelialization in the rat (Hirakata et al., *Invest Ophthalmol. Vis. Sci.* 34:216–221 (1993)).

A number of growth factors enhance wound healing, including epidermal growth factor (EGF) (Heck et al., *J. Biol. Chem.* 267:21277–88 (1992)), insulin-like growth factor (ILGF) (Olanrewaju et al., *Am. J. Physiol.* 263:E22–26 (1992)), platelet-derived growth factor (PDGF), transforming growth factor β (TGFβ) and basic fibroblast growth factor (bFGF) (Hudson-Goodman et al., *Heart & Lung*, 19:379–86 (1990)). As described above, EGF receptor activity is regulated by queuine (Langgut et al., supra) and biotin stimulates production of proteins having properties of growth factors (in Rous sarcoma virus-transformed BHK cells; Moskowitz et al., supra). These observations suggests that growth factors are regulated by SAM pathway intermediates.

The SAM paradigm of the present invention teaches that SAM pathway intermediates will play an important role in regulation. The foregoing points to potential regulatory ability of SAM pathway intermediates in connection with wound healing. Thus, SAM, ethylene and biotin will play central roles in wound healing and their measurement and manipulation serves as the basis for diagnosis, design of therapeutic regimens and therapy of wounds, as exemplified below.

When wounding occurs, the inflammatory phase (Bryan, supra) serves primarily to control bleeding and prevent bacterial invasion beyond the wound site. Initially, the injured capillaries undergo thrombosis which facilitates homeostasis. This essentially devascularizes the wound edges and to some degree causes cellular ischemia. During this process, surrounding capillaries become more permeable and leak components necessary for repair into the wounded area. Since wound healing increases the demand for precursors for the repair of damaged tissue in general, and based on the foregoing description, it is assumed that the concentrations of precursors and SAM intermediates will be low in the wounded area. Therefore, the wound is treated by topical application of the appropriate SAM pathway intermediates to the wounded area to promote healing. The following SAM intermediates and related ligands that will play a role in the acceleration of wound healing include, but are not limited to, the following compounds:

SAM, biotin, methionine, ethylene, polyamines (putrescine, spermine, spermidine), ornithine, arginine, 1-aminocyclopropanecarboxylic acid (ACC), queuine, queuosine, calmodulin, fibronectin, protein kinase C, EGF, ILGF, PDGF, TGFβ and bFGF.

According to the present invention, these intermediates are arranged into two data sets or priority lists. The first one is of higher priority and includes SAM pathway intermediates which may be prioritized internally based on the fact that SAM splits into different pathways. Thus, in a preferred priority list, SAM is listed first followed by other intermediates in different pathways, followed by building blocks of SAM pathway intermediates.

First Priority List for Wound Healing:

SAM, decarboxylated SAM, biotin, ethylene, 1-aminocyclopropanecarboxylic acid (ACC), polyamines (putrescine, spermine, spermidine) and their derivatives (e.g., acetylated forms), ornithine, arginine, methionine, adenosine, queuine, homoserine lactone The second priority list or data set comprises a group of intermediates which enhance wound healing, and are considered, according to the present invention, to be regulated by SAM pathway intermediates. Internal prioritization within this group is preferably headed by those intermediates which are known to be modified or influenced by SAM pathway intermediates.

Second Priority List for Wound Healing:

calmodulin, fibronectin, protein kinase C epidermal growth factor (EGF), insulin-like growth factor (ILGF), platelet-derived growth factor (PDGF), transforming growth factor β (TGF-β) and basic fibroblast growth factor (bFGF), nicotinamide, inositol.

Any one or more of the following approaches is used in accordance with the present invention to determine which metabolite or pathway deviates the most from normality. While the description focuses on wounds, the general approach is used according to the present invention for diagnosis of treatment of any of the disease states described herein. When used for other diseases, the appropriate biological fluid is obtained, as is understood by those skilled in the art.

a) Direct determination of concentration of metabolites in a normal fluid or a wound fluid performed using conventional methods well-known in the art.

b) Indirect determination of the concentration of metabolites in a normal fluid or wound fluid. This can be can be performed in a number of ways:

i. Assay all the compounds in the first priority list, individually, in a screening model, such as the wounded mouse model described herein, and measure whether wound healing is promoted, inhibited or unaffected.

ii. Assay select mixtures of the compounds from the first priority group in the screening model and measure the effect on wound healing. If a stimulatory effect is observed, the devolution approach is used to break down the complex mixture to its individual components to determine which are the active components in the mixture. This is the approach followed in Example I, below.

(c) Use the compounds from the first and second priority groups as ligands immobilized to a solid support to determine which intermediates contribute to accelerated wound healing. An example of this method follows:

i. A member of the first priority group is immobilized as an affinity ligand on a solid support and tested for interaction (binding) with intermediates from normal (control) fluids and wound fluids. In brief any binding partner intermediates for the immobilized ligands are permitted to absorb to the affinity matrix, followed by high salt elution.

Two salt concentrations are preferably used for the elution. One is a moderate salt concentration (about 0.3M) and then a high salt concentration (about 0.8M). The aim is to fractionate the molecules retained on the column, into two fractions, the first fraction representing low affinity binding compounds and the second fraction containing high affinity binding compounds. In practice it is expected that more than one compound will be present in each fraction. Affinity chromatography is a well established procedure in the art. For a description of the theory and methods to practice this technique, see, for example, Dean et al. (Eds.), *Affinity Chromatography*, IRL Press, Washington D.C., 1985.

The compositions of the eluates of control and wound fluids are analyzed and compared, for example, by electrophoresis.

ii. One or more affinity ligands from the second priority group is immobilized on a solid support and tested for interaction (binding) with intermediates from normal (control) fluids and wound fluids. The method described above is used. In this case however, in addition to high salt elution, additional column evaluation is performed. In particular, SAM pathway intermediates such as, for example, SAM or biotin are used to elute bound material in a specific manner. In addition, elution can be performed using known intermediates from "non-SAM pathways," for example, cAMP, cGMP, $NAD^+$, NADH, FAD, etc.

The results obtained as above will allow identification of various types of abnormalities, which can then lead to the therapeutic approaches presented below.

(a) Abnormally low or high SAM pathway intermediates;
Treatment entails adjusting concentrations of the abnormal intermediate or intermediates.

(b) Abnormally low or high concentrations of specific binding proteins;

i. If the binding protein is an enzyme, inhibit or stimulate its activity ii. Develop better or more specific inhibitors, preferably by the combinatorial chemistry approaches.

iii. If the protein is a binding protein such as a receptor molecule, use a binding assay to develop compounds which modify binding, again preferably with combinatorial chemistry.

Once a determination has been made as to which pathways or intermediates should be stimulated or inhibited, it is preferred to target a shorter list of SAM pathway intermediates for treatment strategies. In the case of wound healing (see Example I, below), preferred targets are biotin and ACC.

The concentrations of the compounds selected for a therapeutic formulation as above are optimized using standard dose-response studies in an appropriate model system. For example, to analyze and develop therapeutic strategies for wound healing a puncture wound mouse model is preferred (and is exemplified in Example I, below. Other in vivo or in vitro models known in the art for wound healing may also be used, as described herein.

MOUSE PUNCTURE WOUND MODEL

Mice are divided into appropriate test and control groups. The mice are anesthetized by intraperitoneal injection of a general anesthetic and the upper back fur is clipped and the skin on both sides washed with sterile saline.

Preferably, wounds are placed on the upper back to minimize removal of the wound-healing ointment by licking. Using an ethanol-sterilized punch or trochar, one wound approximately 3 mm diameter is made on the upper part of the back by lifting the skin away from the body and punching through the skin between the mouse's body and the fingers of the investigator. This results in two puncture wounds on the mouse's back separated by about 1–2 cm.

The test therapeutic composition, in a topical formulation, preferably in ointment, is applied immediately following wound incision. A treatment composition (or control vehicle) is applied daily, preferably four at least about 7 days, with a sterile swab. The healing is evaluated by a "blinded" observer. Further evaluation may be performed by histologic examination of tissue obtained by biopsy or autopsy.

RAT BURN WOUND MODEL

In another preferred model, a thermal wound of uniform size, for example, 1 cm×1cm, is induced on the back of ether-anesthetized rats, for example, 12-week old Fisher rats, using an iron of appropriate size which has been flame-heated or heated by a heating element with thermocouple.

Following induction of the wound, the vehicle alone, or the therapeutic composition being tested is applied to the wound. The therapeutic composition or vehicle is reapplied twice daily. At the end of two days one group of animals is sacrificed and the wounds excised for histological analysis. In other group of animals, the wounds are treated for four to six days, the animals sacrificed and the wounds excised for histologic analysis.

After appropriate fixation, sectioning and staining, the wounds are examined for:

(1) the presence and extent of migration into the wound of fibroblasts, blood vessels and epithelial cells, observed as the formation of granulation tissue. A subjective scale of 0–4 may be used to score the reactions; and (2) the presence of inflammatory cells (neutrophils, lymphocytes and mononuclear cells), which may be scored using a subjective scale of 0–4.

The individual examining the wound histology is preferably blinded to the source of the tissue or the treatment administered to the wound.

Each treatment group, including a control of carrier alone, preferably comprises at least 6 animals.

LARGE ANIMAL MODEL: PIG BURN WOUND

Tests similar to those described above for rats are performed in large animals, preferably pigs. The wound is created by excising a 3 cm×3 cm area of epidermis and dermis under anesthesia. The test compounds are then applied, as above, twice per day and the wound excised after 2, 4, or 14 days for histologic analysis, as described above. Smaller groups of animals are generally used in these studies (3–5 animals per treatment group).

If a therapeutic composition promotes or accelerates wound healing then one will observe, relative to controls:

(1) fewer leukocytes (neutrophils and monocytes) in the wound; and (2) increased numbers of fibroblasts, blood vessels and epithelium in the healing wound.

IN VITRO WOUND ASSAYS

In a preferred embodiment, wound assays are performed as described by Shleef et al., *Tissue Cell* 14:629–636 (1982). Cells, for example, human umbilical or saphenous vein endothelial cells, dermal fibroblasts, etc., are cultured in Medium 199 containing in 10% fetal bovine serum until they form confluent monolayers, for example, in 12 well culture plates. The confluent monolayers were wounded with a razor blade after 60 minutes of treatment with mitomycin C (10 μg/ml). The cells are rinsed several times and the test compounds are added to replicate wells. Cell migration into the wound is assessed at various times thereafter by phase contrast microscopy using an inverted microscope. Quantitation may be performed by aligning the original edge of the wound with the "0" line on a 10×10 grid-reticle and the number of cells in each of the 10 rows defined by the reticle are counted.

Wound assays may also be performed as described by Sato et al., 1988, supra). Briefly, confluent monolayers of endothelial cells, for example human umbilical vein endothelial cells or bovine aortic endothelial cells, growing in 35 mm dishes are washed with phosphate-buffered saline (PBS), wounded with a razor blade, and washed again with PBS. The cells are incubated in medium, preferably modified MEM, containing 0.1% bovine serum albumin for about 20 hr at 37° C., and the cells are fixed preferably with absolute methanol and stained with Giemsa stain. Cells that migrate from the edge of the wound are counted in successive 125 Tm increments at 100× using a light microscope with an ocular grid. Several, preferably at least six, different fields, are counted and the mean cell number is determined.

The therapeutic composition being tested is added at the desired range of concentrations and analyzed for its effects on cell migration relative to an appropriate control vehicle.

B. Cancer

Overview of Methionine Metabolism and Cancer

Of the 20 amino acids, methionine and other amino acids (cysteine, lysine, threonine, isoleucine, leucine, valine, phenylalanine, tyrosine, tryptophan and histidine) are required in the human diet, since the genes encoding their de novo biosynthetic pathways have been lost during evolution. Cysteine and tyrosine can in fact be derived from methionine and phenylalanine, respectively. Homocysteine can replace methionine in the diet when either of two conditions are satisfied: (1) folic acid and cobalamin (vitamin $B_{12}$) are supplemented, or (2) choline or betaine are supplemented. This implies two pathways for production of methionine from homocysteine, one involving folate and cobalamin and the other choline and its catabolites (betaine). The folate system is found in all tissues, whereas the choline/betaine system is found at high levels in liver and kidney. Hence this second system appears to be a system for the disposal of homocysteine, which is deleterious at high concentrations and is associated with atherosclerosis).

The key steps in the two pathways of methionine synthesis are:

Pathway 1:

5-methyl FH4 + cobalamin → methyl-cobalamin
methyl-cobalamin + homocysteine → cobalamin + methionine Pathway 2:

choline + betaine aldehyde → betaine
betaine + homocysteine → dimethylglycine + methionine
dimethylglycine + $FH_4$ → methylglycine + 5,10-methylene $FH_4$
methylglycine + $FH_4$ → glycine + 5,10-methylene $FH_4$
glycine + $H_2O$ + $FH_4$ → $NH_4$ + $HCO_3$ + 5,10-methylene $FH_4$
5,10-methylene $FH_4$ → 5-methyl $FH_4$
5-methyl $FH_4$ + cobalamin → methyl-cobalamin
methyl-cobalamin + homocysteine → cobalamin + methionine.

Homocysteine is a precursor to SAH. SAH, in turn, is an inhibitor of the methyltetrahydrofolate-dependent methionine synthetase, while SAM is a promoter of this activity. Methionine is also made in the salvage pathway involving MTA Diminished folate status and excessive alcohol intake, which may decrease SAM levels, could induce hypomethylation of DNA and consequently promote colorectal cancer (Giovannucci et al., *J. Natl. Canc. Inst.* 85:875–885 (1993)).

Cancer cells often display disruption in methionine metabolism. Methionine supplementation has chemoprotective effects against cancer, illustrating a link between cancer and methionine metabolism. All normal human cells are "methionine independent" and are able to grow without methionine when supplemented with homocysteine, folate and cobalamin. Most cancer cells are "methionine dependent", further indicating a relationship between methionine metabolism and oncogenic transformation. Methionine is needed for SAM synthesis and SAM-dependent processes. As stated above, cancer cells undergo aberrantly high levels of transmethylations. Cancer cell lines are methionine-dependent either (a) because of reduced availability of endogenously synthesized methionine for SAM formation or (b) because SAM utilization is so high that the endogenous formation of methionine is not able to keep up, or (c) because the import of cobalamin is disrupted in some cancer cells. Thus, important methylation reactions needed for regulation go unattended. Aberrant methylation reactions and polyamine synthesis may alter genomic stability, gene expression and cell proliferation (Gatton-Umphress et al., *Hosp. Pract. Off. Ed.* 28: 83–85, 89–90 (1993)).

1. Methylation and SAM Pathway No. 1

Methylation of DNA in cancer cells is typically reduced. Comparisons between normal and neoplastic tissues from the same patient showed a decrease in methylation in a specific CCGG site in the third exon of c-myc through the progression from normal via dysplastic to neoplastic and metastatic tissue (Sharrard et al., *Br. J. Cancer* 65:667–72 (1992)). In hepatomas induced in rats by prolonged methyl-deficient diet, induced methylation patterns of c-Ki-ras and c-Ha-ras were abnormal (Wainfan et al., *Cancer Res.* 52:2071 s–2077s (1992)). In contrast, methylation of RNA, proteins and small molecules is generally aberrant in cancer cells. As stated above, the diphthamide group on eF-2, which is modified post-transcriptionally by two SAM pathways, is essential for activity (Omura et al., *Eur. J. Biochem.* 180: 1–8 (1989). This may serve as a target for stopping the proliferation of cancer cells.

2. Polyamines and SAM Pathway No. 2

Malignant cell proliferation is associated with an increase in intracellular polyamine metabolism which appears to be in equilibrium with extracellular circulating polyamine compartments. Furthermore, circulating polyamines help promote malignant cell proliferation and metastatic dissemination (Moulinoux et al., *Cell Mol Biol.* 37:773–783 (1991)). The mean of total polyamine levels in the urine of normal and cancer patients were 2.01 and 44.74 g/mg creatine internal standard, respectively, as determined by capillary gas chromatography (Jiang, *Biomed. Chromatogr.* 4:73–77 (1990)). As stated above, polyamines can function as switches, as in the modification of eIF-5A with spermidine, which is subsequently modified to hypusine (Park et al., *Biofactors* 4:95–104 (1993)). As with diphthamide, this is an appropriate target to stop proliferation of cancer cells.

3. 3-Carboxy-3-Aminopropyl and SAM Pathway No. 3

Donation of a 3-carboxy-3-aminopropyl group can play a role in cancer by two or three routes: (a) formation of Wye base; (b) formation of a diphthamide derivative; or (c) possibly modification of pseudouridine in 18S mRNA Tumor-specific tRNAs are aberrantly modified in the Wye base (Kuchino et al., *Nuc. Acids Res.* 10:6421–6425 (1982)). This modification is essential for fidelity in reading amber stop codons. Thus, loss of this fidelity in cancer cells may result in translation of unique sets of proteins by a readthrough mechanism.

Formation of the dipthamide modification also occurs through SAM Pathway No. 3. This modification is essential for protein translation but has also been tied to proliferation. Uncontrolled proliferation is the hallmark of the cancer cell.

4. Queuine and SAM Pathway No. 4

Another tumor-specific tRNA formed by under-modification of hypermodified nucleosides located in the anticodon loop is queuine. Queuosine, which is located in the first position of the anticodon of $tRNA^{Phe}$, is partly or completely replaced by guanosine in all tumor cells tested. Administration of queuosine to tumor-bearing mice resulted in complete conversion of G-tRNA to QtRNA in tumor cells (Nishimura et al., supra). In one case, the tumor actually shrunk following addition of Q (Katz et al., 1980, supra). This modification in specific tRNAs acts to increase the fidelity of reading of stop codons as stated above for Wye base.

5. 5'-Deoxyadenosine Radical and SAM Pathway No. 5

It has been recognized for some time that cancer cells have impaired respiratory capacity associated with elevated rates of glycolysis. (Lichtor et al., *J. Neurosurg.* 67: 336–340 (1987)). Normal fibroblasts deprived of oxygen showed several distinct biosynthetic and metabolic alterations (Freitas et al., *Anticancer Res.* 14: 1097–1102 (1994)), consistent with the normal role of these cells in the early stages of wound healing where invasiveness across normal tissue boundaries is an important property shared with certain malignant cancer cells. One of the earliest effects of the fibroblast response to anoxia is expression of an anoxic shock protein $LDH_k$, which displays lactic dehydrogenase activity.

Tumor cells endure hypoxia for surprisingly long periods (Freitas et al., supra). Hypoxia protects cells from most oxygen-dependent therapies; reoxygenation after prolonged hypoxia resulted, in culture, in cell variants with enhanced drug resistance and metastatic potential. In lower eukaryotes, pyruvate formate lyase (PFL) is switched on during anaerobic conditions (San-Martin et al., *J. Gen. Microbiol.* 138:987–996 (1992)). SAM Pathway No. 5 is involved with this radical-catalyzed enzyme. Assuming that evolution is conservative, it is suggested that this SAM pathway plays some role in anaerobic reactions in higher eukaryotes. Ribonucleotide reductase, catalyzed by a similar radical mechanism plays a central role in the conversion of ribonucleotides to deoxyribonucleotides in eukaryotes (Stubbe, *Adv. Enzymol.* 63:349–418 (1990), indicating the possibility that this mechanism based on SAM Pathway No. 5 also operates in mammals.

6. Ethylene and SAM Pathway No. 6

Ethylene production is increased five fold in cultured tumor cells relative to control normal cultured cells.

7. MTA and Homoserine Lactone and SAM Pathway No. 7

Although this pathway has not been extensively explored, cleavage of SAM to MTA and homoserine lactone could play a major role in cancer. For instance, this pathway could be a major way of regulating SAM levels for proliferation or other regulated events. MTA levels are also regulatory. MTA is the primary source of adenosine for the cell. It is a suicide inhibitor of SAH hydrolase and an inhibitor of spermine, spermidine and PRPP synthase. Thus, the cell must regulate MTA efficiently and reuse it for regeneration of adenosine and methionine.

A population of cancer patients has high levels of MTA in the serum. In addition, MTA disposal is often disrupted in cancer cells. A correlation may exist between aberrations of MTA disposal and those few cancer lines that show methionine independence. Those methionine-independent cancer lines could affect SAM through the recycling instead of the synthesis pathway. Thus, a new classification of cancers could be based on these analogies.

Homoserine lactone also plays important roles in integration of plasmid DNA in lower organisms. It may likely have a similar transforming effect in human cells.

8. Biotin and SAM Pathway No. 8

Human cancer cells (HeLa cells) have a nutritional requirement for biotin (Dakshinmurti et al., *J. Cell. Physiol.* 107:427–438 (1981)). The growth rate of mouse leukemic cells (L5178Y) was impaired when the cells were cultured in biotin-deficient medium. Chromosomal disturbances have been observed in cells growing in the absence of biotin (Pienkowska et al., *Biochem. Biophys. Res. Commun.* 66:1024 (1975)). Biotin stimulated the proliferation of G1-arrested Rous sarcoma virus-transformed BHK cells in modified Eagle's medium (Cheng et al., *J. Cell. Physiol* 113:487–493 (1982)). Biotin, like the gas NO, stimulates GMP cyclase to form cGMP (*Mol. Cell. Biochem.* 60:109–114 (1984)). cGMP has important regulatory effects on the cell. For example, it stimulates RNA polymerase II activity. It is noteworthy that calmodulin and $Ca^{++}$ may regulate the activity of cGNT phosphodiesterase and thus, the concentration of cGMP (Appleman et al., *Adv. Cycl. Nucl. Res.* 5:153–162 (1975)).

OTHER DISEASES AND CONDITIONS

A number of other diseases and conditions are associated with changes in SAM pathways and intermediates. These can be examined using the approaches described above for wounds and cancer in accordance with general teachings herein. These are discussed in the Example sections, below and include Parkinson's disease, depression, manic depression, atherosclerosis and cystic fibrosis.

COMPUTER-BASED ANALYSIS OF BIOCHEMICAL REACTION SYSTEMS

In order to analyze and model the hierarchy of biological processes and interactions and simulate its behavior in normal and abnormal function, it is necessary to integrate a wide range of data and observations. The conventional development of a model of a biological pathway requires the measurement of the component enzyme reaction kinetics, in vitro, and the generation and solution of the composite set of differential equations (R. J. Leipold et al.,

*J Biol Chem* 270: 25383–25387, 1995). This approach can be limited by the experimental difficulties in the isolation and purification of component enzymes which can lead to incomplete observations, measurements made under varying experimental (and non-physiological) conditions and variability in the accuracy of the measurements.

Michael N. Liebman and colleagues have been developing approaches to study functional relationships to enable their uniform analysis using generalized systems methods, including Petri Nets (Reddy, V. N. et al., *Comput. Biol. Med.* 26:9–24 (1996)) and stochastic activity nets (SANs) and have applied these two methods to the analysis of an autolytic enzyme activation pathway. This permits extension of the analysis to the impact of modulating enzyme activity by genetic events.

According to the present invention, these methods are applied to model and evaluate the interactions among macromolecules within the eight SAM pathways to assist in the development of models for analysis of disease processes related to these pathways and to assess risk and evaluate potential efficacy for therapeutic agents which impact on these pathways, and through them on central regulatory reactions such as methylation reactions.

Liebman and colleagues initially used as an example of a biofeedback mechanism the activation of trypsinogen to trypsin, and both its autoactivation and its autocatalytic removal by trypsin.

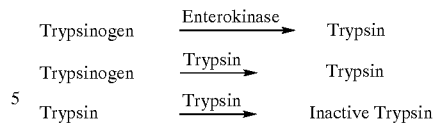

This can be used as the basis for pathways of greater complexity such as the SAM pathways described herein. Liebman and colleagues compared the Petri net and stochastic activity net (SAN) models in terms of their construction and operation, as well as the ability to perturb the model of the normal state to provide information about genetically or biochemically modulated enzyme activity.

Petri Nets

Petri nets are a graphical and mathematical modeling tool first introduced in 1962 (C. A Petri. *Communication with Automata*, New York: Griffiss Air Force Base, Technical Report RADC-TR-65-377, vol. 1, suppl. 1, 1966; see also T. Murata, Proc. IEEE 77:541–580, 1989, for a detailed discussion). The fundamental concept involves the representation of a dynamic process in terms of discrete events which can be successively monitored during process simulation to evaluate the flow of material or flux through the system. Many implementations of these tools have been used to model different types of systems, including real-time systems (W. E. Evanco et al., *Intl J Computer Simul.* 5:85–106, 1995), chemical engineering processes (H. M. Hanisch, Computers and Chem. Eng 16:1–10, 1992), and manufacturing systems (M. D. Jeng et al., *IEEE Transactions on Systems, Man, and Cybernetics*, 23:301–312, 1993).

Petri nets comprise three primary elements: (1) "nodes," which include both "places" and "transitions;" (2) "directed arcs," which connect places and transitions; and (3) tokens, which represent the discrete quantities of material at a given place. Places are used to collect tokens, elements used to represent what is flowing through the system, and transitions move tokens between places.

Figure 13:
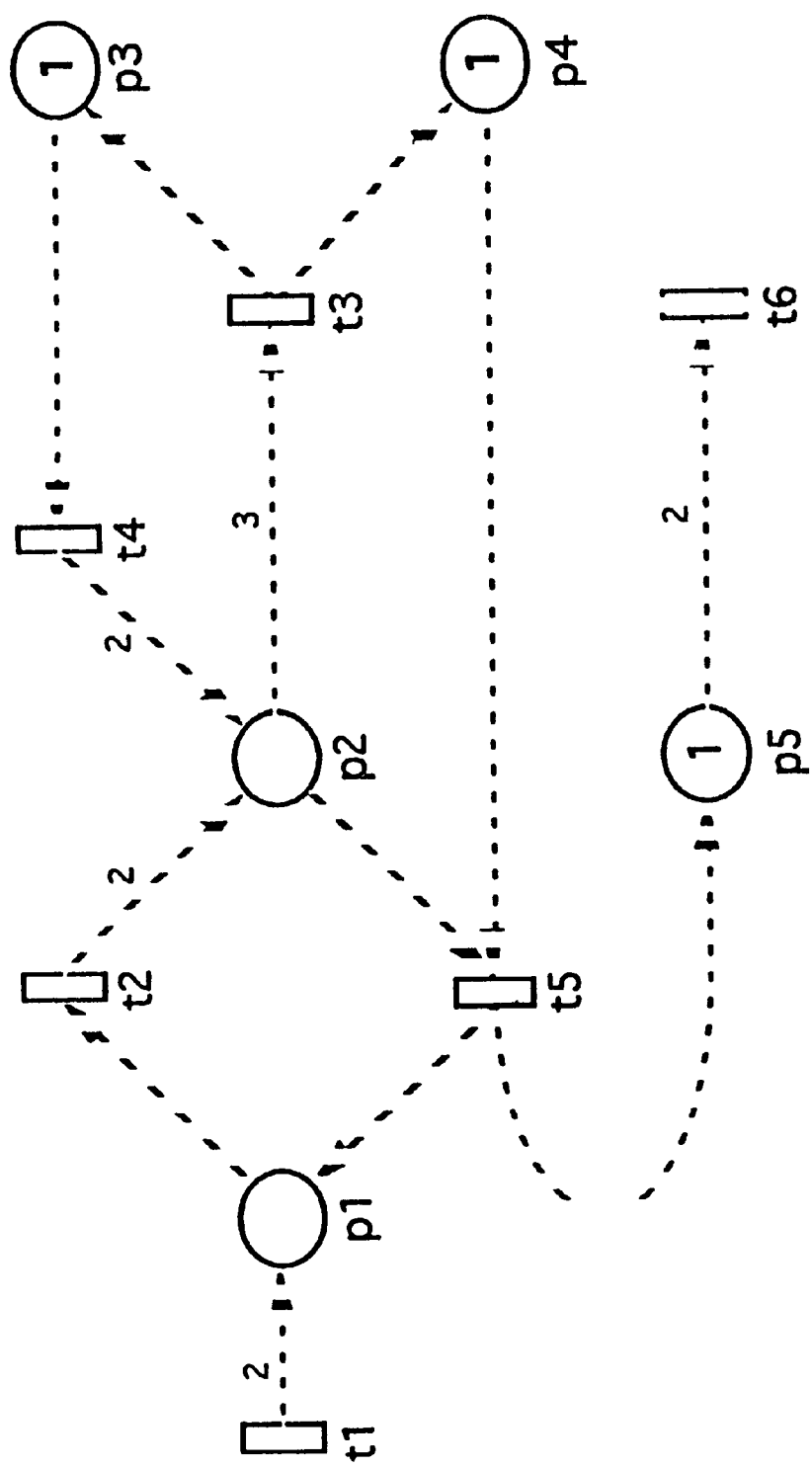
FIG. 13 is a schematic illustration of a Petri net graph with places, transitions and arcs.

A Petri net system with its places, transitions, arcs, and tokens is depicted in FIG. 13 (FIG. 1 of Reddy et a., supra). The places are represented by open circles and are labeled p1–p5. The transitions are represented by rectangles and are labeled t1–t6. Tokens are represented as the numbers within places. Finally, the places and transitions are connected together by means of directed arcs. Each of these arcs dictates token flow with respect to direction and associated weight of transfer. The numbers associated with specific arcs represent their weight, such that if an arc has a corresponding arc weight of two, then two tokens are moved between nodes along that arc. Arcs without designated weights are assigned to an arc weight of one.

Token flow occurs between places as dictated by whether the corresponding transition is appropriately enabled. That is, if the number of tokens in the input place(s) is greater than or equal to the associated arc weights connecting the input place(s) to the transition, then and only then, is a transition enabled to transfer tokens. This is the primary rule for token movement in Petri nets. In FIG. 13, transition t4 is enabled because the number of tokens indicated in its corresponding input place, p3, is equal to the arc weight connecting the input place to the transition. Thus, transition t4 is enabled to take one token from place p3 and put two tokens in place p2. In addition to transitions which have both input and output places as do transitions t2–t5, special instances exist where a transition is connected only to an input place or an output place. These transitions are termed as sink transitions and source transitions, respectively, and act to continuously remove tokens (i.e., sink) from or supply tokens (i.e., source) to the network. In FIG. 13, transition t1 functions as a source transition and transition t6 functions as a sink transition.

Transition firing or execution in Petri nets can be performed by distinct sequential and parallel execution. Sequential execution occurs by executing one enabled transition during each cycle through the model. The Petri net in FIG. 13 contains two enabled transitions, t1 and t4. The first cycle through the system would cause only one of these two transitions to move tokens, the choice of which could be determined either manually or randomly. Parallel execution, on the other hand, occurs by firing each enabled transition during each cycle through the model. Again in FIG. 13, transitions t1 and t4 are enabled to fire, therefore executions occur at both transition sites. If one place acts as an input for more than one transition, for example place p2, and both transitions are enabled, then only one of the transitions will fire, and this execution can be performed manually or randomly. Thus, a unit of execution for a Petri net, also known as a "step," is a single transition execution for sequential firing and execution of all enabled transitions for parallel firing.

Petri nets possess additional mathematical properties which are of particular value in developing their application to qualitative biological modeling, namely, structural reduction and extendibility, reachability and liveness.

The implementation of Petri nets can be accomplished by the Petri Net Simulation tool, PNS, version 1.0, produced by M. Ancutici and T. Braunl of the University of Stuttgart.

Liebman and colleagues found that their initial Petri net modeling with PNS provided insight into the requirements for their productive use as an appropriate tool for modeling biological pathways. During the process of constructing and analyzing Petri net models of biological pathways, several functional requirements surfaced which suggested expanding the tool development to include additional related methodologies, e.g., stochastic activity nets.

Petri Net Modeling of Biological Pathways

The concept of modeling biological pathways with Petri nets focuses on the specific interactions between molecules and the stoichiometry of these interactions. These relationships form the basis for modeling a specific pathway. An initial Petri net model is constructed based on this analysis and evaluated for its performance and compared to actual experimental results. For the trypsin reactions, above, the model developed by Liebman and colleagues comprised four places, each representing a separate molecular species; three transitions represented the three reactions involved; and the directed arcs connected the places and transitions in the stoichiometric ratios as they are presented. The model was initialized with 100 tokens in the trypsinogen place, to effectively represent 100 percent of the available trypsinogen-like molecules in the system. The enterokinase place was initialized with one token. This establishes that enterokinase is necessary to initiate the process, but that it does not play a significant role in the overall activation to trypsin once the system has been fully initiated.

The observed experimental concentrations of active trypsin production were from Kasche, V., *Arch Biochem Biophys* 173:269–272, 1976), using % concentration of trypsinogen-like molecules in the active trypsin state as a function of time, and which represents the kinetics of activation and inactivation Simulated results obtained by performing simulations on the Petri net model produce results which can be represented as the quantity of tokens in each of the places as a function of transition step, similar to a kinetic profile of concentration versus time. When done originally for the trypsin model results showed that the model based solely on the stoichiometry of the system was not adequate to completely describe the system behavior. Further refinement utilized fundamental parameters of Petri net modeling, e.g., addition of places and transitions and modification of arcs, until successive approximations produced a final representative model of the observed behavior. The first major adjustment enabled accumulation of the active trypsin intermediate (as was seen experimentally) by inhibiting the inactivation transition for a fixed number of transition steps to allow trypsin to accumulate before it is inactivated. The second adjustment added after the accumulation was resolved, was based on the fact that the rates of activation and inactivation were constant at a rate of one token per transition step. The concept of parallel processing was used to model all aspects of the experimental data without affecting the relationships of the molecules or the stoichiometry of the system. If the rates of activation or inactivation needed to be altered, then similar reactions could be placed in parallel. The only difference between the parallel reactions would be the multiple used to define the stoichiometric relationship. For example, in the initial model, one trypsinogen and one active trypsin come together to produce two trypsins. (stoichiometric relationship is 1:1:2). If an additional similar relationship is placed in parallel such that the ratio of components is 3:3:6, a stoichiometric multiple of three, then the rate of activation can be altered between a value of one and three tokens per transition step depending on which of the two transitions are enabled. By incorporating these modifications into the original Petri net model, successive approximations were performed to find the best Petri net model which was still based on the molecular relationships and the stoichiometry of those relationships. Accumulation was achieved by inhibiting the inactivation transition during the first 40 steps. Second, placement of a second activation reaction in parallel with the first activation reaction, created an activation rate step of two tokens per transition step during the first 20 steps. The 1:1:2 transition and the 3:3:6 transition each fire 50 percent of the time during the first 20 steps since each is enabled at each step creating an average activation stoichiometry of 2:2:4. After 20 steps the 3:3:6 reaction is inhibited such that only the 1:1:2 reaction proceeds for the duration of the model. The results of the final model correlated well with the experimental data.

Because larger, more complex biological systems would be difficult to model using this method unless structural reduction methods can be applied, stochastic activity nets (SANs) were applied using the UltraSAN program.

Stochastic Activity Nets

The ability to dynamically construct models and modify them to reproduce phenomenological observations of the system under study also requires the incorporation of probabilistic functions to control transitions in the increasingly complex systems. Liebman and colleagues have applied stochastic activity net models to extend the function of Petri nets to accomplish these goals. Stochastic activity nets may be implemented using the UltraSAN tools (J. Couvillion et al., *IEEE Software*, 8:69–80, 1991), in which the additional capabilities reduce to reproduce Petri nets when probability of each event becomes 1 or 0. UltraSAN allows for hierarchical modeling of networks that can either be simulated or solved analytically.

The UltraSAN environment contains five process elements: places, activities, gates, arcs, and tokens. Places and tokens of a SAN correspond directly to those same elements in a Petri net. "Activities" are an extension of the Petri net transition, and can either be designated as instantaneous or timed. Furthermore, activities have the added feature of allowing case probabilities which can alter an activity's response under varying input conditions. Gates and arcs replace the directed arcs of Petri nets. Gates dictate token flow between places and activities rather than arc weights. A gate must be used in conjunction with arcs connecting it to the associated place and activity, unless the token transfer from a place to an activity or from an activity to a place is one in which only a single arc is required.

The activity process element differs from its analogous Petri net transition in how it responds within the network. Petri net simulation can be either parallel or sequential and is based on the transition step, an arbitrary unit. UltraSAN simulation is done sequentially but is based on simulation time, the computer processing time that it takes to complete a simulation. This occurs because each timed activity in a SAN contains a user-defined "Activity Time Distribution Function" that dictates the amount of time it takes for tokens to pass from the input places to the output places. Therefore, SAN network execution and modeling time is based not only on the token flux being transferred as it is in Petri net simulations, but also on the rate of timed activity execution. This generates more exacting control in the modeling process using UltraSAN.

Another unique property of the activity process element is its ability to respond separately to distinct states of the network. For example, given that the number of tokens in an input place will be a value of zero, one, or two, a timed activity can be defined to give one of two different outputs and can be assigned a probability for each occurrence. These three cases can represent any combination of probabilities. For example, when the value of the input place is zero, Case 1 is activated with a probability of 1.0. When the value is 1, Case 1 and 2 are activated each with a probability of 0.5. Finally, when the value is 2, Case 2 is activated with a probability of 1.0. The presence of case probabilities with activities enhances the modeling capabilities for reproducing the complex experimental behavior observed in the biochemical systems under study.

Detailed information on the UltraSAN package has been presented (Couvilion et al., supra; J. F. Meyer et al., *Proc. Intl Conf on Timed Petr Nets*, Torino, Italy, July 1985; W. H. Sanders et al. *Discrete Event Dynamic Systems: Theory and Applications*, . 3:271–300, July 1993; *UltraSAN User's Manual*, Version 3: Center for Reliable and High-Performance Computing, Coordinated Science Laboratory, University of Illinois at Urbana-Champaign, 1995).

In an example, the network is comprised of five places, p1–p5, and six activities, t1–t6, similar to the Petri net. However, in addition to the places and activities, the SAN representation contains the input and output gates, IG1–IG2 and OG1,OG2,OG3, respectively. These gates serve to direct the flow of tokens throughout the network just as the arc weights do in the Petri net representation. The structural reduction of Petri Nets is inherent in SANs, which upon their individual generation and evaluation can be used to build a composite model by integration with independently generated SANs. Therefore, UltraSAN allows the system modeler to decompose a large, complex system into separable simpler systems such that these subsystems can be modeled and refined in parallel, and then integrated into a larger composite model whose parameters can be further refined. This hierarchical approach to modeling complex biological systems is essential for analyzing the systems of physiological interest and disease processes which are the goal of the research.

Upon completion of development of the model representation, simulations can be performed to evaluate its response in comparison to experimental observations. During these simulations, any individual place within the model can be "viewed" at any instant of time, such that reactivity profiles can be generated of the constituent token levels as a function of the simulation time.

Stochastic Activity Net (SAN) Modeling of Biological Pathways

Figure 14:
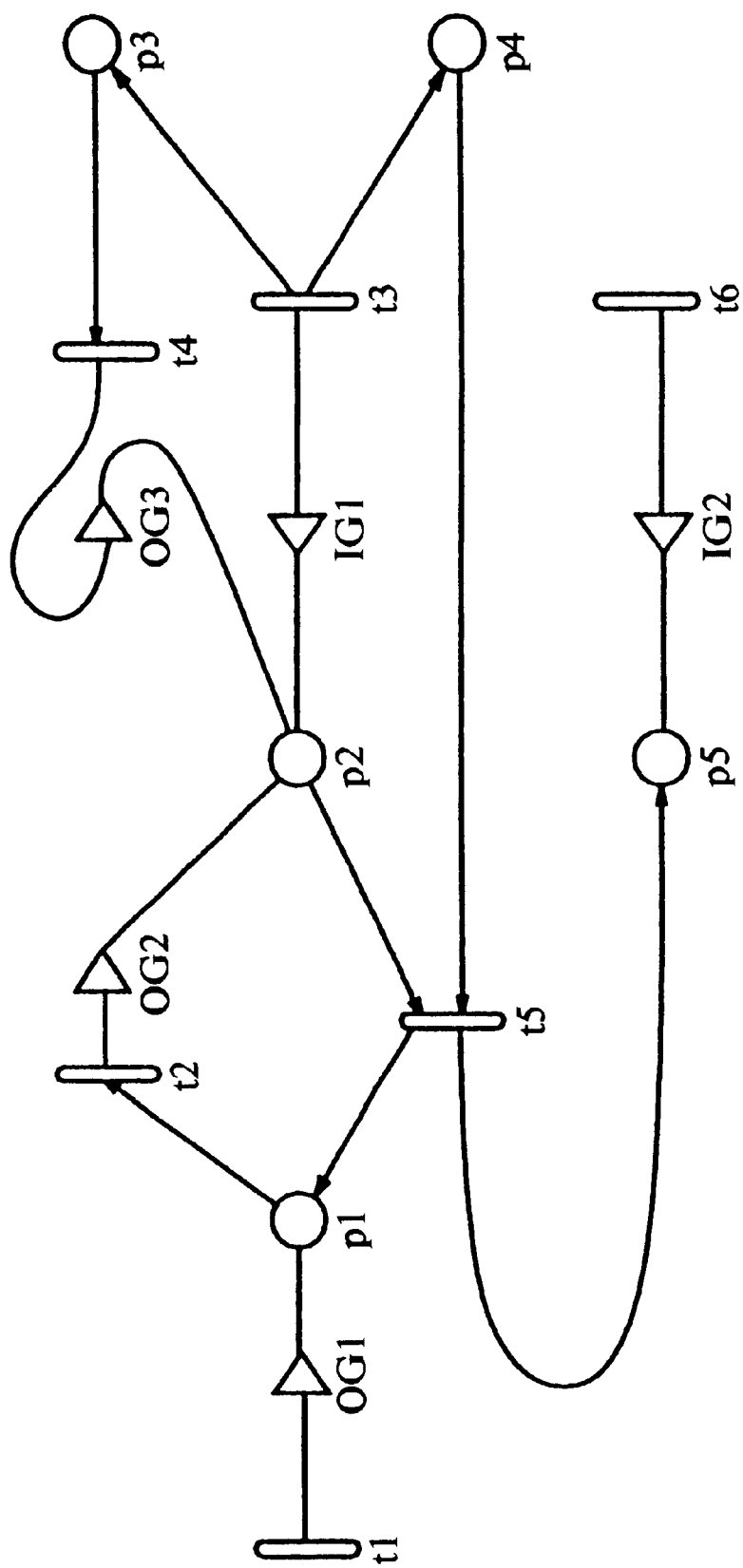
FIG. 14 is a schematic illustration of the equivalent Stochastic Activity net representation of the Petri net shown in FIG. 13.

The process of creating a SAN representation of a biological pathway is similar to that described above beginning with creating a model of the pathway based on the stoichiometry of the reactions of the system. A final model is developed by making successive network adjustments keeping the initial model intact, recognizing the additional adjustable parameters inherent in a SAN. The final SAN representation of the trypsinogen activation system comprised four places representing each of the molecular species, and three activities representing the individual reactions. The final representation created with UltraSAN looked similar to the original system created with the Petri nets (FIG. 14). The behavior of the network is concealed in the two input gates, IG1–IG2, and the two output gates, OG1–OG2.

The system is defined by initial marking of the network as 100 for trypsinogen, one for enterokinase, and zero for all others. If the number of tokens in the trypsin place is less than three or greater than 40, then case two, represented as the bottom node on the activity, will fire because it has a probability of 1.0 in these cases. All other conditions lead to the two cases having equal probabilities of 0.5. Input gate IG1 states that the inactivation activity will not be enabled until the number of tokens in the trypsinogen place is less than 40. Input gate IG2 states that there must be at least two tokens in the trypsin place for activity t3 to be enabled at which time one token will be removed. Output gate OG1 states that each time Case 1 is selected, two tokens are removed from the trypsinogen place and four tokens are put in the trypsin place. This is in addition to the one token removed from each of the trypsinogen and trypsin places because they act as input places for transition t1. Therefore, the overall stoichiometry of this reaction representation is 3:3:6. Output gate OG2 states that each time Case 2 is selected two tokens are placed in trypsin place. Again, this is in addition to the removal of one token from each of the input places trypsinogen and trypsin, such that the stoichiometry of this reaction representation is 1:1:2.

The UltraSAN representation shows that the simulated curves are comparable both to the experimental profile as well as the Petri net results, which is not unexpected because SANs are an extension of Petri nets. The final UltraSAN model required only two additional nodes. The Petri net model required ten additional nodes. The more robust UltraSAN tool created a much simpler result than did the Petri net model, both in representation and in data collection.

The results of the SAN simulations showed the response of the pathway if trypsinogen was reduced in quantity or activity to ⅔ of its normal level. This perturbation effectively decreased the production of active trypsin to only ⅔ of the expected amount under normal conditions. If trypsin were similarly, but separately, reduced to ⅔ activity or availability, the model showed a more significant drop in trypsin production compared to the effect of a trypsinogen deficiency, predicting that trypsin levels would only rise to ⅓ of normal before removal by inactivation.

The modeling experiments of Liebman and colleagues described above: (1) established the applicability for using Petri network methods to represent, analyze and simulate biological pathway information in a manner which is calibrated against experimental observations; 2) extended the application of Petri nets to the use of SANs to enhance the capabilities necessary for biological pathway modeling; and 3) evaluated the sensitivity of the model to predict response in computational experiments designed to simulate significant biological perturbations.

The conversion of the trypsinogen-trypsin pathway into a Petri net minimally approximated the observed kinetic behavior of the pathways components. The method allows for refinement of the network to produce a structured Petri net, whose kinetic behavior closely approximates that of the experimental observations. These results established the utility of the Petri net to represent and simulate pathways of similar complexity such as the SAM pathways of the present invention.

Applicability for Predicting Effects of Enzyme Inhibition and Modeling SAM Pathway Effects of Target Drugs The results described above indicate that both Petri networks and SANs can be successfully applied to the modeling of biological pathways. The SANs provide additional flexibility in the extension of the model to more complex systems. The present inventors' utilization of these methods for the analysis of abnormal or disease states associated with altered SAM metabolism requires that the representation be responsive to known perturbations to the natural system, e.g., enzyme inhibition which may range up to 100%.

A significant characteristic of the present models is that the experimentally determined kinetic data has not been incorporated in generating the model, rather only in refining the model which was constructed using stoichiometric relationships which relate pathway components and which reflect information related to molecular recognition, selectivity and specificity.

The Petri Net and stochastic activity net modeling approaches are generally equivalent in their ability to reproduce experimental observations. Further experience of Liebman and colleagues in building models of physiological systems such as blood coagulation and complement activation support the contention that SANs provide a stable and efficient environment for accurately modeling complex biological pathways such as the eight SAM pathways of the present invention.

The flexibility inherent in the approaches described above is valuable for use in the present invention in the following contexts:

A Pathway/Process Simulation, for example, to identify pathway control points and to enable modeling of complex clinical/phenomenological behavior from limited data;

B. Rational Experimental Design for example, to identify potentially missing elements in a pathway by mapping topologically functionally related pathways and to identify control points utilized in related pathway for use in identifying sites for potential therapeutic intervention;

C. Clinical Target Evaluation, for example, to evaluate control features of selected enzyme targets and to evaluate cross-pathway communication which could impact specificity and selectivity;

D. Risk Assessment, for example, to evaluate potential risk associated with indirect (secondary) pathway activation and possible means to detect this in preclinical or early clinical trials.

The latter is of particular relevance to the present invention because of the intersection of the SAM pathways and the impact of metabolites or enzymes of one pathway on the activity and output of another of the SAM pathways.

An example of the applicability of these approaches to the present invention is presented below. SAM is the sole methyl donor in many important methylation reactions as described above (membrane phospholipids, proteins, DNA, RNA and certain small molecules) which play important roles in the regulation of many cellular processes. In al the reactions involving the donation of a methyl group from SAM to any of a large number of acceptors, the basic reaction is:

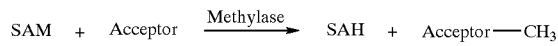

In all these reactions, the product SAH is a known inhibitor of many methylation reactions. SAH is a particularly potent inhibitor of tRNA methyltransferase (Kerr et al., *J. Biol Chem.* 247:4248–4852 (1972)) suggesting that SAM-:SAH ratios may control tRNA methylation levels. High SAM concentrations (Regina et al *Arch. Biochem. Biophys.*, 300:598–607 (1993)) and high SAH concentrations (Wolfe, S. M. and Borchardt, R. T. *J. Me. Chem.* 34: 1521–1530 (1991)) are each toxic to cells. For this reason, the control of SAM:SAH ratio has important applications in therapeutics and diagnostics. Because the SAM:SAH ratio determines the degree of methylation, this ratio is an important determinant of global methylation reactions in a subject. SAM can go into several different pathways as illustrated in FIG. 15 in connection with its role in homocyteinemia.

Figure 15:
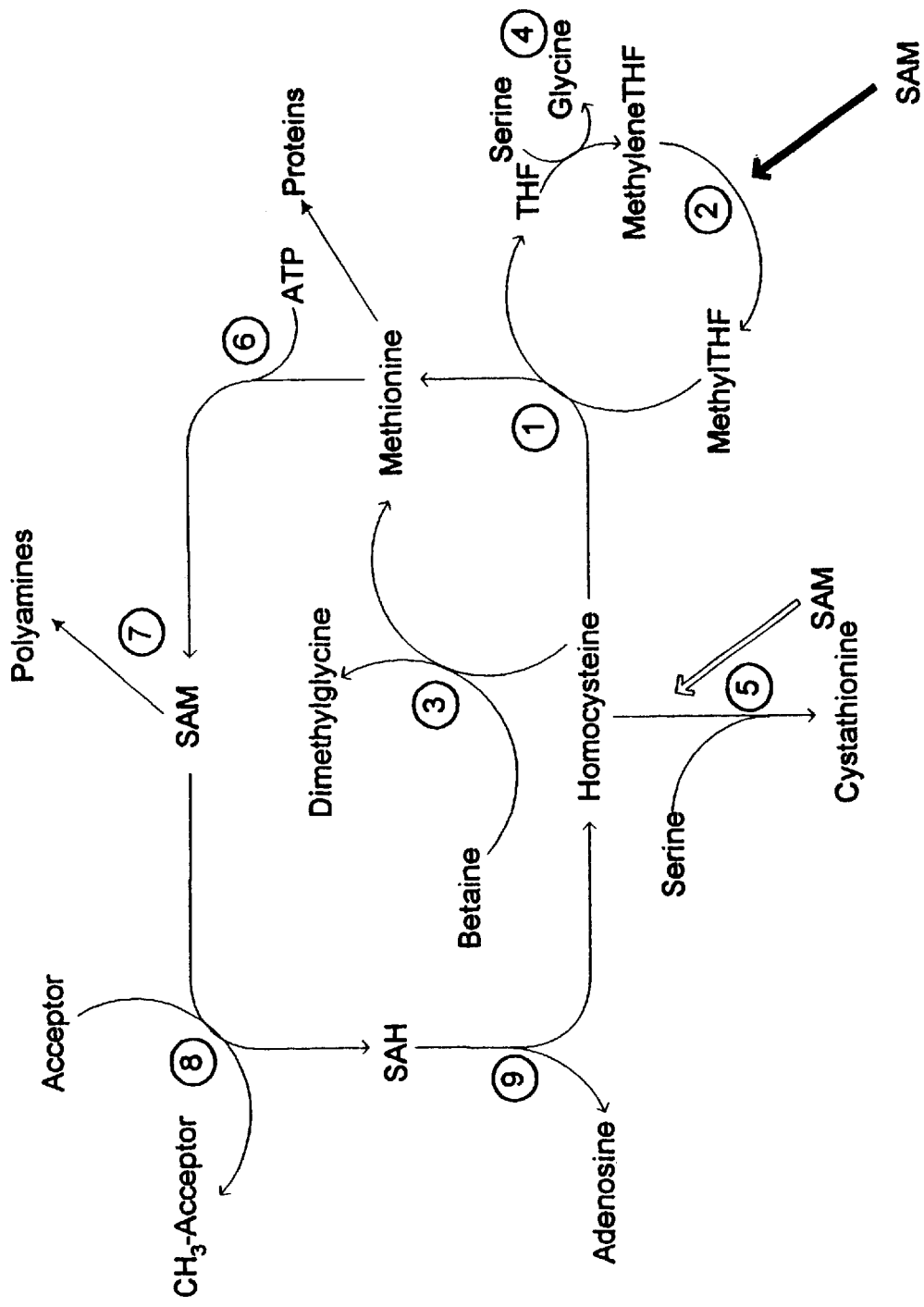
FIG. 15 is a schematic illustration of homocysteine metabolism in man and animals. Enzyme reactions that are regulated by SAM are indicated by large arrows: closed arrow indicates inhibition, open arrow indicates activation. Enzymes shown by number are.

Homocysteinemia is an example of a disease that is intimately involved with abnormal metabolism in the reactions surrounding the synthesis and degradation of SAM (FIG. 15). Patients with premature cardiovascular disease have significantly higher concentrations of homocysteine in plasma than that found in age-matched controls (Selub et al., *Am. J. Clin. Nutr.* 55: 131–138 (1992)). These authors hypothesized that the pathogenesis of homocysteinemia is caused by an interruption of the coordinate regulation of SAM of the remethylation and transsulfuration of homocysteine. The impairment of one homocysteine metabolic pathway necessarily leads to the impairment of the other homocysteine pathway resulting in homocysteinemia. As is seen in FIG. 15, any aberrant enzyme activity of the enzymes or enzyme systems can potentially influence the SAM: SAH ratio which, in turn, influences homocysteine levels. Additionally SAM activates enzyme 5 (as designated in FIG. 15) and inhibits enzyme 2. SAH is formed from SAM in all methylation reactions. A number of methylase reactions occur at high levels in the liver catalyzed by several distinct methyltransferases. To elevate the homocysteinemia, SAM levels must increase relative to SAH. The influence of any of the reactions illustrated in FIG. 15 can influence SAM:SAH ratios directly or indirectly.

It becomes possible using the computer-based modeling systems described above to predict to what extent a drug being evaluated as an inhibitor of one enzyme, e.g., in polyamine synthesis, will preserve SAM and change the SAM:SAH ratios to a level that lowers plasma homocysteine. Since SAH can be formed from other reactions, it is also possible to predict effects of inhibition of these reactions on these pathways. If the effect on the SAM/SAH ratio or on the SAH level is not sufficient to achieve a biological effect, the using the above models, one can determine which other enzyme or metabolite should be targeted to achieved the desired effect through a combination of agents. In other words, this approach will assist in determining which type of agents to evaluate and how much of each to use for a particular biological/biochemical outcome.

If an equilibrium exists in a subject between SAM and SAH such that the ratio of these metabolites is 80:20, and a perturbation occurs which alters the equilibrium ratio to 50:50, it is now possible to predict the new concentrations of other SAM metabolites in the eight SAM pathways in a dynamic manner. Thus, the net effect on either specific or global methylation reactions (increase or decrease) can be modeled and predicted aiding the development of new drugs.

At a different level, if a subject has a genetically abnormal enzyme in a SAM pathway that functions at, for example, 70% of "normal" activity, it is possible using the present approach to predict the amount or dose of a particular agent, directed to a specific metabolic target, to administer to upregulate the deficient enzyme without dysregulating the particular SAM pathway of which the enzyme is a member, or any other SAM pathway, thereby minimizing side effects.

In general, once a model is established using Petri Nets or SANs for the SAM pathways, it becomes possible to predict effects of a drug acting at one point in the pathway on multiple aspects of metabolism without requiring in vivo testing. This is a valuable addition to our ability to identify and test a specific inhibitor of a particular enzyme in a SAM pathway. In addition the modeling of the effect of more than one agent acting on more than one target enzyme in more than one SAM pathway will be valuable in allowing more efficient regulation of aberrant enzyme activities. Such information will permit the development of drugs with more desired pharmaceutical effects.

PHARMACEUTICAL OR THERAPEUTIC COMPOSITIONS

The pharmaceutical or therapeutic composition of the present invention may be comprised of a SAM metabolite or an agent which influences the activity of a SAM pathway or a pathway which is modulated by a SAM pathway, in combination with a pharmaceutically acceptable carrier or excipient.

The pharmaceutical compositions of the present invention wherein may be administered by any means that achieve their intended purpose. Amounts and regimens for administration can be determined readily by those with ordinary skill in the clinical art of treating the particular disease or condition for which the composition is intended.

For example, administration may be by oral or parenteral routes, which may include subcutaneous, intravenous, intramuscular, intraperitoneal, intrathecal, topical, intradermal, transdermal, or buccal routes. Alternatively, or concurrently, administration may be by the oral route and a parenteral route. The dosage administered will be dependent upon the age, health, and weight of the recipient, kind of concurrent treatment, if any, frequency of treatment, and the nature of the effect desired, as can be determined readily by one skilled in the art.

Pharmaceutical or therapeutic compositions within the scope of this invention include all compositions wherein the active agent is contained in an amount effective to achieve its intended purpose. While individual needs vary, determination of optimal ranges of effective amounts of each component is within the skill of the art. Preferred dosages comprise 0.001 to 100 mg/kg/body wt.

Suitable formulations for topical administration include creams, gels, jellies, mucilages, pastes and ointments. The compounds may also be formulated for transdermal administration, for example, in the form of transdermal patches so as to achieve systemic administration.

Suitable injectable solutions include intravenous subcutaneous and intramuscular injectable solutions. The active compound may also be administered in the form of an infusion solution or as a nasal inhalation or spray.

Suitable formulations for oral administration include hard or soft gelatin capsules, pills tablets, including coated tablets, elixirs, suspensions, syrups or inhalations and controlled release forms thereof.

Solid dosage forms in addition to those formulated for oral administration include rectal suppositories.

In addition to the pharmacologically active compounds, the new pharmaceutical preparations may contain suitable pharmaceutically acceptable carriers comprising excipients and auxiliaries which facilitate processing of the active compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 20 to 75 percent of active compound(s), together with the excipient.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders such as starch paste, using, for example, maize starch, wheat starch, rice starch, potato starch, gelatin, taagacanth, methyl cellulose, hydroxypropylmethylcellulose, sodium carboxymethylcellulose, and/or polyvinyl pyrrolidone. Auxiliaries are, above all, flow-regulating agents and lubricants, for example, silica, talc, stearic acid or salts thereof, such as magnesium stearate or calcium stearate, and/or polyethylene glycol. In order to produce coatings resistant to gastric juices, solutions of suitable cellulose preparations such as acetylcellulose phthalate or hydroxypropymethyl-cellulose phthalate are used.

Pharmaceutical preparations which can be used rectally include suppositories which consist of a combination of the active compounds with a suppository base. Suitable suppository bases include natural or synthetic triglycerides, or paraffin hydrocarbons. Useful gelatin rectal capsules consist of a combination of the active compounds with a base material such as liquid triglycerides, polyethylene glycols, or paraffin hydrocarbons.

Suitable formulations for parenteral administration include aqueous solutions of the active compounds in water-soluble form, for example, as water-soluble salts. Suspensions of the active compounds as appropriate oily injection suspensions may be administered. Suitable lipophilic solvents or vehicles include fatty oils, for example, sesame oil or synthetic fatty acid esters, for example, ethyl oleate or triglycerides. Aqueous injection suspensions may contain substances which increase the viscosity of the suspension, such as sodium carboxymethyl cellulose, sorbitol, and/or dextran. Optionally, the suspension may contain stabilizers.

Other pharmaceutically acceptable carriers for the compounds according to the present invention are liposomes, pharmaceutical compositions in which the active ingredient is contained either dispersed or variously present in corpuscles consisting of aqueous concentric layers adherent to lipidic layers. The active ingredient may be present both in the aqueous layer and in the lipidic layer, inside or outside, or, in any event, in the non-homogeneous system generally known as a liposomic suspension. The hydrophobic layer, or lipidic layer, generally, but not exclusively, comprises phospholipids such as lecithin and sphingomyelin, steroids such as cholesterol, more or less ionic surface active substances such as dicetylphosphate, stearylamine or phosphatidic acid, and/or other materials of a hydrophobic nature. Liposome carriers can be used to deliver the active compounds to a subject in vivo as well as to enhance the uptake of the compound by cells in vitro in methods evaluating the therapeutic potential of a compound.

Having now generally described the invention, the same will be more readily understood through reference to the following examples which are provided by way of illustration, and are not intended to be limiting of the present invention, unless specified.

EXAMPLE I

Use of the Sam Paradigm to Treat Wounds

Based on the knowledge of SAM pathways and related pathways and their relationship to wound healing and cell growth, as described above, SAM pathway and related intermediates were prioritized into two groups as follows.
First Priority Group: SAM Metabolites SAM, biotin, ethylene, 1-aminocyclopropanecarboxylic acid (ACC), polyamines (putrescine, spermine, spermidine), ornithine, arginine, methionine, adenosine, queuine, queuosine, Wye base.
Second Priority Group: Non SAM Pathway Molecules Influenced by the SAM Pathways calmodulin, fibronectin, protein kinase C epidermal growth factor (EGF), insulin-like growth factor (ILGF), platelet-derived growth factor (PDGF), transforming growth factor β (TGF-β), basic fibroblast growth factor (bFGF), nicotinamide, inositol.

To begin the analysis, a subset of the first priority group was selected as described previously, resulting in the following group:

SAM, ethylene, biotin, polyamines (putrescine, spermine, spermidine), ornithine, methionine, adenosine, nicotinamide A shorter list of target metabolites for study comprised SAM, ethylene, biotin, polyamines, nicotinamide. The basis for selecting this group was as follows. It was, determined that nicotinamide increases the capillary density in injured skin significantly compared to injured skin of saline-treated controls (Smith et at., J. Surg. Res. 47:465–469 (1989); see below). These properties of nicotinamide prompted its inclusion into the mixture tested. The affinity chromatography approach described herein is used to identify the proteins involved in the regulation by the SAM pathway intermediates. By identifying these target proteins, it permits the design of specific methods to selectively up-regulate or down-regulate individual SAM pathways and levels of SAM pathway intermediates. For a number of reasons described below, substitutions were required.
Substitution of Adenosine and Methionine for SAM SAM is relatively unstable in aqueous solutions. For example, The chloride salt of SAM (Sigma Chemical Company, St. Louis, Mo.) loses 10% of activity per day at 25° C. Other salts listed were similarly unstable. More stable salts are known in the literature but were not available for this study. It was therefore decided to use a combination of methionine and adenosine instead of SAM, reasoning that SAM would be synthesized in vivo from these two precursors (Ochi et al., J. Bacteriol. 152:400–410 (1982). Subsequent to this study, it was learned that SAM sulfate (commercially available from Boehringer Mannheim, Indianapolis, Ind.) is stable for 6 months at 4° C. The stability can be improved further by applying it in a hydrophobic ointment consisting of 5% beeswax and 95% white petrolatum (US Pharmacopoeia 17:975 (1990)). This salt would allow direct evaluation of SAM, rather than the indirect evaluation performed here.
Substitution of ACC for Ethylene Ethylene is a gas and is difficult to dissolve in a controllable manner in the ointment base used (See US Pharmacopoeia 17:975 (1990) for preferred ointment base). It was therefore decided to use 1-aminocyclopropanecarboxylic acid (ACC) which is the precursor of ethylene in plants. Since ethylene has been shown to be present in mammals, it was reasoned that ACC will be converted to ethylene in vivo by human ACC oxidase. Chloroethanephosphonic acid (CEP) is also used extensively in agricultural to deliver ethylene. CEP is stable in a nonaqueous environment but decomposes to ethylene in an aqueous environment. CEP may therefore be used in the hydrophobic ointment described above to deliver ethylene to the wounded area.
Polyamines Since it was known that polyamines accelerate wound healing, it was decided not to include these compounds into the first test mixtures, but to combine it with other active compounds at a later stage.
Nicotinamide Wounds initially become devascularized, and nicotinamide increases capillary density in injured skin. (Smith et al., J. Surg. Res. 47: 465–469 (1989)). It was therefore decided to included this intermediate, which was a member of the second priority group, with the SAM intermediates to increase their impact.

Thus, the final list of compounds comprising the test therapeutic composition was as follows: adenosine, methionine, ACC, biotin and nicotinamide. The compounds of this mixture were not tested individually, but rather, an ointment containing all five compounds was tested. If this or any other mixture tested positive, a reverse engineering or "deconvolution" procedure would be used to determine the activity of individual intermediates.

Materials, Methods and Results

| Compound | Concentration % w/w |
|---|---|
| Methyl p-hydroxybenzoate | 0.025 |
| Propyl p-hydroxybenzoate | 0.015 |
| Sodium Lauryl Sulfate | 1 |
| Propyleneglycol | 12 |
| Stearyl Alcohol | 25 |
| White Petrolatum | 25 |
| Water | 37 |

The stearyl alcohol and white petrolatum were melted at about 75° C., and the other ingredients, previously dissolved in water at about 75° C., were added and stirred until the mixture congealed (US Pharmacopoeia 17:975 (1990)).

The test ointment contained 0, 0.018, 0.18 or 1.8 mg/ml each of adenosine, methionine, nicotinamide, biotin and ACC.

Experiment 1: Test Protocol

Mice (weighing 17–20 g) were divided into 5 groups of 6 consisting of one untreated negative control group, four different treatment groups for the test compositions. The mice were anesthetized (I.P.) with sodium pentobarbital at 3 mg/100 g body weight. While under anesthesia, the upper back far was shaved using an electric hair clipper. The skin on both sides of the back was washed with sterile saline. The upper back area was used for the wound to minimize licking. Using an ethanol-sterilized punch, one wound approximately 3 mm diameter was made on the upper part of the back by lifting the skin away from the body of the mouse and punching through the skin between the body and the fingers of the investigator. This resulted in two puncture wounds about 1–2 cm apart.

The test therapeutic composition, in the above ointment vehicle, was applied immediately following wound incision. Treatment composition (or control vehicle) was applied daily for 7 days with a sterile swab. The healing was evaluated qualitatively by a blinded observer.

The treatment compositions shown below included adenosine, methionine, biotin, ACC and nicotinamide each at the indicated concentration. The experimental groups were as follows:

| Group | Left Wound | Right Wound |
|---|---|---|
| A | Untreated | Untreated |
| B | Untreated | Control Ointment ("Control") |
| C | Control | 0.018 mg/ml |
| D | Control | 0.18 mg/ml |
| E | control | 1.8 mg/ml |

The wounds were observed for healing or closure daily for 14 days. Each animal in Groups C–E served as an internal control (left wound receiving control ointmerit, right wound receiving test ointment). The results are shown in Table VIII, below.

TABLE VIII

Effect of Test Compounds on Wound Healing

| | Number of Animals per group showing improvement in Right wound compared to Left wound | | | |
|---|---|---|---|---|
| Day | Group C (0.018 mg/ml) | Group D 0.18 mg/ml | Group E 1.8 mg/ml | Group B Control |
| 1 | NC* | NC | NC | NC |
| 2 | NC | NC | NC | NC |
| 3 | NC | NC | NC | NC |
| 4 | NC | 1** | NC | NC |
| 5 | NC | 1 | NC | NC |
| 6 | NC | 2 | NC | NC |
| 7 | 2 | 2 | NC | NC |
| 8 | 3 | 3 | NC | NC |
| 9 | 4 | 4 | NC | NC |
| 10 | NC | 4 | 2 | NC |
| 11 | NC | 2 | 2 | NC |
| 12 | NC | 5 | 2 | NC |
| 13 | NC | 5 | 2 | NC |
| 14 | NC | 5 | 2 | NC |

*NC = no change relative to control
**number of animals showing improvement in wound out of total As seen on day 14, 5/6 mice showed better healing than in the control wound at a concentration of 0.18 mg/ml of each of the test compounds. Therefore this composition was active in accelerating wound healing.

Experiment 2.

This experiment differed from experiment 1 as follows:
1. The wound size was increased to 5 mm.
2. Both wounds on each mouse were treated with the same compounds
3. Four groups of six mice were treated as follows:

| Group A: | control ointment (vehicle) |
|---|---|
| Group B: | 0.018 mg/ml; |
| Group C: | 0.18 mg/ml and |
| Group D: | 1.8 mg/ml |

4. The wound diameters (in mm) were measured on day 11.

The results are shown in Table IX.

TABLE IX

| Test Compound (mg/ml) | Wound Diameter mm (± SD) |
|---|---|
| Control | 2.45 ± 0.37 |
| 0.018 | 2.60 ± 0.56 |
| 0.18 | 1.73 ± 0.24* |
| 1.8 | 2.56 ± 0.56 |

*statistically significant relative to control.

This experiment confirmed that the composition including adenosine, methionine, biotin, ACC and nicotinamide each at 0.18 mg/ml significantly promoted wound healing.

Experiment 3

This study was similar to Experiment 2, with the following changes.
1. Wound size was increased to about 6 mm diameter.
2. The wound diameters were measured with a micrometer on days 0, 3, 5, 8 and 11 to allow calculation of wound area.
3. Test or control compositions were applied daily. Compounds in each test composition were varied
4. N=10 mice per group
5. The each compound in the test compositions was present at a concentration of 0.18 mg/ml.

| Group | Composition |
|---|---|
| Control | Ointment vehicle |
| A | ACC (A), Biotin (B), Adenosine (Ad) Methionine (M) and Nicotinamide (N) |
| B | A, Ad, M, N |
| C | B, Ad, M, N |
| D | Ad, M, N |
| Neosporin( | polymyxin sulfate, 5000 u; bacitracin zinc, 400 u; neomycin, 3.5 mg/g |

Figure 11:
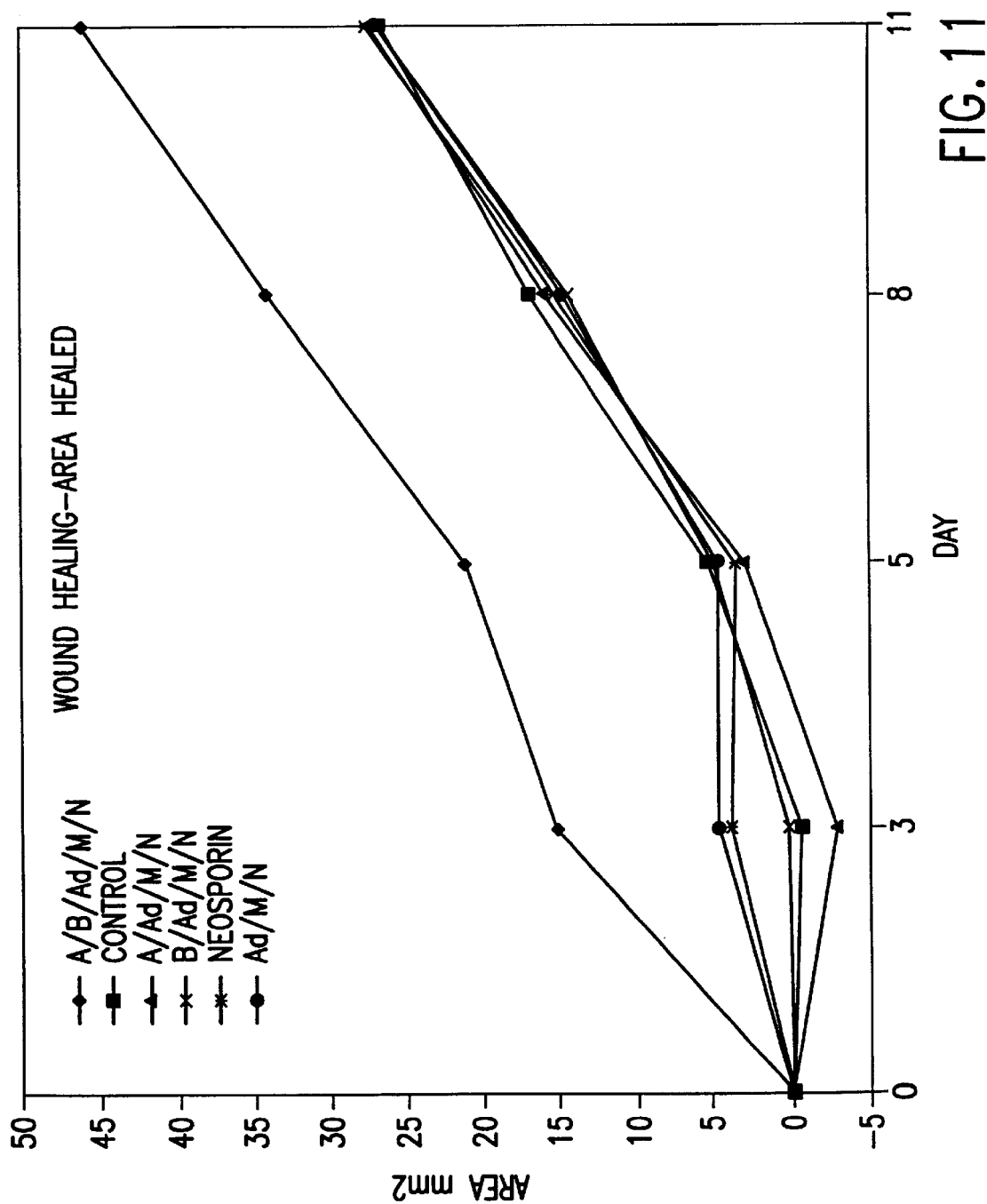
FIG. 11 is a graph showing results of treatment of wounds compositions comprising one or more of ACC (A), biotin (B), adenosine (Ad), methionine (M) and nicotinamide (N). The area of the healing wound area in $mm^2$ is presented.

The results are shown in FIG. 11, which shows the area of the healing wound area in $mm^2$.

As shown, Group A containing all five compounds healed wounds consistently better than neosporin or any of the other combinations. It was concluded that biotin and ACC act synergistically in promoting wound healing.

For further analysis, the following treatment compositions are proposed:
1. SAM sulfate
2. SAM sulfate, biotin, ACC
3. Combinations of group 2, above, that include polyamines and/or nicotinamide and/or ascorbic acid and/or inositol.
4. Combinations which include queuine and/or queuosine.

EXAMPLE II

Use of the Sam Paradigm in Cancer

Based on the knowledge of SAM pathways and related pathways and their relationship to cancer and tumor cell growth, as described above, the following section summarizes states of SAM pathways and intermediates associated with cancer and possible therapeutic approaches based thereon.

DNA is generally under-methylated. In this case, the affinity chromatography or labeling approach is used to determine which cell components are specifically involved in under-methylation. Therapeutic compositions are then developed to correct this imbalance.

Polyamine synthesis is upregulated, leading to the utility of down-regulating polyamines in a treatment approach. QtRNA is changed into GtRNA in cancer and should therefore be up-regulated. Wye-bases are abnormal in tRNA and should be up-regulated. Ethylene appears to be up-regulated, thus indicating a therapeutic down-regulation. Because biotin is required for cell growth, and/or differentiation, therapeutic manipulation of biotin may be necessary. Diphthamide and hypusine, which regulate EF-2 and eIF-5a, respectively, are potential targets four cancer treatment.

A priority group of SAM pathway intermediates which is useful in a cancer therapeutic composition comprises SAM, polyamines (putrescine, spermidine and spermine), queuosine, wye-base, methylthioadenosine, biotin, ethylene, methionine, adenosine.

In a general approach to treating cancer, DNA methylation and queuosine and wye-base incorporation in tRNA should be up-regulated. The intermediates or pathways which should be down-regulated are polyamine synthesis, ethylene synthesis and biotin availability.

In those cases where SAM pathway intermediates behave differently in different type of cancer, additional analysis is performed using the approaches described herein to delineate those differences and to fine-tune the regulation of SAM pathways in the particular type of cancer.

To identify targets of the SAM pathways, the methods based on affinity chromatography, concentration or the labeling-methods will be used as described above.

The affinity chromatography approach is used to identify the proteins involved in the regulation by the SAM pathway intermediates. By identifying these target proteins, the affinity approach facilitates the design of specific methods to selectively up-regulate or down-regulate SAM pathways and levels of SAM pathway intermediates.

A biological fluid in the form of a total cell extract is prepared from cancer cells. In this case HeLa cells are used. The same approach is used for other biological fluids such as blood. A frozen cell pellet is thawed on ice until it becomes liquid. The cell pellet volume is estimated and the cells suspended in 3 volumes of lysis buffer (15 mM KCl, 60 mM NaCl, 50 mM Hepes, pH 7.5, 1 mM EDTA, 10% glycerol); to this was added DTT to 1 mM and a protease mix (0.1 µg/ml Pefabloc, 0.7 µg/ml Aprotinin, 0.7µg/ml Leupeptin, 0.7 µg/ml Pepstatin, 40 µg/ml TLCK) just before use at 4° C. Cells are homogenized using a Potter homogenizer with 10 strokes. Cell lysis may be checked by microscopic examination of a small sample. The lysate is centrifuged for 10 min at 1000×g at 4° C. The supernatant fluid is then examined, or may be stored at −80° C. A Bradford protein assay is conducted on supernatant. The supernatant is adjusted to 0.2% (v/v) with NP-40 and 0.8–1.0 ml of the supernatant containing 5 mg/ml protein is added to the resin containing an affinity ligand of interest (0.1 ml). This mixture is incubated for 30 minutes at 4° C. while mixing gently and then is centrifuged for 60 seconds at 1000×g at 4° C. to remove the unbound material. The unbound material or flow-through is saved as "Wash A". The affinity matrix is washed 3 times with 0.5 ml loading buffer (15 mM KCl, 60 mM NaCl, 50 mM Hepes, pH 7.5, 1 mM EDTA, 1 mM DTT) by gentle mixing for 5 minutes followed by centrifugation for 60 second at 1000×g. Buffer A (250 mM NaCl, 50 mM Hepes, pH 7.5, 1 mM EDTA, 1 mM DTT) in a volume of 0.5 ml, is added to the affinity matrix, incubated for 30 minutes at 4° C. with gently mixing and the mixture centrifuged for 60 seconds at 1000×g. The supernatant from this wash is collected as "Fraction A". This step is repeated successively with Buffer B (750 mM NaCl, 50 mM Hepes, pH 7.5, 1 mM EDTA, 1 mM DTT) and Buffer C (7M urea, 50 mM Hepes, pH 7.5, 1 mM EDTA, 1 mM DTT) to yield "supernatant B" and "supernatant C". The protein concentrations of Wash A and Fractions A–C are determined as described above.

Since the affinity of binding of macromolecules or small molecules to the affinity chromatography ligand was not known in advance, a generic protocol was designed to perform this analysis. In this approach, three eluting buffers are used: a low ionic strength buffer A (0.3M) to elute molecules with relatively low binding affinity; a relatively high ionic strength buffer B (0.8M) to elute molecules with relatively high binding affinity and a denaturing buffer C (7M Urea) to elute any material with high binding affinity to the ligand on the affinity matrix. This procedure was validated by using S-adenosylhomocysteine (Sigma Chemical Company, St Louis, Mo.) coupled to NHS-activated-AffiGel 10 (BioRad, Hercules Calif.), according to the manufacture's instructions. For validation, normal serum and HeLaS3 human cells were used.

The procedure above is conducted in parallel using a normal fluid which is a cell extract from appropriate normal control cells (in this case normal serum). Fractions from the normal cell line (Wash A, Fractions A to C) are compared with HeLaS3 human cells (Wash A, Fractions A to C) cells by running a 10% SDS-PAGE gel, using 10 µg protein per well. Protein bands are detected by silver staining or, alternatively, by Western blot analysis.

Figure 12:
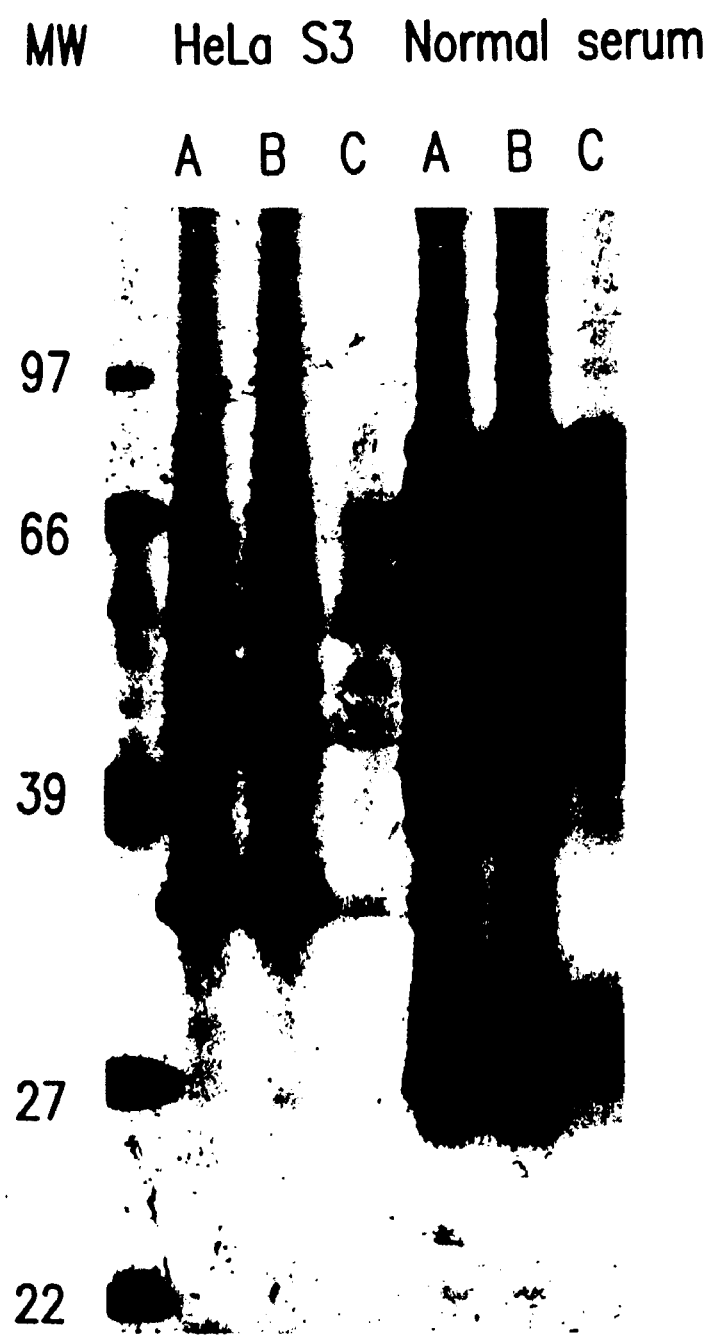
FIG. 12 is a gel pattern showing the proteins from normal human serum or human cancer cells (HeLa S3) which bound to a SAH-agarose affinity matrix.

Differences in concentrations of bands between normal (serum) and cancer cells (HeLa S3 human cells) are identified. As shown in FIG. 12, a number of differences could be identified between normal serum and HelaS3 human cells. It is anticipated that this validated procedure will functioned in a similar fashion when normal and diseased fluids are compared. Once a difference is detected, the protein is characterized by biochemical procedures known in the art.

From the information obtained with the affinity chromatography approach, pharmaceutical and diagnostic products are developed as described below.

Diagnostic Composition:

The identification of differences in protein bands between normal and cancer cells or tissue, is used to develop potential diagnostic markers for this disease. Antibodies specific for these proteins are produced if unavailable and used to develop diagnostic assays using methods well-known in the art.

Therapeutic Compositions

1. The presence of abnormally low or high concentrations of a specific binding proteins in the disease state.
   a. If the protein is an enzyme, inhibition or stimulation of its activity as identified by the present methods, may involve up- or down- regulation by compounds which are not SAM pathway intermediates. Alternatively, the enzyme is one which is not directly involved in a SAM pathway, but its activity is subject to modulation by a SAM pathway intermediate.

An assay for the enzyme is implemented which is used to identify more specific or more potent inhibitors of the enzyme. Combinatorial chemistry approaches are used.

b. If the proteins are binding proteins such as, for example, receptors or allosteric proteins, a binding assay is used to develop compounds to regulate the activity or function of these proteins, preferably with combinatorial chemistry.

EXAMPLE III

Use of the Sam Paradigm in Multiple Sclerosis

The characteristic feature of multiple sclerosis (MS) is demyelination. The effective cause of this condition is not known, but it is believed to be an autoimmune disease and is characterized by episodes of demyelination followed by remission in which remyelination occurs, at least to some extent. Myelin forms a sheath around axons of neurons and is essential for neural signal transmission. In humans, myelin is about 20% protein and 80% lipid. The protein portion is about 50% proteolipid, 20% wolfram protein and 30% myelin basic protein (MBP). In myelination, MBP is first localized to specific areas and myelin then forms at these loci sandwiched between two layers of lipid. This entire complement ensheathes the axon. MBP has a molecular weight of 18 kDa and a pi of 10.5. In humans, only one form of MBP is present, in mice, two forms arise from pre-mRNA alternative splicing.

The methylation status of MBP is critical for myelination. Although MBP has 18 arginine residues, it is methylated only at position 107. Two methylation products are produced, $N^G$-monomethyl arginine (NMeArg) and symmetrical $N^G,N^G$- dimethyl arginine. The few other proteins which are methylated at arginine residues, such as histones, high-mobility group proteins 1 and 2, A1 protein from HnRNP and the 34 kDa nucleolar protein, do not exhibit symmetric dimethylation, and contain only NMeArg and asymmetrical $N^G,N'^G$-dimethyl arginine.

The methyl transferase which acts on MBP, which has subunits of 75 and 100 kDa, is inhibited by SAH at a $K_i$ of $10^{-6}$ M and is quite sensitive to alterations in SAH concentration. It is also inhibited by calmodulin which is itself modulated by SAM-mediated methylation.

Since methylation of MBP is associated with myelination, protocols that enhance the methylation of MBP are helpful in treating MS. As the relevant methyl transferase is inhibited by SAH, it is advantageous to lower the SAH concentration. This can be accomplished, for example, by activating SAH hydrolase or by decreasing the concentration of homocysteine, adenosine, or inosine. Numerous inhibitors of SAH hydrolase are known. First and second generation inhibitors used in antiviral therapy have been reviewed (Wolfe et al., J. Med. Chem. 34:1521–1530 (1991)).

Thus, the parameters to be targeted in MS in accordance with this invention have been identified; those metabolites or metabolic pathways aberrant in MS that are affected by SAM have been identified as a subgroup. Using the present approach, enhanced methylation of MBP has been targeted as therapeutic goal. This is accomplished by regulating the methyl transferase activity indirectly through decreasing the level of SAH.

The disease parameters associated with MS have been reported. These parameters are considered when identifying aberrant SAM metabolites or other pathways that are affected by SAM. Relevant parameters associated with MS are as follows:

1. Vitamin $B_{12}$ and folate are decreased in cerebrospinal fluid and serum; however, addition of vitamin $B_{12}$ to the diet does not seem to reverse MS, and although the age of onset of MS is related to serum vitamin $B_{12}$ levels, there is no relationship with respect to folate levels. It is known that vitamin $B_{12}$ deficiency is associated with undermethylated proteins. Treatment with methyl donors such as methionine, betaine and SAM is associated with remyelination in patients with inborn errors of folate and one-carbon metabolism, suggesting that impaired methylation may occur in several neurological diseases such as MS by different mechanisms (Bottiglieri et al., Drugs 48:137–152 (1994)). In contrast, treatment of animals with $N_2O$ to inactivate Vitamin B12 (and thus prevent the synthesis of methionine by methylation of homocysteine) led to subacute combined degeneration (SCD), which is characterized by degeneration of the myelin sheath (Kim et al., In: Protein Methylation (Paik et al., eds), CRC Press, Boca Raton, Fla., 1990, pp. 77–96). The effects of $N_2O$ treatment, however, were completely abrogated by concurrent treatment with methionine as the animals were free of pathological changes. The symptoms of SCD also could be produced by treatment with cycloleucine, an inhibitor of SAM synthetase and thus of methylation. Furthermore, such cycloleucine treatment was shown to strongly depress the specific methylation of myelin basic protein in vivo, again arguing for the critical need of regulated SAM-mediated methylation in the myelination process.

2. Mercury secretion is decreased. Siblerud et al., Sci. Total Environ. 142:191–205 (1994)), suggested that mercury may be related to MS. MS patients with amalgams were found to have significantly lower levels of red blood cells, thyroxin, total lymphocytes and CD8 suppressor cells compared to MS patients with amalgams removed. Mercury is removed in bacteria by methylation via SAM; similar mechanisms may operate in mammals.

3. Lipid metabolism is abnormal in the brain of MS patients; lipid transport in the brain involves apolipoproteins and LDL receptor. The cholesterol esterifyig enzyme and lecithin cholesterol acyl transferase are decreased in the cerebrospinal fluid of MS patients. Sargent et al. (Med. Hypotheses, 42:237–242 (1994)), showed that the nervonic acid [(24:1 (9)] is depressed and the long chain fatty acids (26:0) is increased in erythrocytes from MS patients. Additionally it is known that SAM is required in numerous transmethylation reactions involving nucleic acids, proteins, phospholipids and neurotransmitters (Pottiglieri et al., 1994). The fatty acid elongation system and the concentration of acidic glycerol phosphatides are decreased.

4. N-methylamino acids are elevated in blood and serun. The levels of circulating catecholamines (epinephrine) in supine and standing subjects were the same in chronic progressing multiple sclerosis patients and normal subjects. However, supine norepinephrine levels were higher in patients than in control subjects (Karaszewski et al., J. Neuroimmunol. 43: 1–7 (1993)). Levels of epinephrine and norepinephrine are regulated by SAM methylation of norepinephrine.

5. T cells are sensitized to MBP and myelin proteolipid protein. Voskuhl et al. (J. Neuroimmunol. 46:137–144 (1993)), determined that although the major isoform of myelin basic protein (MBP) in the healthy adult CNS is the 18.5 kDa protein, other isoforms containing polypeptides encoded by exon 2 (21.5 and 20.2 kDa) exist and are expressed primarily during myelin formation by alternative splicing. Although the frequencies of T cell lines specific for 18.5 kDa MBP were no different between the affected and unaffected, the frequency of the T cells specific for MBP exon 2 correlated with MS. According to the present inventors, methylation may be involved in alternative splicing (see above).

It is known that SAM is required in numerous transmethylation reactions involving nucleic acids, proteins, phospholipids and neurotransmitters (Pottiglieri et al. 1994). However, in examining the foregoing parameters, the present inventors have concluded that methylation states of all four classes of molecules (nucleic acids, proteins, phospholipids and neurotransmitters) are significant factors in the progress of the disease. This suggests that multiple aberrant methylations in MS should be addressed simultaneously. This is particularly the case with respect to methylation of MBP, nucleic acids (alternative splicing), neurotransmitters (norepinephrine) and phospholipids (e.g., formation of phosphatidylcholine).

Other intermediates that may be influenced by SAM pathways are all the components of phospholipids (fatty acids, choline, phosphatidylcholine, etc.), apolipoproteins, LDL receptor, cholesterol esterifying enzyme, lecithin cholesterol acyl transferase, and neurotransmitters. These intermediates may be used as affinity chromatography ligands as described above to determine the regulatory relationships of SAM pathways in disease and non-diseased states. Thus, according to the present invention, all the SAM pathways, i.e., not only the methylation pathway, will be analyzed for their involvement in MS.

EXAMPLE IV

Use of the SAM Paradigm in Alzheimer's Disease

Alzheimer's Disease (AD) is characterized by the formation of plaques in the brains of patients which accompany the symptomatic loss of memory and dementia. In addition there are some commonly encountered metabolic indicators which appear to be associated with AD, a number of which are altered due to a state of undermethylation in AD patients. These indicators are ultimately susceptible to regulation by control of the relevant SAM pathways in accordance with the present invention.

The β-amyloid core protein which characterizes the amyloid plaques found in AD brains is encoded by a alternatively spliced pre-mRNA. In particular, the β-amyloid form contained within AD plaque deposits may arise from altered alternative splicing relative to healthy control subjects of the same age (Johnson et al., *Science* 248:854–858 (1990)). The state of undermethylation in AD patients' cells, proposed by the present inventors, is expected to alter alternative splicing of pre-mRNA and to influence other cellular process which involve methylation (e.g., the production of choline which requires transfer of 3 methyl groups from SAM to the ethanolamine moiety).

In addition, the β-amyloid precursor protein is hydrolyzed by a calcium-stimulated serine protease. One calcium-binding protein which is markedly reduced in AD patients is the 28 kDa protein calbindin-D. Another calcium-dependent cysteine protease, calpain-1, is also involved in the processing of β-amyloid protein.

A significant characteristic of AD is the hyperphosphorylation of the microtubule-associated protein, tau, that is a component of the perihelical filaments in the AD brain. According to the present invention, it is significant that tau is associated with calmodulin and that the pre-mRNA encoding tau is alternatively spliced. Certain kinases and phosphatases are involved in maintaining this hyperphosphorylation. Kinase enzymes which result in abnormal phosphorylation of tau protein include: cAMP-activated lonases cdk2 and cdk5, a calmodulin-dependent protein kinase, a proline-directed serine/threonine kinase, and possibly other kinases associated with microtubules. Two major phosphatases offset the activity of these kinases: calcineurin and protein phosphatase-2a. It appears that these lanases are activated relative to the controlling phosphatases in AD patients. Hyperphosphorylation of elongation factor EF-2 also occurs. The activity of $Ca^{2+}$-calmodulin protein kinase was increased in the presence of calmodulin by carboxyl-methylation of this enzyme (Billingsley et al., *J. Neurochem.* 44:1442–1450 (1985)). McLachlan et al. (*Alzheimer. Dis. Assoc. Disord.* 1:171–9 (1987)), showed that in a group of AD brains, frontal, temporal, parental cortex and subjacent white matter calmodulin content was significantly (66%) reduced compared to control brains obtained from patients that died of unrelated causes.

A second characteristic of AD is in the nature of membrane lipids. These membrane differences are measured as the temperature at which the lipids can form bilayers. This temperature is much lower in AD patients than the critical temperature of 37° C. in normal subjects. Part of this difference may be due to decreases in the phospholipid precursors choline and ethanolamine and increases in the phospholipid deacylation product glycerophosphocholine. In addition, the levels of polyunsaturated fatty acyl groups in phosphatidyl ethanolamine are decreased relative to saturated forms. Also, dolichol phosphate content increases as does the level of ubiquinone.

Cerebrospinal fluid SAM levels were low in a group of patients with AD dementia, suggesting a possible disturbance of methylation in such patients (Bottiglieri et al., *J Neurol. Neurosurg. Psychiat.* 53:1096–1098 (1990)). SAM, known to increase fluidity of membranes in animals, was used to treat AD patients and resulted in increased of membrane fluidity, but no improvement nor worsening of symptoms (Cohen et al, *J. Clin. Psychopharmacol.* 8:43–47 (1988)). These results suggest the involvement of methylation, but indicate that one or more of the experimental approaches described in the invention should be used, to determine which SAM related targets are involved and whether they should be regulated up or down. In particular, it should be realized that SAM treatment of AD patients may only prevent further progression of symptoms rather than curing irreversibly damaged brain cells. Early and continuous treatment with SAM or other agents that affect methylation are predicted to have major effects on the rate of disease progression.

The effects of the foregoing on the function of the cell membrane are clearly related to the pathophysiology of AD. As mevalonate metabolism is likely controlled by levels of biotin, modification of its concentration will affect the progress of AD. The activation status of a multiplicity of enzymes involved in fatty acid synthesis, mevalonate pathways and the like is controlled by SAM Pathway No. 1. In addition, biotin (SAM Pathway No. 8) will be required for the synthesis of fatty acids and likely for mevalonic acid. From the discussion above it is suspected that lipid metabolism is abnormal and this may be regulated by both SAM and biotin.

Vitamin $B_{12}$ deficiency is also characteristic of AD. Proper Vitamin $B_{12}$ levels are necessary for efficient transfer of a methyl group from the tetrahydrofolate system to homocysteine to make methionine. Methionine, in turn, is used for the synthesis of SAM. Hence, reduced levels of vitamin $B_{12}$ will produce altered levels of SAM which will affect cellular regulation. As described earlier, cobalamin levels also are regulated, in part, by the availability of biotin. The importance of vitamin $B_{12}$ is also related to its apparent ability to control the levels of monoamine oxidase enzymes, which appear elevated in AD patients but can be diminished by administration of vitamin $B_{12}$. Cobalamine and folate deficiency is a significant feature in senile dementia in AD and will result in the concomitant slowed synthesis of DNA and SAM (Regland et al., *Med. Hypothes.* 38:11–9 (1992)). Treatment trials with vitamin $B_{12}$, folic acid, SAM and acetyl L-carnitine which are in progress and have been reported (Gottfries, *Eur. Neuropsycopharmacol.* 1:1–5 (1990)).

AD brains have increased levels of total calcium and decreased levels of calcium-binding proteins.

Related to the alteration in membrane lipids characteristic of AD is the altered status of choline metabolism. Choline is used both for synthesis of phospholipids and for synthesis of the neurotransmitter acetylcholine. Acetylcholine may indeed be synthesized at the expense of the membrane phosphatidyl choline. The membrane phosphatidyl choline is formed by methylation of phosphatidyl ethanolamine, and then serves as a source for the choline used to form the neurotransmitter. AD patients are characterized by a reduced amount of acetylcholine and a reduced activity of choline acetyl transferase. Indeed, in AD patients, the isoenzyme pattern of this transferase and its affinity for choline is different from that in normal subjects. Choline levels per se in red blood cells and plasma, both in bound and unbound forms, show differences between AD and healthy controls. The activities of the enzymes responsible for fine-tuning the balance between acetylcholine formation and inclusion of phosphatidyl choline in membrane lipid bilayers are clearly aberrant.

Acetylcholine synthesis is also controlled by L-carnitine and acetyl-L-carnitine (the balance regulated by a carnitine acetyl transferase). Acetyl-L-carnitine has been used as a drug to retard progression of AD. AD patients have significantly lower levels of acetylcholinesterase and choline acetyl transferase activities. As noted above, carnitine is derived from free trimethyllysine which is derived from a small number of critical regulatory proteins that are trimethylated at internal lysine residues (such as $Lys^{115}$ in calmodulin).

The muscarinic M2 and M4 receptors inhibit cAMP accumulation and enhance arachidonic acid release and calcium levels. The alteration in metabolism of choline to acetylcholine is significant because the M1 and M3 muscarinic cholinergic receptors stimulate processing of the amyloid precursor protein. All muscarinic receptor subtypes appear to stimulate adenylyl cyclase receptor-operated calcium channels and tyrosine kinase activity.

Another significant difference found in AD patients compared to normal controls is the reduction in adenylyl cyclase activity. This decrease appears to be due to a change in the activity, and not the absolute amount, of the enzyme. However, the reduction of β-adrenergic receptor-stimulated cyclization of AMP appears due to alterations in coupling of the GTP binding proteins to the β-adrenergic receptor.

It appears that SAM Pathway No. 2 is enhanced in AD brains. SAM decarboxylase activity is enhanced, which would raise levels of spermidine and spermine. Brain SAM decarboxylase activity is increased in AD, suggesting the involvement of the polyamine system in the brain reparative and/or pathogenetic mechanisms of AD (Morrison et al., *Neurosci. Lett.* 154:141–144 (1993)). These polyamines not only control methylation, but also regulated the sensitivity of NMDA-type glutamate receptors in the brain. Spermine also serves as a cofactor of casein kinase 2. Both the activity and the amount of this enzyme are reduced in AD brains.

The cysteine proteinases cathepsin B and L are elevated. AD cells fail to synthesize mRNA encoding the 40 kDa form of 2',5'-oligoadenylate (2–5A) synthetase; and have significantly lower levels of SAM in the CSF. Epinephrine levels are also lower due to a reduction in the activity of phenylethanolamine N-methyl transferase, which catalyzes methylation by SAM of norepinephrine. Consideration of the foregoing patterns suggests that suitable SAM metabolites for manipulation would include SAM, biotin and polyamines. Other intermediates that may be influenced by the SAM pathways are apoE4, β amyloid core protein, choline and acetylcholine, L-carnitine, NMDA-type glutamate receptor, vitamin $B_{12}$, folate, epinephrine and norepinephrine. These intermediates may also be used as affinity chromatography ligands as described above to determine the regulatory relationships with SAM pathways between disease and nondiseased states.

Thus, in the case of AD, as with cancer (described herein), the parameters associated with the condition have been identified and those target SAM pathways or metabolites aberrant in AD have been identified. In general, the methylation state in the AD patient should be upregulated, and polyamine concentrations should be lowered. An increase in biotin, folate and vitamin $B_{12}$ concentrations should also be beneficial.

Other intermediates that may be influenced by the SAM pathways are apoE4, βamyloid core protein, choline and acetylcholine, L-carnitine, NMDA-type glutamate receptor, epinephrine and norepinephrine. These intermediates may also be used as affinity chromatography ligands as described above to determine the regulatory relationships with SAM pathways between disease and nondiseased states.

EXAMPLE V

Use of the SAM Paradigm in Diabetes and Obesity

Diabetes mellitus (referred to herein simply as "diabetes") involves major alterations in sugar metabolism and fatty acid metabolism, and manifests itself in a number of ways, including sorbitol-induced cataracts in eye lenses leading to blindness, increased protein and lipid catabolism with the formation of ketone bodies such as acetoacetic acid and acetone, impaired wound healing and electrolyte depletion (Graig et al., *Modern Pharmacology*, Fourth Ed, Little, Brown and Co., Boston, pp 802–808, 1994). Diabetes mellitus has been classified into insulin-dependent diabetes (IDDM or Type I Diabetes) and non-insulin-dependent diabetes (NIDDM or Type II Diabetes). The characteristics of these two types have been summarized by Graig et al., supra. One of the main differences between Type I and Type II disease is the total dependence of the former on insulin therapy in contrast to the latter where insulin is usually required 20–30% of the time. Resistance to insulin-mediated glucose disposal is increased in association with obesity, high blood pressure and NIDDM (Maheux et al. *Hypertension* 24:695–698 (1994)). Obesity predisposes a subject to development of diabetes.

Biotin levels are altered in diabetes. Biotin regulates levels of glucokinase and the insulin receptor and has major effects on expression and activities of key glycolytic enzymes. In diabetic mice, glucokinase activity is significantly reduced but is increased by feeding biotin. The stimulatory effects of biotin on this activity were equivalent to treatment with insulin. Biotin also affected the activities of phosphofructokinase and pyruvate kinase in diabetic animals. In normal biotin-deficient mice, glucokinase activity is reduced by 40–45%, and in starved rats the level of glucokinase is regulated by biotin. Increasing the $CO_2$ levels in cultured rat liver cells led to an increase in the synthesis of glycogen from glucose. Treatment of cultured rat hepatocytes led to a 3-fold increase in cGMP and a 4-fold increase in glucokinase within 6 hours. This biotin-mediated increase in glucolinase activity, however, required the presence of insulin, suggesting an intimate relationship between these two cellular regulators. Biotin-deficient rats also had reduced levels of oxidized NAD and ubiquinone.

In biotin-deficient mammals, the glucose-tolerance curves and the enhanced levels of ketone bodies excreted in the urine are nearly identical to those found in mild late-onset diabetes in humans. Mitochondrial lipids were also reduced which led to reduced ratios of P/O. Thus reductions in both glycolysis and oxidative phosphorylation resulted in reduced energy levels. Biotin supplementation improves glucose and insulin tolerance in genetically diabetic mice (Reddi et al., *Life Sci.* 42:1323–1330 (1988)). In Type I diabetes, methylation of phospholipids caused depressed $Na^+/K^+$ ATPase activity (Kowluru et al., *Cell. Biochem. Funct.* 10:95–101 (1992)), Water-soluble vitamins are decreased in various tissues (Ratzman et al., *Horm. Metab. Suppl.* 26:103–105 (1992)), membrane polyunsaturated fatty acids are increased while saturated fatty acids are decreased (Ruiz-Gutierrez et al., *Diabetologia* 36:850–856 (1993)).

In type II diabetes, cholesterol, HDL-C and LDL-C levels are increased (Nishina et al., *Metabolism* 43:554–8 (1994)), linolenic acid in phospholipids is decreased, polyunsaturated fatty acids in phospholipids are increased (Pelikanova et al., *Cas. Lek Cesk.*, 129:1605–1610 (1990)) and hyperinsulinemia is linked to alternatively spliced insulin receptor RNA (Huang et al., *J. Clin. Invest.* 94:1289–1296 (1994))

Obesity

In Aiapy/- mice, the methylation state is correlated with differential expression of the agouti allele responsible for obesity and excessive amounts of yellow pigment in the coat (Michaud et al., *Genes, Dev.* 8:1463–1472 (1994)). Line et al. (J. *Formos. Assoc.* 91:665–8 (1992)) indicated that abnormal brain serotonin synthesis in obese mice, regulated by calmodulin, may interact with calcium ions to complete the activation of enzyme synthesis by serotonin in the development of obesity.

Carnitine supplementation may improve lipid metabolism in the obese subject (Shimura et al., *J. Vet. Med. Sci.* 55:845 (1993)).

EXAMPLE VI

Use of the SAM Paradigm in Neurologic and Psychiatric Diseases

A. Parkinson's Disease

The onset of symptoms of Parkinson's disease is usually quite gradual, with the most prominent features being tremor, rigidity and bradykinesia. The levels of L-DOPA and L-dopamine are regulated by methylation and the methylation pathways are altered. In the table below other aberrant SAM or related metabolites are noted, illustrating the involvement of these metabolites in this disease.

TABLE X

Parkinson's Disease

| SAM or Related Metabolite | Status | Description |
|---|---|---|
| Polyamine[1] | | Polyamine binding site on NMDA receptor |
| Methylation-Nonspecific N-methylase[2] | Increased | Bioactivation to yield neurotoxins |
| Acetyl-L-carnitine[3] | | Protects Toxicity above |
| $Ca^{2+}$/calmodulin-dependent protein kinase II[4] | Increased | Calmodulin regulation depends on methylation |
| Lysolecithin/ sphingomyelin[5] | Increase in serum | |
| SAM[6] | Increased | L-DOPA depletes SAM |
| Vitamin $B_{12}$[7] | Decreased | |

[1]Gerlach et al., J. Neural. Transm. Suppl. 41:177 (1994);
[2]Naoi et al., J. Neural. Transm. Suppl. 41:197 (1994);
[3]Boddis-Wollner et al. J. Neurol. Transm. Park, Dis. Dement. Sect. 3:63–72 (1991);
[4]Iwatsubo et al., Acta Neuropathol. Brln. 82:159 (1991);
[5]Alimov et al., Zh. Nevropatol. Psikhiatr. Im. S.S. Korsakova 90:35 (1990);
[6]Benson et al., Neurochem. Res. 18:325 (1993);
[7]Nadeau, South Med. J. 84:S41 (1991)

2. Depression

The major neurotransmitter systems which are altered in depression, are regulated by methylation. For example, the relative levels of dopamine, norepinephrine, epinephrine, serotonin and melatonin are regulated, in part, by methylation. This suggests that molecules involved in one-carbon metabolism (e.g., folic acid, vitamin $B_{12}$, methionine and SAM) will have a major role in modulation of neurotransmitter levels and thus of syndromes/diseases related to these levels. Consistent with this, LiCl which is known to have major effects on depression, has significant effects on cellular methyltransferase activity.

TABLE XI

Depression

| SAM or Related Metabolite | Status | Description |
|---|---|---|
| SAM[1] | Decreased | Parenteral SAM safe — antidepressant |

[1]Bell et al., Acta Neurol. Scand. Suppl. 154:15 (1994)

Manic Depression

Lithium, used to treat this disorder, has known major effects on methyltransferases which regulate neurotransmitters involved in manic states.

EXAMPLE VII

Use of the SAM Paradigm in Atherosclerosis

For the most part atherosclerosis goes undiagnosed unless the patient has hypertension, chest pain, heart attack or stroke. The key symptom is thickening of walls of veins and arteries. Hyperhomocysteinemia has been proposed as an independent risk factor for this disease (Robinson et al, Cleve. Clin. J. Med., 61: 438–450 (1994)). Some additional aberrant SAM or related metabolites are listed in Table XII.

Nitric oxide (NO) release is enhanced by the presence of calmodulin, and NO is the epithelial growth factor which increases proliferation of cells in the vessel wall, a step in the formation of atherosclerotic plaque. Other neurotransmitters required for normal function which are aberrant in atherosclerosis include epinephrine, norepinephrine, acetylcholine and serotonin, all of which are SAM metabolized molecules. One major class of therapeutics for hypertension (atherosclerosis) are drugs which block the β-adrenergic receptor. β-adrenergic receptors are upregulated in atherosclerosis due to long term exposure to high levels of catecholamines (epinephrine and norepinephrine).

TABLE XII

Atherosclerosis (ATS)

| SAM or Related Metabolite | Status | Description |
|---|---|---|
| Polyamines[1] | Increased | Cellular proliferation of ATS in lesion |
| Methylation[2] | | Hypomethylation correlates with transcriptional activity |
| Acetylcarnitine[3] | | Improves blood flow |
| Calmodulin[4] | Increased | Calmodulin regulation depends on methylation |
| Essential phospholipids[5] | | Reduced in experimental atherosclerosis (rabbits) |
| Vascular cell adhesion molecule 1 (VCAM1)[6] | | VCAM1 domain 4 is deleted by alternative splicing |
| Homocysteine | | High homocysteine level is a major predisposing factor in ATS |

[1]Nishida et al., Atherosclerosis 83:119 (1990);
[2]Lincke et al., J Biol. Chem. 266:5303 (1991);
[3]Postiglione et al., Int. J. Clin. Pharmacol. Res. 10:129 (1990);
[4]Mehta, Biochem. Med. Metab. Biol. 44:151 (1990);
[5]Wojcicki et al., Atherosclerosis 93:7 (1992)

EXAMPLE VII

Use of the SAM Paradigm in Cystic Fibrosis

Polyamines regulate endocytosis and exocytosis from coated pits. In particular, polyamines regulate excretion. Cystic fibrosis patients have aberrant polyamine levels.

TABLE XIII

Cystic Fibrosis

| SAM or Related Metabolite | Status | Description |
|---|---|---|
| Calmodulin[1] | | Defective membrane chloride channel regulation. Activate Calmodulin to correct |
| Polyunsaturated fatty acids[2] | Decreased | |
| Total saturated and monounsaturated fatty acids[2] | Increased | |
| Cystic fibrosis transmembrane conductance regulator (CFTR)[3] | | Omission of exon 12 in CFTR by alternative splicing |
| Polyamines | | Involved in modulation of secretion; aberrant levels in cystic fibrosis |

[1]Wagner et al., Nature 349:793 (1991);
[2]Lloyd et al., Am. J. Clin. Nutr. 54:1029 (1991)

An aerosolized spray of an ornithine decarboxylase inhibitor (e.g., DFMO) or a SAM decarboxylase inhibitor may be used to correct endogenous up-regulation. In addition, an aerosolized spray of a polyamine may be used to correct endogenous down-regulation.

EXAMPLE VIII

The Sam Paradigm and other Diseases or Conditions

A Crohn's disease.

Crohn's disease is a nonspecific chronic transmural inflammatory disease that most commonly affects the distal ileum and colon but may also occur in any point of the GI tract from the mouth to the anus. Biotin levels are a significantly reduced in patients with this disease. The activity of natural killer cells are also greatly diminished. Treatment of Crohn's disease patients with biotin increases their natural killer cell function. Biotin is also necessary for the generation of cytotoxic T lymphocytes (Okabe et al., *Digest Dis. Sci*. 33:1495–1501 (1988)

TABLE XIV

Crohn's Disease

| SAM or Related Metabolite | Status | Description |
|---|---|---|
| Carnitine[(1)] | Increased | |
| Phospholipid[(2)] | | Fish oil (eicosapentaneoic, docosahexaneoic, free fatty acids) used as treatment |
| Biotin | Decreased | |
| Vitamin $B_{12}$ | | Reduced in Crohn's disease |

[(1)]Demirkol et al., Eur. J. Pediatr. 153:565 (1994);
[(2)]Belluzzi et al, Dig. Dis. Sci. 39:2589 (1994);
[(3)]Matausue et al., J. Patrenter. Enter. Nutr. 9:760 (1994)

TABLE XV

Circadian Rhythm (CR)

| SAM or Related Metabolite | Status | Description |
|---|---|---|
| Polyamines[(1)] | Increased in morning | 24 hr cycle in humans |
| Methylation[(2)] | | Regulates melatonin |
| Acetylcarnitine[(3)] | | Restores daily β-endorphin in rats exposed to continuous light |
| Calmodulin[(4)] | | Inhibitors phase shift CR in vivo (locomotor activity) |
| Lipids[(5)] | | Distinct rhythms altered by feeding |
| cAMP-Responsive element modulator (CREM)[(6)] | | CREM is alternatively spliced. CREM function changed from antagonist to activator |
| SAM[(7)] | Increased during light, decreased during dark | |

[(1)]Poyhonen et al, Am. J. Clin. Nutr. 52:746–751 (1990);
[(2)]Reiter, Adv. Exp. Med. Biol. 294:149–158 (1991);
[(3)]Genazzani et al., Eur. J. Pharmacol. 186:177–180 (1990);
[(4)]Shibita et al J. Biol. Rhythms 9:27–41 (1991);
[(5)]Nakano et al, Am. J. Physiol. 258:G653–9 (1990)
[(6)]Foulkes et al., Nature 362:264–7 (1993);
[(7)]Schalinske et al., Biofactors 3:265–268 (1992)

B. Circadian Rhythmicity

Serotonin is converted by acetylation and methylation to melatonin, the timeclock of the body.

C. Rheumatoid Arthritis (RA)

Chondrocytes over-proliferate in a cancer-like manner. Levels of polyamines and of LDH5 are increased. Aberrant cytokine production, including interferon, occurs. Interferon generates picolinic and quinolinic acid, which lead to inhibition of ADP ribosylase. It also leads to NAD formation. NAD inhibits SAH hydrolase which could in turn inhibit methylation. RA patients have aberrant tryptophan and histidine metabolism and often suffer from depression, having low serotonin levels, but are not known to suffer from schizophrenia. The immunosuppressive action of methotrexate, the leading drug for RA maintenance and cure, is believed to result from inhibition of the conversion of AICAR to inosine monophosphate.

A genetic predisposing or risk factor for RA is type of DR type of MHC class II antigens. These antigens are associated with binding of adenosine deaminase which also leads to inosine monophosphate generation. 90% of RA patients have antibodies to Epstein Barr virus. It is believed that RA begins as a bacterial infection, but it could also be viral. Small retroviral-like RNAs have been found in the synovial fluid of RA patients.

D. Male Pattern Baldness and Gray Hair

Biotin deficiency causes alopecia as well as gray hair. Hair loss reversibly occurs following treatment with strong methylation inhibitors, e.g., methotrexate which inhibits dihydrofolate reductase and thus the transfer of methyl groups by tetrahydrofolate. Male pattern baldness can be reversed in males by estrogen which up-regulates methylation in estrogen-sensitive cells. Minoxidil is a lysine hydroxylase inhibitor. Hydroxylation of lysine in collagen leads to crosslinking by formation of pyridinium derivatives. Upon hydrolysis of collagen, such derivative become potent methylation inhibitors ("pyridinoline", the methylation inhibitor found in brain extract).

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general the principles of the invention and including such departures from the present disclosure as come within known or customary practice within the art to which the invention pertains and as may be applied to the essential features hereinbefore set forth as follows in the scope of the appended claims.

What is claimed is:

1. A method to identify a therapeutic composition or protocol which ameliorates a disease or undesired condition in a subject, which method relies upon recognition of the existence of, and the interconnections between, eight SAM pathways shown in FIGS. 2–9, herein, which method comprises:
    (a) determining the presence of said disease or condition in said subject;
    (b) examining more than 1 of said eight SAM pathways and the interconnections therebetween and identifying any abnormalities by determining
        (i) concentrations of metabolites, and/or
        (ii) concentrations or activities of enzymes, and/or
        (iii) levels of cellular functions,
    that are participants in, or are results of, SAM pathways thereby obtaining a data set of the differences of said concentrations, activities, and/or levels from corresponding normal concentrations, activities, and/or levels;
    (c) analyzing said data set by ascertaining, for each difference in concentration, activity, and/or level the position or function of the corresponding metabolite, enzyme or cellular function in said SAM pathways or the interconnections therebetween, so as to determine which of one or more metabolites and/or enzymes and/or cellular functions of said SAM pathways is a causative agent of said differences in concentrations, activities or levels in said data set; and
    (d) identifying a therapeutic composition or protocol which acts to restore said pathways toward normality, thereby identifying a composition or protocol that ameliorates said disease or condition.

2. The method of claim 1 wherein said data set is converted into digital computer-readable form.

3. The method of claim 1 wherein said cellular function is selected from the group consisting of: (i) binding of a metabolite to receptors therefor, (ii) transport of a metabolite, (iii) membrane fluidity, (iv) membrane potential, (v) cell growth and (vi) programmed cell death.

4. The method of claim 1 wherein, in step (d), said identifying of said composition is performed by screening combinatorial libraries of candidate compounds.

5. The method of claim 1 wherein
    in step (b), said data set of differences in concentrations of metabotites, and/or concentrations or activities of enzymes, and/or levels of cellular functions,
    between said subject and normal concentrations, activities, and/or levels reflects pathway changes in response to the progression of said disease or condition in said subject; and
    wherein step (b) further comprises
        measuring said data set as a function of time and progression of said disease or condition after onset, or diagnosis, thereof to obtain a metabolic data set in combination with recording clinical manifestations of said progression to obtain a clinical data set; and
        obtaining a combined data set by comparing said metabolic data set with said clinical data set to obtain a combined data set; and
    wherein step (c) further comprises analyzing the combined data set; and
    wherein the identified therapeutic composition or protocol of step (d) further ameliorates said clinical manifestations; and
    wherein said metabolic, clinical, or combined data sets characterize said disease or condition or characterize the progression thereof.

6. The method of claim 5 wherein one or more of said metabolic, clinical, or combined data sets is arranged as an electronically readable and retrievably profile characterizing a disease or condition or the progression thereof in digital computer-readable form.

7. The method of claim 1 wherein the said data set is obtained by measurements performed on a biological sample from said subject.

8. The method of claim 7 wherein said identifying abnormalities step of (b) comprises determining in said biological sample:
    (1) the concentration of metabolites selected from the group consisting of:
        (A) for Pathway 1, S-adenosylmethionine (SAM), S-adenosyl homocysteine (SAH), adenosine, homocysteine, glutathione, glutathione disulfide, cystathionine, α-ketobutyrate, cysteine, cystine, taurine, choline, betaine, dimethylglycine, methylglycine, glycine, serine, folate, tetrahydrofolate, methylene tetrahydrofolate, methyltetrahydrofolate, adenosine triphosphate, methylated vitamin B12, an O- or N-methylated product of a methylating enzyme and a demethylated product of a demethylating enzyme.
        (B) for Pathway 2, SAM, decarboxylated adenosylmethionine, methylthioadenosine, ornithine, putrescine, spermine, spermidine, $N^1$-acetylspermidine, and $N^1$-acetylspermine; and (C) for Pathway 8, biotin, biocytin, and biotin-protein conjugates, (2) the concentration or activity of enzymes, or the level of cellular functions, selected from the group consisting of:

(A) for Pathway 1, adenosylmethionine synthetase, $N^5$-methyltetrahydrofolate:homocysteine methyltransferase, betaine:homocysteine methyltransferase, cystathionine β-synthase, γ-cystathionase, methylene tetrahydrofolate reductase, SAH hydrolase, an O-methyltransferase, an N-methyltransferase, adenosine deaminase, a glutathione synthetic enzyme and a glutathione degradative enzyme;

(B) for Pathway 2, adenosinemethionine decarboxylase, spermidine synthetase, spermine synthetase, spermidine-spermine $N^1$-acetyltransferase, polyamine oxidase, methylthioadenosine phosphorylase, ornithine decarboxylase and polyamine transport; and (C) for Pathway 8, biotinase, pyruvate carboxylase, acetyl-CoA carboxylase, propionyl-CoA carboxylase, 3-methylcrotonyl-CoA carboxylase, geranyl-CoA carboxylase, mixed function oxidase, L-cysteine sulfonate decarboxylase and biotin transport;

thereby obtaining said first data set of differences from normal concentrations of metabolites, concentrations of enzymes, activities of enzymes or cellular functions.

9. A method according to claim 8 wherein the identifying abnormalities step of (b) is performed for at least one metabolite or enzyme concentration, enzyme activity or cellular function level by subjecting said biological sample to a labeling analysis of metabolites comprising the steps of:

(A) contacting said sample with detectably labeled SAM or a detectably labeled first metabolite of SAM, whereby the label from SAM or from said labeled first metabolite is donated to an acceptor molecule in one of said SAM pathways, said acceptor molecule being a second metabolite that is in a SAM pathway distinct from the SAM pathway of said labeled first metabolite;

(B) isolating and measuring the amount of said labeled acceptor molecule produced in step (A), thereby identifying and quantifying said labeled second metabolite;

(C) performing steps (A) and (B) with a sample from a normal subject or with another appropriate control or reference sample; and (D) comparing the results of step (B) with the results in step (C).

10. A method according to claim 8 wherein the identifying abnormalities step of (b) is performed for at least one metabolite or enzyme concentration, enzyme activity or cellular function level by subjecting said biological sample to affinity chromatographic separation using immobilized affinity ligands, which separation comprises the steps of:

(A) contacting the sample with one or more immobilized ligands having binding specificity for said metabolite or said enzyme, and allowing material in the sample to bind to the ligand;

(B) removing any material of the sample not bound to the ligand;

(C) eluting bound material from the ligand to produce an eluate, in a single fraction or as sequential fractions eluted with increasing salt concentrations or with different competitive ligands which compete for binding to said metabolite or enzyme;

(D) identifying the presence and measuring the amount of any bound and eluted material in the eluate;

(E) performing steps (ii)(A)–(D) with a corresponding biological sample from a normal subject and (F) comparing the results of step (D) with the results of step (E), wherein an increase or a decrease in the amount of said metabolite or enzyme in said eluate in step (D) compared to step (E) identifies said abnormal metabolite and/or enzyme and thereby identifies an abnormal SAM pathway or pathways.

11. The method of claim 10 wherein the sample is contacted with more than one immobilized ligand in contacting step (A).

12. The method of claim 10, comprising the additional steps, prior to step (D), of (H) contacting the eluate of step (C) with an additional one or more immobilized affinity ligands different from said first one or more immobilized ligands, which additional one or more affinity ligands binds an enzyme or metabolite of a SAM pathway, and allowing material in said eluate to bind said additional one or more immobilized affinity ligands;

(I) removing any material of the eluate of step (C) not bound to said additional one or more immobilized affinity ligands of step (H);

(J) eluting any material bound to said additional one or more immobilized affinity ligands, thereby producing an eluate;

(K) identifying the presence or measuring the amount of any previously bound and subsequently eluted material in the eluate of step (J);

(L) performing steps (A) to (C) and (H) to (K) with a biological fluid from a normal subject or a subject not having said disease or condition; and (M) comparing the results of step (L) with the results of step (K), wherein an increase or a decrease in the amount of said metabolite or enzyme in said eluate in step (K) compared to step (L) identifies said abnormal metabolite and/or enzyme and thereby identifies an abnormal SAM pathway or pathways.

13. The method of claim 1 wherein said disease or condition is selected from the group consisting of a wound, cancer, multiple sclerosis, Alzheimer's disease, Parkinson's disease, depression, atherosclerosis, cystic fibrosis, diabetes, obesity, Crohn's disease and altered circadian rhythmicity.

14. The method of claim 13 wherein said condition is a wound, said metabolites comprise one or more of SAM, ethylene, biotin, polyamines, nicotinamide, queuine and queuosine.

15. The method of claim 13 wherein said disease is cancer and said metabolites, enzyme activities or cellular functions comprise one or more of DNA methylation, queuosine and wye-base incorporation into tRNA, SAM synthesis, polyamine synthesis, ethylene synthesis, biotin, methylthioadenosine and 5-deoxyadenosine.

16. The method of claim 13 wherein said disease is multiple sclerosis and said metabolites or enzyme activities comprise one or more of methyl transferase activity and S-adenosyl homocysteine.

17. The method of claim 13 wherein said disease is Alzheimer's disease and said metabolites, enzyme activities or cellular functions comprise one or more of methylation levels, SAM, biotin, polyamines, folate and vitamin $B_{12}$.

18. The method of claim 13 wherein said disease is Parkinson's disease and said metabolites or activities comprise one or more of polyamines, nonspecific N-methylase, acetyl-L-carnitine, $Ca^{2+}$/calmodulin-dependent protein kinase II, lysolecithin, sphingomyelin, SAM and vitamin $B_{12}$.

19. The method of claim 13 wherein said disease is atherosclerosis and said metabolites, enzyme activities or cellular functions comprise one or more of methylation levels, polyamines, acetyl-L-carnitine, calmodulin, and essential phospholipids.

20. The method of claim 13 wherein said disease is cystic fibrosis said metabolites, enzyme activities or cellular functions comprise one or more of calmodulin, polyunsaturated fatty acids, total saturated and monounsaturated fatty acids, and cystic fibrosis transmembrane conductance regulator.

21. The method of claim 13 wherein said condition is obesity said metabolites, enzyme activities or cellular functions comprise one or more of methylation levels, serotonin, calmodulin and carnitine.

* * * * *